US012686871B2

(12) United States Patent
Weinstock et al.

(10) Patent No.: US 12,686,871 B2
(45) **Date of Patent: \*Jul. 21, 2026**

(54) **GENETICALLY ENGINEERED *VIBRIO* SP. AND USES THEREOF**

(71) Applicant: Codex DNA, Inc., San Diego, CA (US)

(72) Inventors: Matthew T Weinstock, San Diego, CA (US); Christopher M. Wilson, San Diego, CA (US)

(73) Assignee: Telesis Bio Inc, San Diego, CA (US)

( * ) Notice: Subject to any disclaimer, the term of this patent is extended or adjusted under 35 U.S.C. 154(b) by 1238 days.

This patent is subject to a terminal disclaimer.

(21) Appl. No.: 17/541,163

(22) Filed: Dec. 2, 2021

(65) Prior Publication Data

US 2022/0090098 A1     Mar. 24, 2022

Related U.S. Application Data

(62) Division of application No. 15/687,373, filed on Aug. 25, 2017, now Pat. No. 11,203,761.

(60) Provisional application No. 62/380,341, filed on Aug. 26, 2016.

(51) Int. Cl.
*C12N 15/74*          (2006.01)

(52) U.S. Cl.
CPC .................................... *C12N 15/74* (2013.01)

(58) Field of Classification Search
None
See application file for complete search history.

(56) References Cited

U.S. PATENT DOCUMENTS

| | | | |
|---|---|---|---|
| 4,963,487 A | 10/1990 | Schimmel | |
| 5,747,028 A | 5/1998 | Calderwood et al. | |
| 6,833,135 B1 | 12/2004 | Frazao et al. | |
| 10,377,997 B1 * | 8/2019 | Weinstock ........... | C12N 9/1247 |
| 11,447,755 B2 * | 9/2022 | Weinstock ........... | C12N 9/1247 |
| 12,331,326 B2 * | 6/2025 | Weinstock ...... | C12Y 207/07006 |
| 2003/0108872 A1 | 6/2003 | Sulavik et al. | |
| 2003/0224481 A1 | 12/2003 | Elledge et al. | |
| 2004/0241847 A1 | 12/2004 | Okuyama et al. | |
| 2008/0233623 A1 | 9/2008 | Chang et al. | |
| 2013/0121915 A1 | 5/2013 | Pass et al. | |
| 2016/0186147 A1 | 6/2016 | Cady et al. | |

FOREIGN PATENT DOCUMENTS

| | | |
|---|---|---|
| WO | WO 1999/61634 | 12/1999 |
| WO | WO 2014/201394 | 12/2014 |
| WO | WO 2014/202089 | 12/2014 |

OTHER PUBLICATIONS

Abe et al., "Isolation and characterization of a cold-induced noncultur-able suppression mutant of Vibrio vulnificus", Microbiological Research, vol. 162, No. 2, Mar. 13, 2007, pp. 130-138.

Blokesh et al., "The Extracellular Nuclease Ons and Its Role in Natural Transformation of Vibrio cholerae"; Journal of Bacteriology, Aug. 29, 2008, vol. 190, No. 21, pp. 7232-7240.
Clamby. "Re: What is the best environment to store *E. coli* bacteria?", Oct. 20, 1997, XP055668062, Retrieved from the Internet: URL: http://www.madsci.org/posts/arch ives/dec97/ 877396445.M r.htm 1, [retrieved on Feb. 12, 2020].
De Boer et al., "The Tac Promoter: A Functional Hybrid Derived from the TRP and LAC Promoters", Proceedings of the National Academy of Sciences, vol. 80, Jan. 1, 1983, pp. 21-25.
Extended European Search Report issued on Feb. 21, 2020, regarding EP 17 84 4539.
International Search Report issued on Nov. 2, 2017 regarding PCT/US2017/048743.
Knauf et al., "Cloning, Sequence, and Phenotypic Expressions of Kata, which Encodes the Catalase of Lactobacillus Sake LTH677", Applied and Environmental Microbiology, vol. 58, No. 3, Mar. 1, 1992, pp. 832-839.
Kong et al., "Role of catalase and oxyR in the viable but noncultur-able state of Vibrio vulnificus", Fems Microbiology Ecology, vol. 50, No. 3, Nov. 22, 2004, pp. 133-142.
Lee et al. "Vibrio natriegens, a new genomic powerhouse"; bioRxiv, Jun. 12, 2016, pp. 1-30.
Lhoest et al., Eur. J. Biochem., 121:33-37 (Year: 1981).
Lee et al., "Vibrio natriegens NBRC 15636 = ATCC 14048 = DSM 759 chromosome 2, complete sequence"; GenBank: CP009978.1, Dec. 3, 2015.
Li et al., "The importance of the viable but non-culturable state in human bacterial pathogens"; Frontiers in Microbiology, Jun. 2, 2014, vol. 5, Article 258, pp. 1-20.
Nilsson et al., "Resuscitation of Vibrio vulnificus from the Viable but Nonculturable State", Journal of Bacteriology, Aug. 31, 1991, vol. 173, No. 6, pp. 5054-5059.
Shrivastava et al. "A novel alkyl hydroperoxidase (AhpD) of Anabaena PCC7120 confers abiotic stress tolerance in *Escherichia coli*", Functional and Integrative Genomics, vol. 15, No. 1, Nov. 13, 2014, pp. 77-92.
Varnado et al., "System for the expression of recombinant hemoproteins in *Escherichia coli*", 35 Protein Expression and Purification, 76-83, 2004.
Wang et al., Roles of Alkyl Hydroperoxide Reductase Subunit C (AhpC) in Viable but Nonculturable Vibrio parahaemolyticus, Applied and Environmental Microbiology, Jun. 15, 2013, pp. 3734-3743.

(Continued)

*Primary Examiner* — Nancy J Leith

(57) ABSTRACT

The present disclosure provides engineered *Vibrio* sp. organisms. The organisms can be engineered to have an altered Chromosome II so that the altered Chromosome II can be used in *Vibrio* sp. and other organisms for the cloning or amplification of nucleic acid molecules and for the expression and production of proteins and peptides in a *Vibrio* sp. organism. One or more genetic elements have been deleted from Chromosome II and/or relocated from Chromosome II to Chromosome I. The engineered *Vibrio* sp. organisms of the invention can also have signal sequences fused to proteins or peptides to be secreted from the cell. In some embodiments the engineered *Vibrio* sp. organisms can have sequences that enable them to retain viability after incubation at low temperatures.

12 Claims, 31 Drawing Sheets

Specification includes a Sequence Listing.

(56)         References Cited

OTHER PUBLICATIONS

Weinstock et al., Vibrio natriegens as a fast-growing host for molecular biology, Nature Methods, vol. 13, No. 10, Oct. 1, 2016, pp. 849-851.
Wolf et al., "Temperature effects on the viable but non-culturable state of Vibrio vulnificus", 101 FEMS Microbiology Ecology, 22-29, 1992.

\* cited by examiner

WHITE LIGHT IMAGE:

| wt | wt | lacl | lacl | araBAD | araBAD |
|----|----|------|------|--------|--------|
| BHI | LB | BHI | LB | BHI | LB |

FIG. 8A

| Relative abundance | Unique Peptides | Protein Coverage | Protein annotation† | MW | signal peptide‡ |
|---|---|---|---|---|---|
| 5898 | 38 | 52% | Arabinanase/levansucrase/invertase | 58.92 kDa | yes |
| 3140 | 58 | 73% | Bacterial extracellular solute-binding s, 5 Middle family protein | 57.71 kDa | yes |
| 2304 | 13 | 32% | Gram-negative porin family protein | 39.00 kDa | yes |
| 1783 | 35 | 66% | Maltose ABC transporter, periplasmic maltose-binding protein | 42.26 kDa | yes |
| 1756 | 16 | 48% | Maltoporin | 46.87 kDa | yes |
| 1583 | 21 | 46% | Gram-negative porin family protein | 36.61 kDa | yes |
| 1523 | 19 | 52% | Outer membrane beta-barrel domain protein | 36.26 kDa | yes |
| 1089 | 29 | 76% | TRAP transporter solute receptor, TAXI family protein | 34.50 kDa | yes |
| 968 | 32 | 58% | Peptidase Do family protein | 48.17 kDa | yes |
| 803 | 23 | 67% | Iron(III) ABC transporter, periplasmic iron-compound-binding protein | 37.26 kDa | yes |
| 691 | 30 | 76% | Lysine-arginine-ornithine-binding periplasmic family protein | 28.20 kDa | yes |
| 679 | 23 | 73% | Amino acid ABC transporter periplasmic amino acid-binding portion | 27.70 kDa | yes |
| 664 | 39 | 65% | TonB-dependent Receptor Plug domain protein | 71.82 kDa | yes |
| 586 | 11 | 52% | Outer membrane beta-barrel domain protein | 33.79 kDa | yes |
| 576 | 20 | 52% | Enolase C-terminal domain-like | 45.62 kDa | no |
| 560 | 30 | 51% | GlyGly-CTERM domain protein | 61.60 kDa | yes |
| 521 | 8 | 30% | Lipoprotein | 37.56 kDa | no |
| 513 | 35 | 58% | TonB-dependent siderophore receptor family protein | 75.03 kDa | yes |
| 482 | 11 | 34% | Outer membrane protein W | 23.41 kDa | yes |
| 481 | 9 | 62% | Type III secretion system lipochaperone family protein | 15.80 kDa | no |

FIG. 11

20 days at 4°C

20 days at RT

Figure 15C:
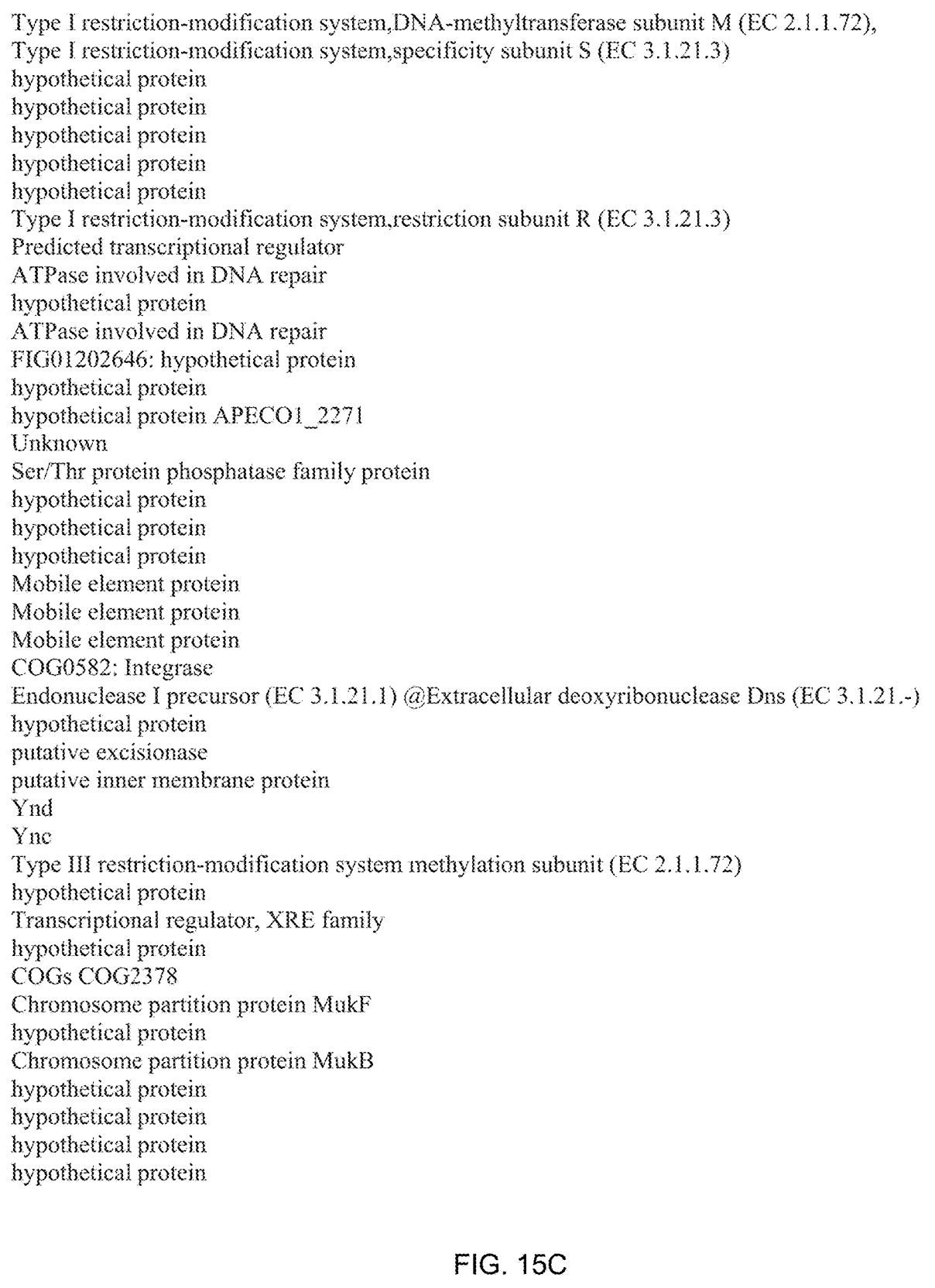

Type I restriction-modification system,DNA-methyltransferase subunit M (EC 2.1.1.72),
Type I restriction-modification system,specificity subunit S (EC 3.1.21.3)
hypothetical protein
hypothetical protein
hypothetical protein
hypothetical protein
hypothetical protein
Type I restriction-modification system,restriction subunit R (EC 3.1.21.3)
Predicted transcriptional regulator
ATPase involved in DNA repair
hypothetical protein
ATPase involved in DNA repair
FIG01202646: hypothetical protein
hypothetical protein
hypothetical protein APECO1_2271
Unknown
Ser/Thr protein phosphatase family protein
hypothetical protein
hypothetical protein
hypothetical protein
Mobile element protein
Mobile element protein
Mobile element protein
COG0582: Integrase
Endonuclease I precursor (EC 3.1.21.1) @Extracellular deoxyribonuclease Dns (EC 3.1.21.-)
hypothetical protein
putative excisionase
putative inner membrane protein
Ynd
Ync
Type III restriction-modification system methylation subunit (EC 2.1.1.72)
hypothetical protein
Transcriptional regulator, XRE family
hypothetical protein
COGs COG2378
Chromosome partition protein MukF
hypothetical protein
Chromosome partition protein MukB
hypothetical protein
hypothetical protein
hypothetical protein
hypothetical protein

Figure 15D:
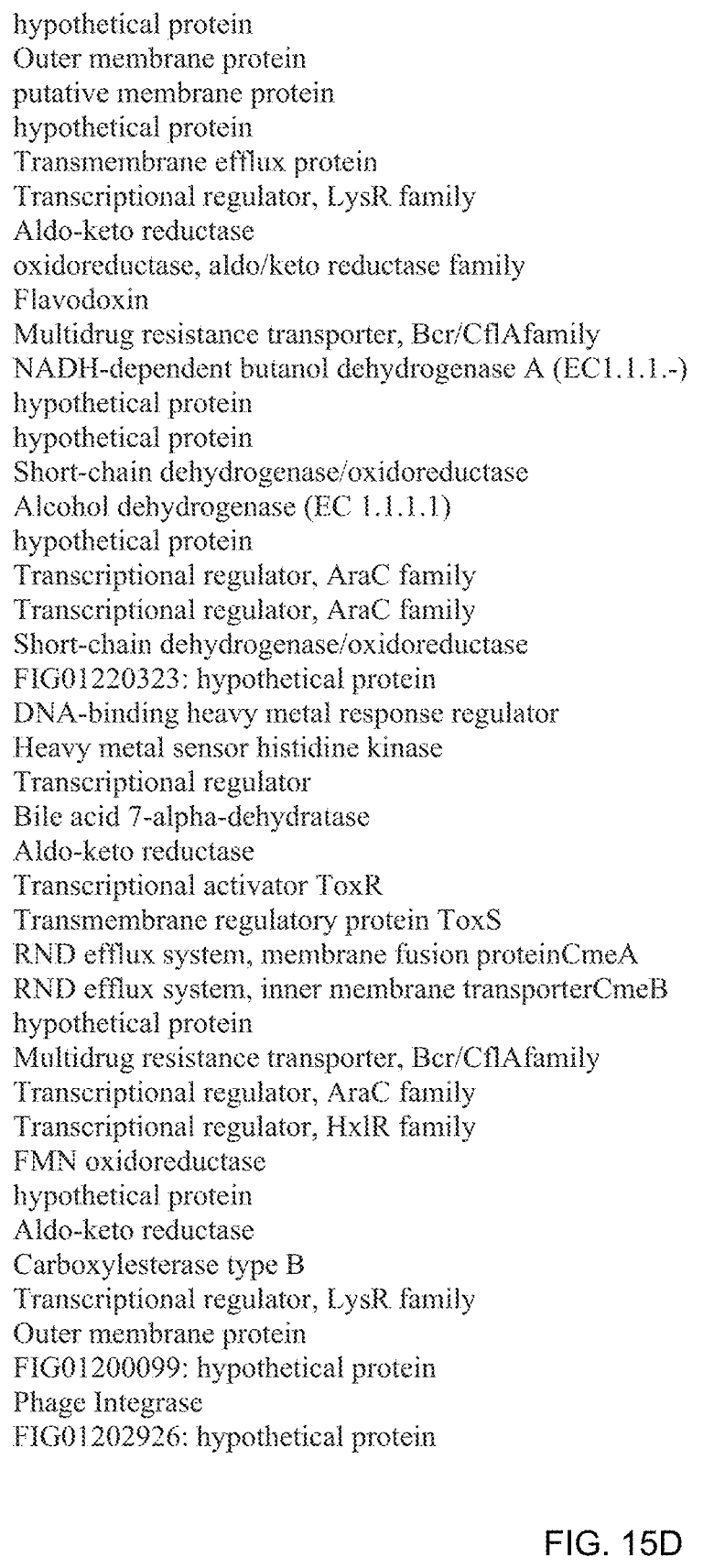

FIG. 15C hypothetical protein
Outer membrane protein
putative membrane protein
hypothetical protein
Transmembrane efflux protein
Transcriptional regulator, LysR family
Aldo-keto reductase
oxidoreductase, aldo/keto reductase family
Flavodoxin
Multidrug resistance transporter, Bcr/CflAfamily
NADH-dependent butanol dehydrogenase A (EC1.1.1.-)
hypothetical protein
hypothetical protein
Short-chain dehydrogenase/oxidoreductase
Alcohol dehydrogenase (EC 1.1.1.1)
hypothetical protein
Transcriptional regulator, AraC family
Transcriptional regulator, AraC family
Short-chain dehydrogenase/oxidoreductase
FIG01220323: hypothetical protein
DNA-binding heavy metal response regulator
Heavy metal sensor histidine kinase
Transcriptional regulator
Bile acid 7-alpha-dehydratase
Aldo-keto reductase
Transcriptional activator ToxR
Transmembrane regulatory protein ToxS
RND efflux system, membrane fusion proteinCmeA
RND efflux system, inner membrane transporterCmeB
hypothetical protein
Multidrug resistance transporter, Bcr/CflAfamily
Transcriptional regulator, AraC family
Transcriptional regulator, HxlR family
FMN oxidoreductase
hypothetical protein
Aldo-keto reductase
Carboxylesterase type B
Transcriptional regulator, LysR family
Outer membrane protein
FIG01200099: hypothetical protein
Phage Integrase
FIG01202926: hypothetical protein

Figure 15E:
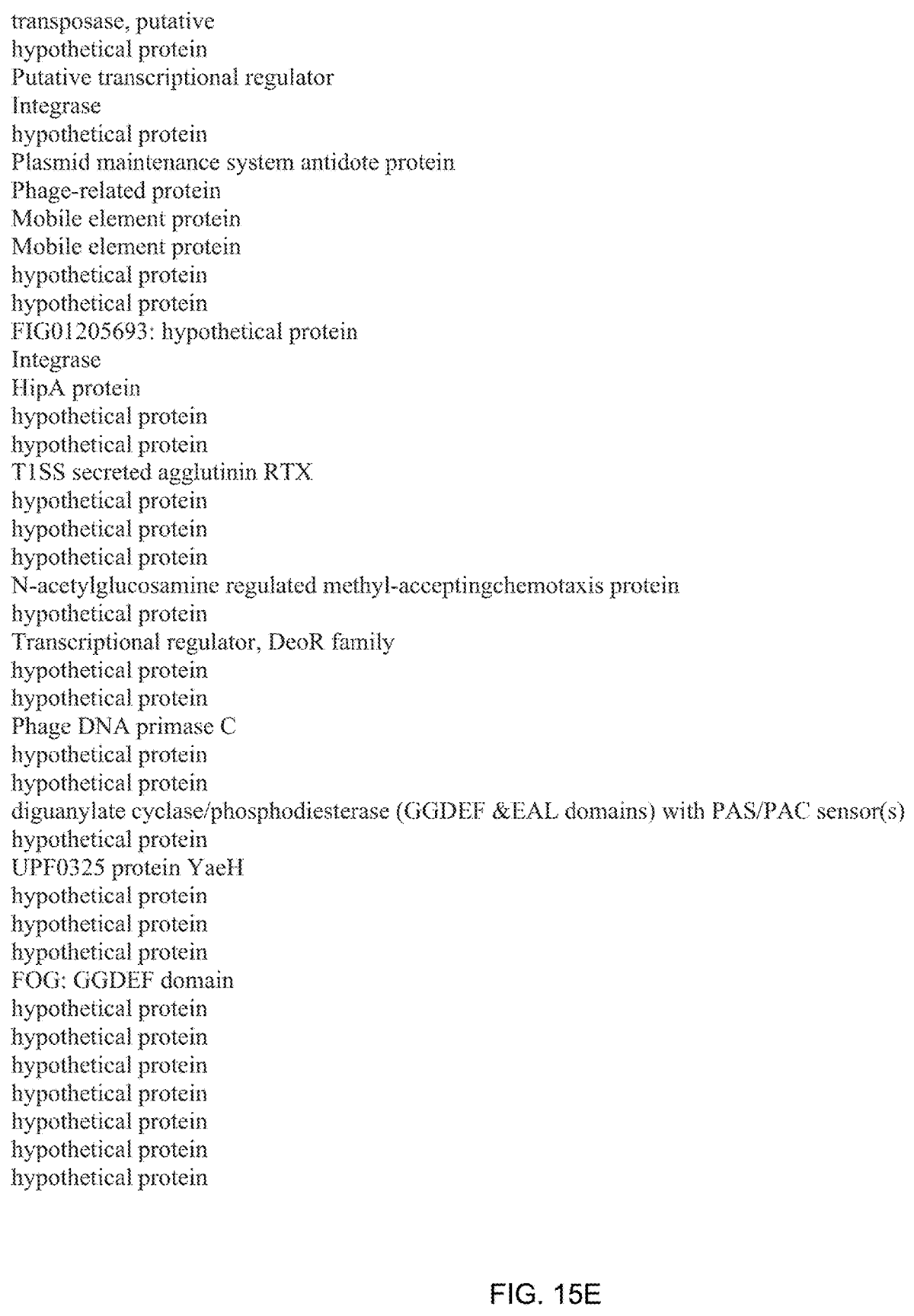

FIG. 15D transposase, putative
hypothetical protein
Putative transcriptional regulator
Integrase
hypothetical protein
Plasmid maintenance system antidote protein
Phage-related protein
Mobile element protein
Mobile element protein
hypothetical protein
hypothetical protein
FIG01205693: hypothetical protein
Integrase
HipA protein
hypothetical protein
hypothetical protein
T1SS secreted agglutinin RTX
hypothetical protein
hypothetical protein
hypothetical protein
N-acetylglucosamine regulated methyl-acceptingchemotaxis protein
hypothetical protein
Transcriptional regulator, DeoR family
hypothetical protein
hypothetical protein
Phage DNA primase C
hypothetical protein
hypothetical protein
diguanylate cyclase/phosphodiesterase (GGDEF &EAL domains) with PAS/PAC sensor(s)
hypothetical protein
UPF0325 protein YaeH
hypothetical protein
hypothetical protein
hypothetical protein
FOG: GGDEF domain
hypothetical protein
hypothetical protein
hypothetical protein
hypothetical protein
hypothetical protein
hypothetical protein
hypothetical protein

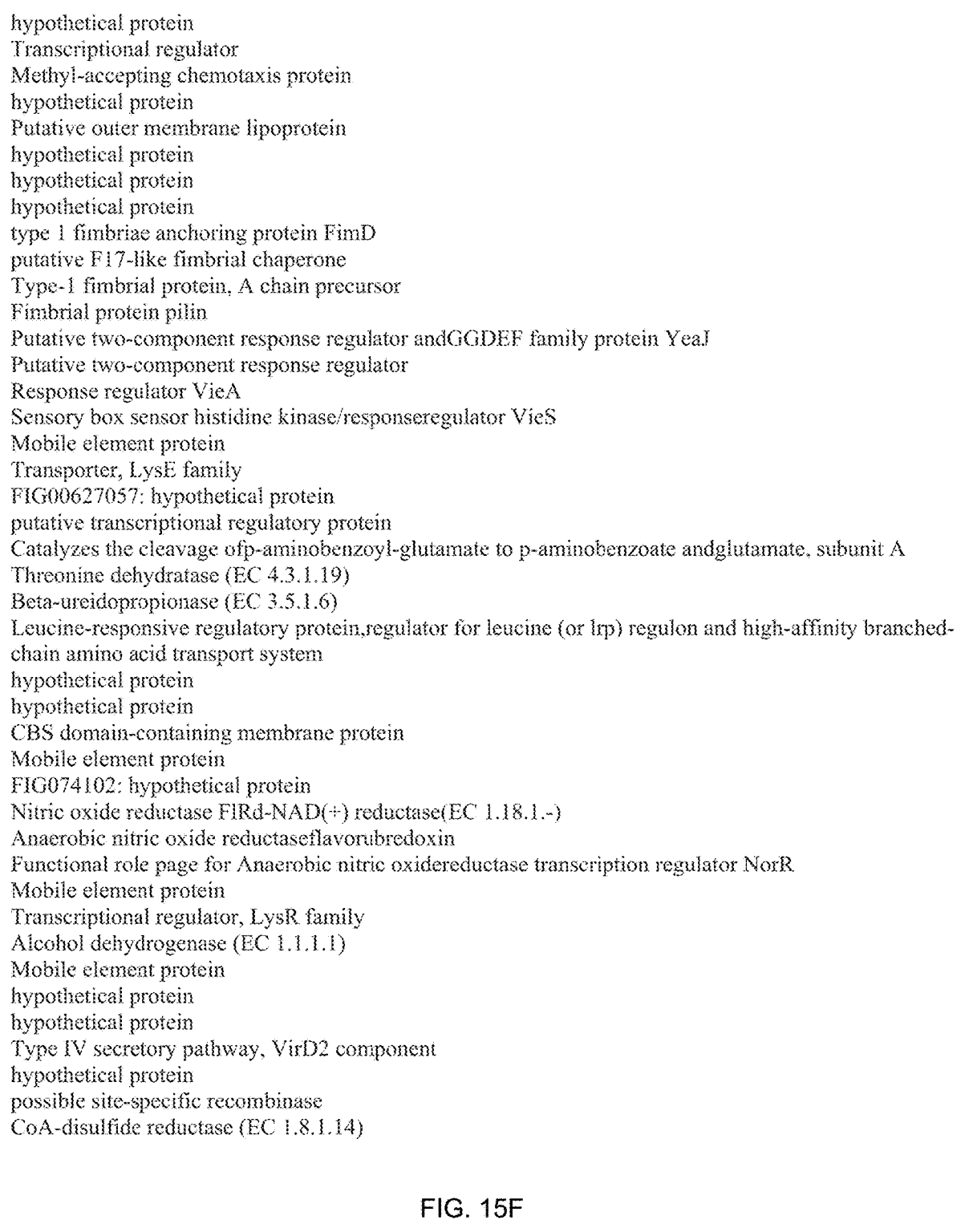

FIG. 15E hypothetical protein
Transcriptional regulator
Methyl-accepting chemotaxis protein
hypothetical protein
Putative outer membrane lipoprotein
hypothetical protein
hypothetical protein
hypothetical protein
type 1 fimbriae anchoring protein FimD
putative F17-like fimbrial chaperone
Type-1 fimbrial protein, A chain precursor
Fimbrial protein pilin
Putative two-component response regulator andGGDEF family protein YeaJ
Putative two-component response regulator
Response regulator VieA
Sensory box sensor histidine kinase/responseregulator VieS
Mobile element protein
Transporter, LysE family
FIG00627057: hypothetical protein
putative transcriptional regulatory protein
Catalyzes the cleavage ofp-aminobenzoyl-glutamate to p-aminobenzoate andglutamate, subunit A
Threonine dehydratase (EC 4.3.1.19)
Beta-ureidopropionase (EC 3.5.1.6)
Leucine-responsive regulatory protein,regulator for leucine (or lrp) regulon and high-affinity branched-chain amino acid transport system
hypothetical protein
hypothetical protein
CBS domain-containing membrane protein
Mobile element protein
FIG074102: hypothetical protein
Nitric oxide reductase FlRd-NAD(+) reductase(EC 1.18.1.-)
Anaerobic nitric oxide reductaseflavorubredoxin
Functional role page for Anaerobic nitric oxidereductase transcription regulator NorR
Mobile element protein
Transcriptional regulator, LysR family
Alcohol dehydrogenase (EC 1.1.1.1)
Mobile element protein
hypothetical protein
hypothetical protein
Type IV secretory pathway, VirD2 component
hypothetical protein
possible site-specific recombinase
CoA-disulfide reductase (EC 1.8.1.14)

FIG. 15F

GENETICALLY ENGINEERED *VIBRIO* SP. AND USES THEREOF

CROSS-REFERENCE TO RELATED APPLICATIONS

This application is a divisional application of U.S. application Ser. No. 15/687,373 filed Aug. 25, 2017, now issued as U.S. Pat. No. 11,203,761; which claims the benefit under 35 USC § 119(e) to U.S. application Ser. No. 62/380,341, filed Aug. 26, 2016. The disclosure of each of the prior applications is considered part of and is incorporated by reference in the disclosure of this application.

INCORPORATION BY REFERENCE OF SEQUENCE LISTING

The material in the accompanying sequence listing is hereby incorporated by reference into this application. The accompanying sequence listing text file, named CODEX2050-2_ST25, was created on Nov. 19, 2021 and is 42,226 bytes in size. The file can be accessed using Microsoft Word on a computer that uses Windows OS.

BACKGROUND OF THE INVENTION

Field of the Invention

The present disclosure relates to genetically engineered *Vibrio* sp. bacteria and the use of such bacteria for the cloning, construction, maintenance, manipulation and/or propagation of DNA molecules and for the expression and harvesting of protein and peptide sequences.

Background Information

The biotechnology sector relies upon organisms such as *E. coli* as hosts for the generation of desired biomolecules (e.g., recombinant DNA, proteins, natural products, etc.) as well as for the study of biological processes and the development of bio-based technologies and products. While advances in fields such as genomics, synthetic biology, and genome/metabolic engineering have made possible projects at an unprecedented scale, the host organisms that the field relies upon have changed relatively little in decades and are proving to be inadequate or inefficient for many ambitious projects.

*E. coli* has been the main prokaryotic workhorse for several decades, being used ubiquitously in both academic and industrial efforts, and relied upon as a host for molecular cloning, protein expression, metabolic engineering, a source of cellular extracts for in vitro molecular biology, and as a chassis for synthetic biology efforts. The use of *E. coli* is due largely to its extensive characterization (having served as a model organism since the late 19th century), having a large collection of standardized tools and protocols, and being relatively easy to work with. *E. coli* is certainly not the only organism in use in biotechnology, as there are plenty of obscure organisms being utilized, usually to leverage some peculiar biological property that allows that organism to excel in some niche application, but *E. coli* is the most widely adopted and broadly applied bacterial species in biotechnology.

There is a need for more robust, faster growing, and easily genetically manipulated bacterial cells that can be used as host organisms, especially to produce products such as large recombinant DNA molecules, and as alternative hosts for protein expression.

SUMMARY OF THE INVENTION

The present disclosure provides engineered *Vibrio* sp. organisms. The organisms can have an altered Chromosome II that serves as a vector within *Vibrio* and other organisms, or for the cloning of nucleic acid molecules and for the expression and production of proteins and peptides in a *Vibrio* sp. organism. Chromosome I and/or Chromosome II can also be engineered to contain one or more genetic elements for the cloning and amplification of the chromosome. The genetic elements can enable the cell to express an exogenous or heterologous protein or peptide, which can also be secreted from the cell. The engineered organisms of the invention can also contain a nucleic acid construct comprising a signal sequence, which enables the cell to secrete an expressed protein or peptide. In some embodiments the organisms of the invention have been engineered to survive, propagate, and amplify at cold temperatures. The genetically engineered organisms are useful for the construction, maintenance, manipulation, and/or propagation of DNA constructs; protein or peptide expression and/or secretion; metabolic engineering; expression of cellular extracts for cell-free biology; and for synthetic biology applications. The disclosure also relates to the use of the replication machinery of *Vibrio* sp. on a cloning vector for cloning or replication of recombinant DNA constructs or for the expression and production of heterologous protein and peptides by the *Vibrio* sp. cell.

In a first aspect the present inventio provides a *Vibrio* sp. organism having a Chromosome I (ChI) comprising essential genetic elements and an altered Chromosome II (ChII) comprising at least one piece of exogenous DNA of greater than 10 kb in size that encodes at least one heterologous protein or peptide; and wherein the organism comprises all cellular components functional for the replication and amplification of the altered Chromosome II, and the altered Chromosome II is replicated during cellular growth of the organism. In one embodiment ChII of the organism comprises SEQ ID NO: 1 or a variant thereof. The at least one piece of heterologous DNA comprised on the altered ChII can be greater than 50 kb in size or greater than 100 kb or greater than 500 kb or greater than 1 Mb or greater than 2 Mb.

In some embodiments the altered ChII further encodes at least one origin of replication and at least one selection marker. The organism can have tetA/tetR or chloramphenicol resistance genes, an R6Kgamma origin of replication, and can also have an RP4 oriT region. In some embodiments at least one essential genetic element removed from ChII is comprised on ChI. The organism can be a *Vibrio* sp., which can be *Vibrio natriegens*.

In some embodiments the altered ChII has an inducible promoter, which optionally can be the IPTG inducible trc promoter, or the temperature inducible lambda pR promoter, or the arabinose inducible araBAD promoter.

In some embodiments ChI or ChII can have at least one deletion of a gene encoding a protein such as, for example, a recombinase, an endonuclease, a protease, and a restriction enzyme. The recombinase can be recA and the endonuclease can be Dns.

In another aspect the invention provides an organism having a DNA sequence that encodes a functional signal peptide operably linked to at least one heterologous protein or peptide. The heterologous protein or peptide can be expressed having the functional signal peptide so that the exogenous protein or peptide is secreted from the organism. The functional signal peptide can be any of SEQ ID Nos: 8-28 or a variant of any of them. The DNA sequence encoding the functional signal peptide operably linked to at least one exogenous protein or peptide can be comprised on a vector. The organism can be a *Vibrio* sp. organism.

In another aspect the invention provides a *Vibrio* sp. organism having an exogenous sequence encoding one or more enzymes from a reactive oxygen species detoxification system. In various embodiments the organism can have one or more alkyl hydroperoxide reductase gene(s) under the control of an exogenous promoter and operable in *Vibrio* sp., or a catalase gene under the control of an exogenous promoter and operable in *Vibrio* sp., or a glutathione S-transferase gene under the control of an exogenous promoter and operable in *Vibrio* sp., or any combination of them. In one embodiment the organism has the alkyl hydroperoxide reductase operon, which can be from *E. coli* (ahpCF). In another embodiment the organism has the catalase gene, which can be katG or katE. When the organism has the glutathione S-transferase gene it can be, in one embodiment, gstA. The reactive oxygen species detoxification system can be comprised on ChI or ChII. In some embodiments the organism can have an exogenous vector, and enzyme from the reactive oxygen species detoxification system can be comprised on the exogenous vector. In one embodiment the organism is comprised in a controlled environment at a temperature of about 4° C. or less. The organism can be comprised on a solid media. The organism having the enzyme from the reactive oxygen detoxification system can remain viable after cultivation at about 4° C. for at least 14 days, or can remain viable after cultivation at about 4° C. for at least 19 days.

In another aspect the invention provides a nucleic acid expression cassette encoding a. an inducible promoter operable in *Vibrio* sp.; b. a signal peptide functional to cause the secretion of an exogenous protein or peptide from the *Vibrio* sp. cell; c. an heterologous nucleic acid sequence; wherein the promoter, signal peptide, and heterologous nucleic acid sequence are operably linked for the expression and secretion of a protein or peptide encoded by the heterologous nucleic acid sequence from the *Vibrio* sp. cell. The promoter can be an inducible promoter, e.g. inducible with sucrose. In various embodiments the signal peptide can be any disclosed herein.

In another aspect the invention provides a nucleic acid shuttle vector containing a) a *Vibrio* sp. sequence of Chromosome II replication machinery; b) an origin of replication active in *Vibrio* sp.; c) an origin of replication active in a non-*Vibrio* organism; d) a selection marker; e) a gene of interest. In some embodiments the non-*Vibrio* organism is *E. coli*.

In another aspect the invention provides a *Vibrio* sp. organism containing a. a Chromosome I comprising a heterologous nucleic acid construct having a sequence for an inducible RNA polymerase, b. where the RNA polymerase is functionally active upon induction with an activator to activate a promoter operably linked to a heterologous nucleic acid on an extra-chromosomal DNA; and c. where the organism is a competent organism. The organism can have a Dns deletion and optionally a selectable marker.

In another aspect the invention provides a method of transforming a *Vibrio* sp. cell by a. providing a competent *Vibrio* sp. organism having a Chromosome I that comprises a heterologous sequence encoding an inducible RNA poly merase; b. introducing an extra-chromosomal DNA comprising a promoter operably linked to a heterologous nucleic acid on an extra-chromosomal DNA, wherein the promoter is activated by the RNA polymerase of a). The method can further comprise inducing the RNA polymerase of a). In some embodiments the method involves expressing the heterologous nucleic acid on the extra-chromosomal DNA to produce at least one protein.

The use of sub-titles of section headings herein is for ease of understanding the content of the application only and the subject matter under any specific heading or sub-heading is not to be construed as limited only to that described by the heading or sub-heading unless specifically indicated.

DESCRIPTION OF THE DRAWINGS

FIG. 1A. pBR322-trc-GFP; B. FIG. 1B. p15a-trc-GFP; FIG. 1C. pBR322-araBAD-GFP; FIG. D. p15a-araBAD-GFP; FIG. 1E. pBR322-cI857ts-GFP and FIG. 1F. p15a-cI857ts-GFP.

FIG. 8 A-B shows *V. natriegens* cultures comprising T7 RNA polymerase operably linked to the indicated inducible promoter and a GFP cassette operably linked to a T7 promoter in the indicated media. FIG. 8A) White light image of cultures. Two left most cultures are wild type strains not expressing GFP, while the other four cultures have a distinct yellow/green color, indicating expression of GFP.

FIG. 11 shows the 20 most abundant proteins identified in growth media containing sucrose from *Vibrio natriegens*.

FIG. 15A-15F. FIG. 15A-15B illustrate two chromosomes of *V. natriegens* strain E depicted with regions not present in *V. natriegens* strain A annotated in light red. An enlargement of three regions present in *V. natriegens* strain E, but absent from *V. natriegens* strain A are shown in the dashed blue boxes. Coding sequences are colored in yellow, genes associated with insertion sequences are colored in blue, genes annotated as associated with restriction/modification systems colored in pink, phage-related proteins shown in purple, and genes showing high similarity to proteins in the REBASE restriction enzyme database shown in dark red. FIGS. 15C-15F provides a list of genes that can be deleted. The organism of the invention can contain a deletion of any one or more of the genes listed in Table 15b and any combination of them.

DETAILED DESCRIPTION OF THE INVENTION

Figure 1A:
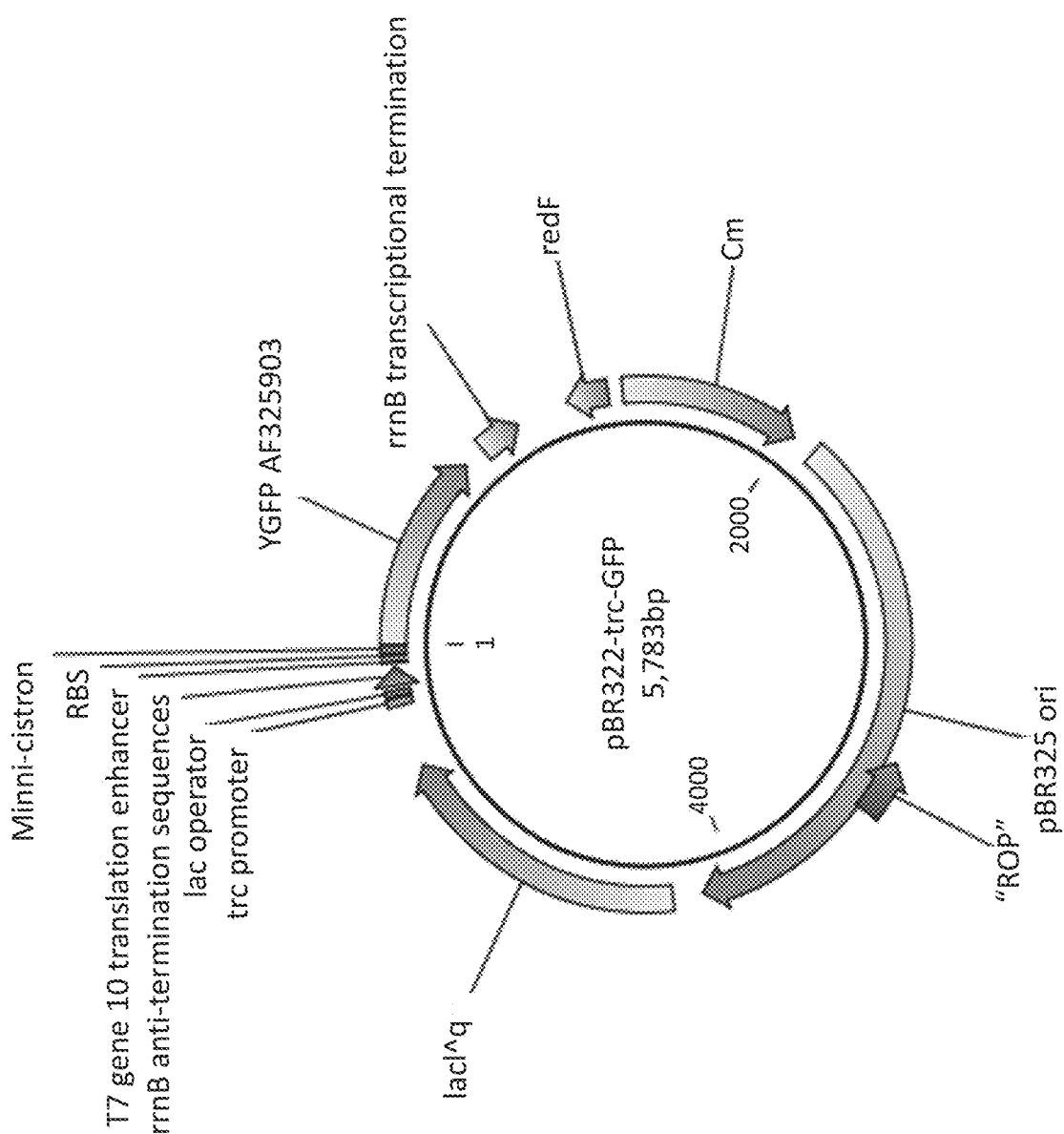
FIGS. 1A-F show the use of *V. natriegens* as a host for inducible protein expression. Six plasmids were designed for inducible protein expression of GFP.
Figure 1B:
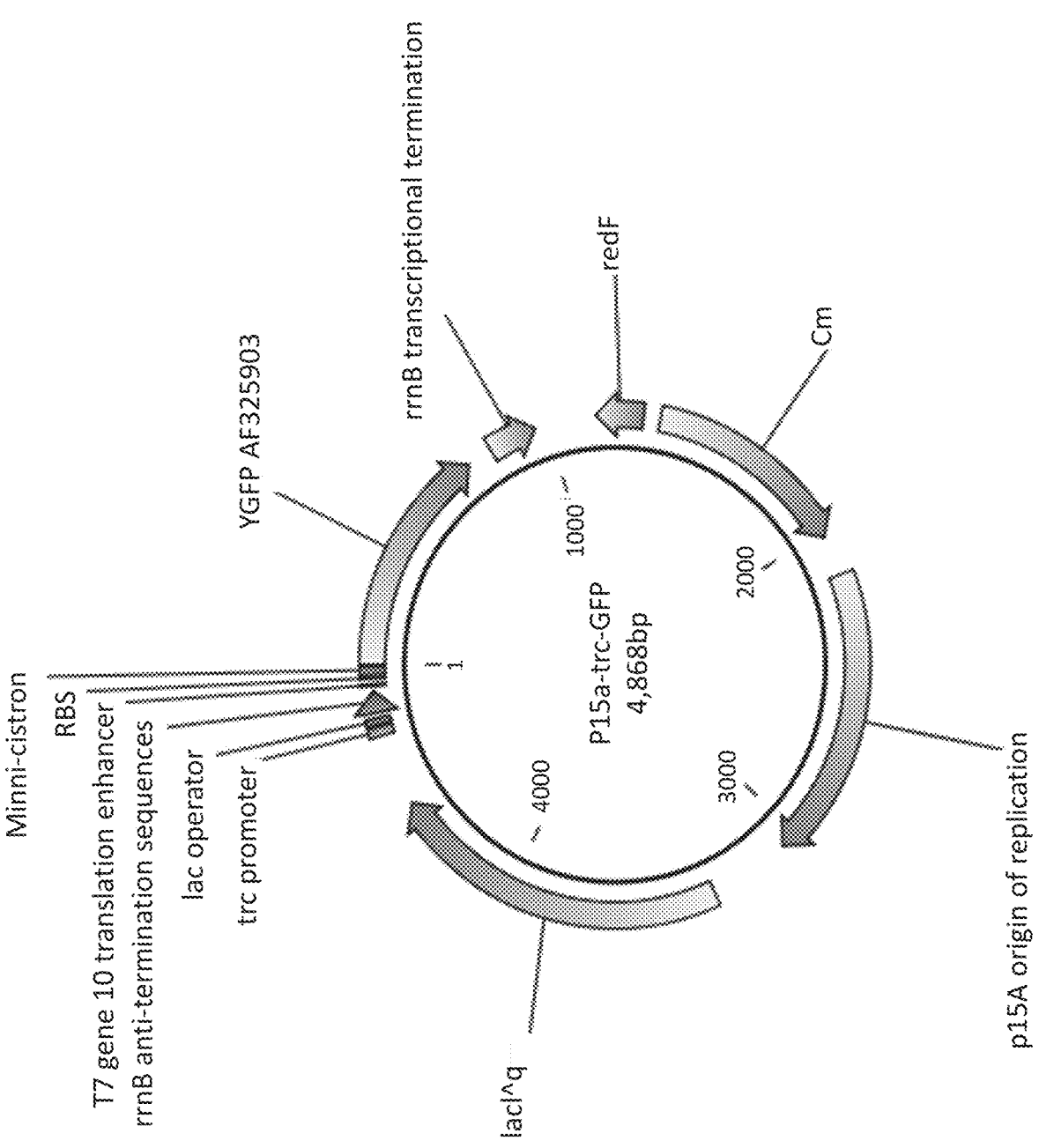
Figure 1C:
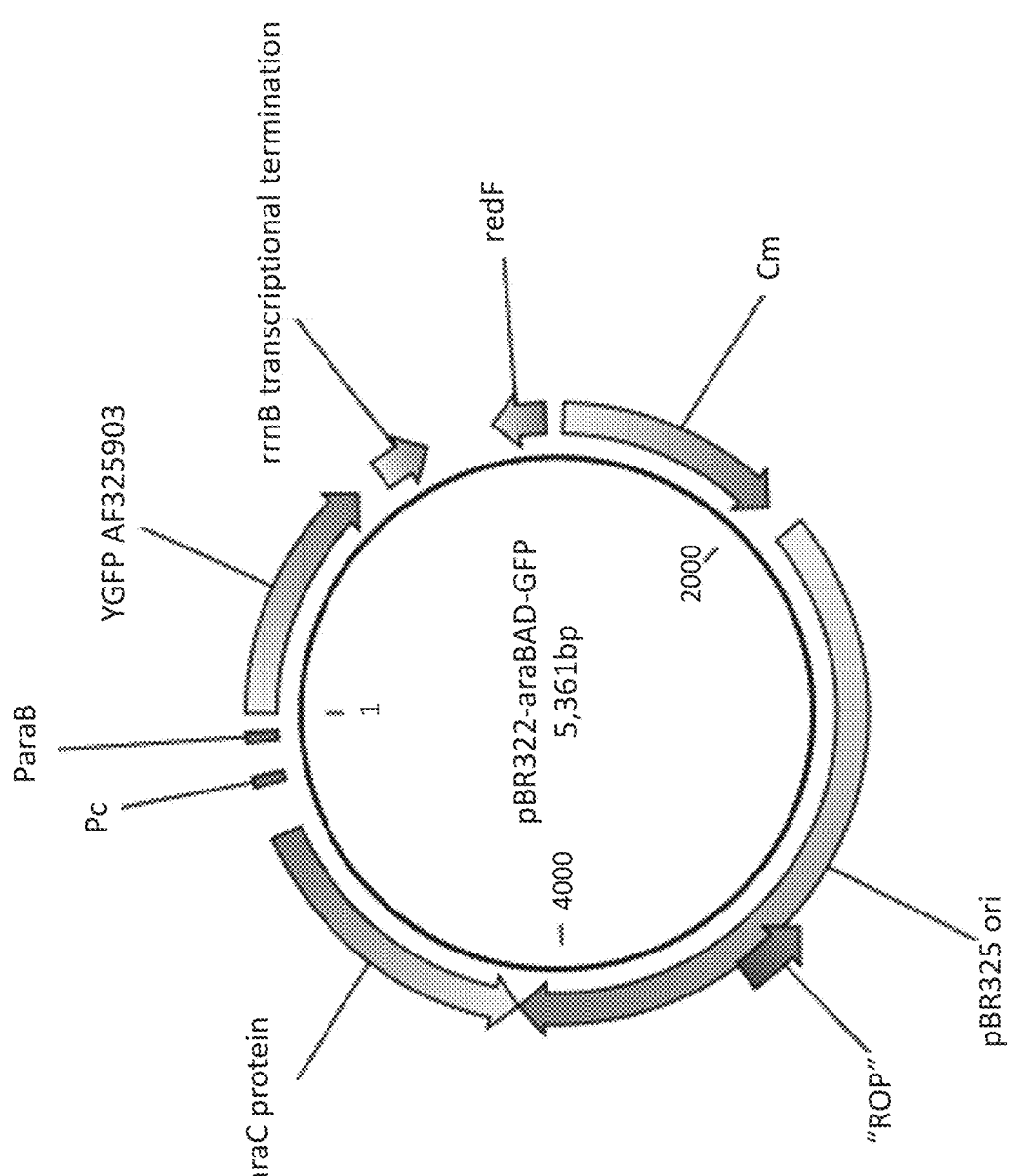
Figure 1D:
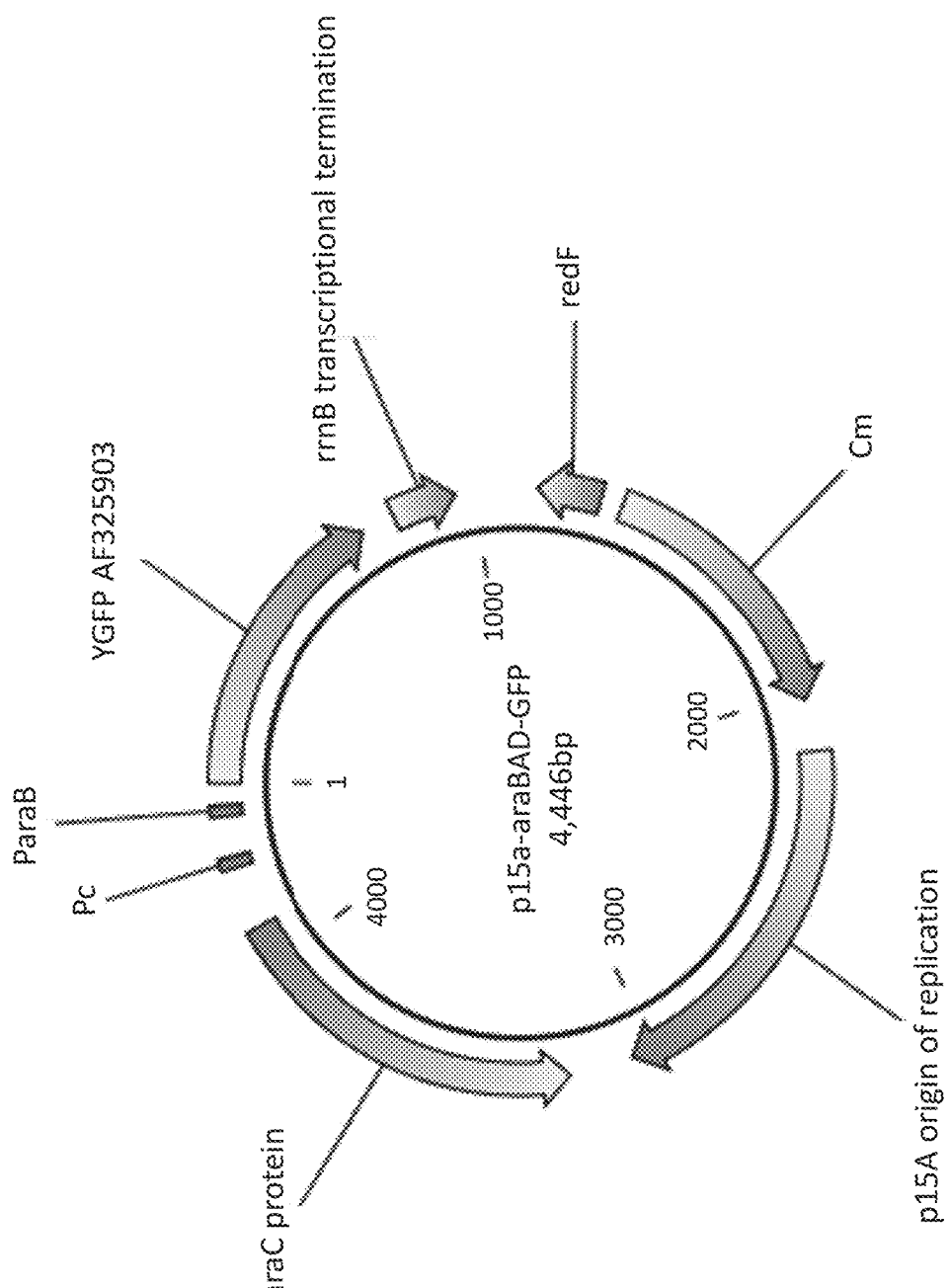
Figure 1E:
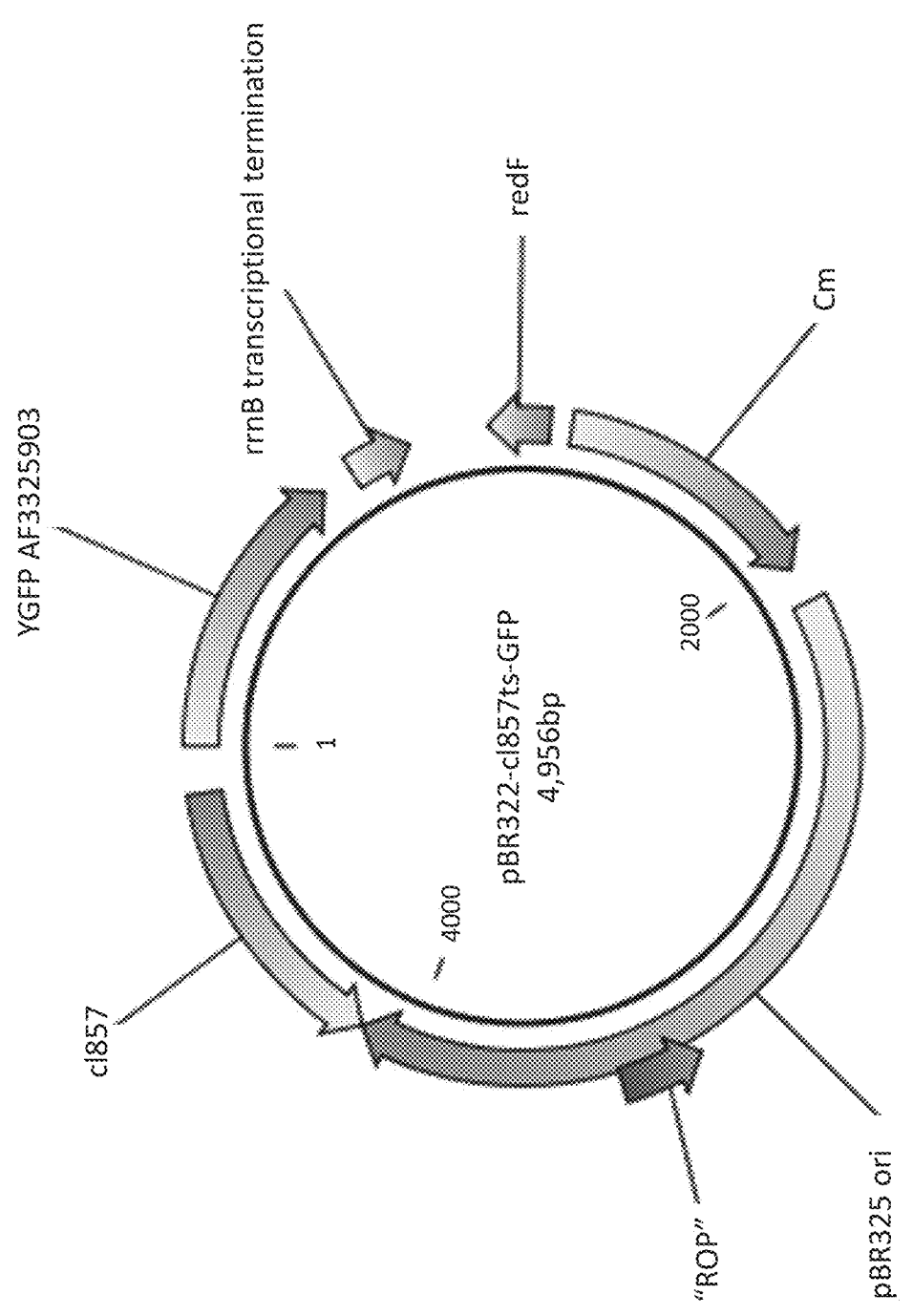
Figure 1F:
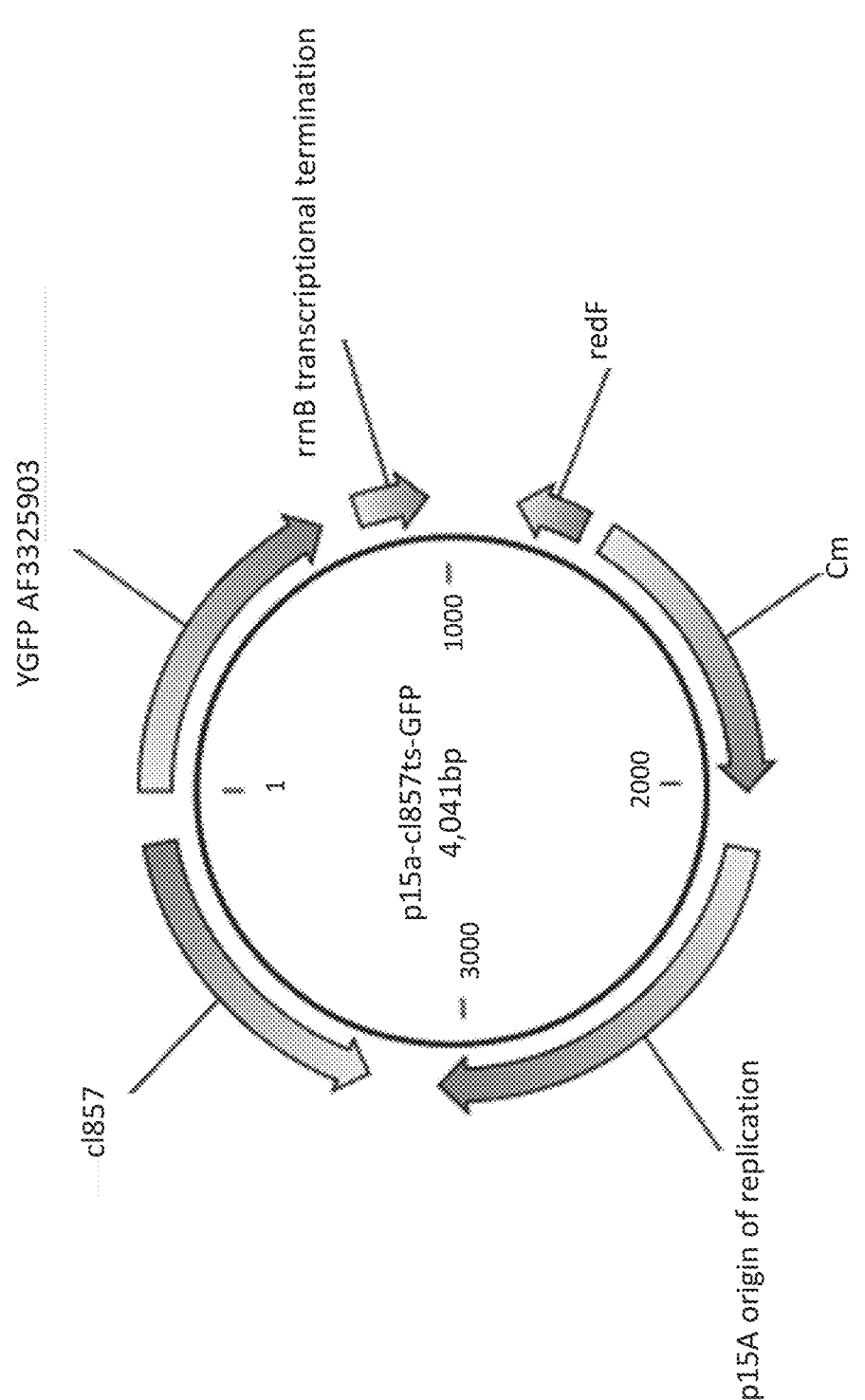

The invention provides engineered *Vibrio* sp. organisms. In some embodiments the organisms comprise a vector and are capable of cloning large sequences of DNA of greater than 10 kb or greater than 50 kb in size, or larger. In other embodiments the invention provides signal sequences for use in *Vibrio* sp. and other organisms and can be utilized for the secretion of a heterologous protein of interest. The signal sequences can achieve high secretion levels of desired heterologous proteins. In other embodiments the invention provides engineered *Vibrio* sp. organisms that can tolerate low temperatures on solid or semi-solid media and sustain viability or culturability of the cells after being stored at the low temperatures. The invention allows for the acceleration of various applications in molecular biology, synthetic biology, and metabolic engineering due to the rapid growth rate nutritional versatility of the organism.

*Vibrio* is a genus of Gram-negative, facultative anaerobic bacteria possessing a curved-rod shape, with *Vibrio* sp. indicating a species within the genus *Vibrio*. In some embodiments, *Vibrio* sp. can comprise any one or more of the following *Vibrio* species, and in all possible combinations: *adaptatus, aerogenes, aestivus, aestuarianus, agarivorans, albensis, alfacsensis, alginolyticus, anguillarum, areninigrae, artabrorum, atlanticus, atypicus, azureus, brasiliensis, bubulus, calviensis, campbellii, casei, chagasii, cholera, cincinnatiensis, coralliilyticus, crassostreae, cyclitrophicus, diabolicus, diazotrophicus, ezurae, fischeri, fluvialis, fortis, furnissii, gallicus, gazogenes, gigantis, halioticoli, harveyi, hepatarius, hippocampi, hispanicus, hollisae, ichthyoenteri, indicus, kanaloae, lentus, litoralis, logei, mediterranei, metschnikovii, mimicus, mytili, natriegens, navarrensis, neonates, neptunius, nereis, nigripulchritudo, ordalii, orientalis, pacinii, parahaemolyticus, pectenicida, penaeicida, pomeroyi, ponticus, proteolyticus, rotiferianus, ruber, rumoiensis, salmonicida, scophthalmi, splendidus, superstes, tapetis, tasmaniensis, tubiashii, vulrificus, wodanis,* and *xuii.* In some embodiments, *Vibrio* sp.

is *Vibrio natriegens*. In some embodiments, *Vibrio* sp. is not *Vibrio cholera*. In some embodiments, *Vibrio* sp. comprises all species of *Vibrio* other than cholera.

*Vibrio* sp. have several advantages as host cells over other bacteria for many molecular biology applications. One advantage is their rapid growth rate. One of the most time intensive steps in modern biotech workflows is waiting for the host cell to grow to a sufficient density before DNA/protein/product can be recovered or the phenotype can be assessed. Since dramatic time savings have been realized in other areas of biotech workflows (e.g., sequencing, bioinformatic analysis, high-throughput assays, etc.), growth of the host has become an even more significant bottleneck. *E. coli* is considered to have one of the quickest growth rates relative to other organisms used in the biotech sector, and this has been one of its strengths. Because *Vibrio* sp. have a growth rate 2-3× faster than commonly used *E. coli* strains, it is able to achieve a dramatic reduction in the time necessary for the host to grow, and will accelerate research efforts. In certain aspects of the present disclosure, the growth rate of *Vibrio* sp. in terms of doubling time expressed as numbers of cells in a population is about 10 minutes or about 12 minutes or about 13 minutes or about 14 minutes or about 15 minutes or about 16 minutes. In other aspects, the growth rate of a genetically engineered *Vibrio* sp. in terms of doubling time is 5-30 minutes.

Another advantage of *Vibrio* sp. is the size of heterologous DNA that can be harbored. Large scale genetic engineering or synthetic genome construction efforts require the assembly, manipulation, and maintenance of large pieces of recombinant DNA, tasks which are carried out in a genetically tractable host (such as *E. coli*) before delivery of the engineered DNA to the final host organism. Currently, most of this work is carried out in *E. coli*, but as projects become more ambitious, the limitations of this species are becoming apparent. It has been observed that with current technologies, *E. coli* is capable of harboring exogenous DNA constructs of no more than 500 kb (and in some cases much less depending on the properties of the DNA being cloned) on a bacterial artificial chromosome, which is a serious limitation for synthetic genome/large pathway construction efforts. This has necessitated the development of novel hosts as cloning platforms such as *Saccharomyces cerevisiae* and *Bacillus subtilis*. While these hosts have the advantage of being able to take up and stably propagate large (Mb-sized) fragments of heterologous DNA, they have their own disadvantages, with *Saccharomyces cerevisiae* growing much slower than *E. coli* (~3× slower), and both species being incompatible with standard laboratory techniques and being very difficult to recover DNA from.

An additional advantage is the compatibility of *Vibrio* sp. with standard lab protocols. Unlike organisms that require specialized techniques or methods, *Vibrio* sp. is compatible with many standard cloning vectors, growth media, workflows and commercially-available kits developed for *E. coli* or recovering DNA.

A further advantage is the nutritional versatility of *Vibrio* sp. allowing it to grow on a range of different growth media, including inexpensive, minimal media. Coupled with its rapid growth rate, this feature allows for industrial scale production in less time and at lower cost.

Chromosomes I and II

The two chromosomes of the genus *Vibrio* are designated as Chromosome I (ChI) and Chromosome II (ChII). Chromosome I in the natural state is typically from 3.0-3.3 Mb and Chromosome II in the natural state from 0.8-2.4 Mb but the particular numbers depend on the species of *Vibrio*.

Some embodiments of the invention comprise a *Vibrio* sp. having an altered Chromosome I and/or an altered Chromosome II.

In one embodiment the *Vibrio* host cell of the invention has an altered Chromosome II that has had non-essential genetic elements deleted (and which can be relocated to Chromosome I or extrachromosomal DNA), thus freeing Chromosome II for use as a vector. There can be a copy of each essential genetic element on at least one of ChI or ChII, or extrachromosomal DNA.

Alterations

An "altered" chromosome is one that contains one or more of an insertion, deletion, substitution, rearrangement, inversion, or other genetic manipulation through human efforts and relative to the natural chromosome as found in Nature and unmodified by human activity. A substitution can also include the optimization of an existing gene. A deleted genetic element can also be relocated from ChII to ChI, or vice versa, or to extrachromosomal DNA. Thus, ChI can also be altered.

These alterations can be performed in any appropriate manner, e.g., by using insertion cassettes, or enzymatically through the use of a recombinase such as, for example, Cre-loxP system or Cre recombinase. The Cre recombinase can utilize known lox sites compatible with Cre recombinase (e.g., lox66 and lox71 sites). In other embodiments the alteration can be performed through the action of a nuclease such as, for example, Type II CRISPR Cas9. The alterations can also be performed with a homologous recombination vector or insertion cassette containing regions of sequence homology to a region in the genome where an insertion or deletion is desired. The homologous recombination vector can be incorporated by a single cross-over event or a double cross-over event. The alteration can also be performed through use of an integrase, such as, for example, PhiC31 or bxb1, or through the use of a suicide vector. In some examples the vector is assembled in vitro and subsequently transformed and amplified in *E. coli*. In some examples the vector is assembled in *S. cerevisiae*. In some examples, the amplified vector is introduced into the *Vibrio* sp. organism by conjugation, electroporation, chemical competence, biolistics, transduction, or via natural competence. Transformation of cells with any construct described herein can be performed by any suitable method, for example bacterial conjugation, electroporation, or chemical transformation.

In various embodiments of the organisms of the invention, in either of ChI, ChII, or the genome as a whole can be minimized, meaning one or more (or all) non-essential genetic elements (e.g. genes or other nucleic acid sequences) have been deleted, moved to the other chromosome or to extrachromosomal DNA, or otherwise removed to a substantial extent. For example a minimized chromosome can be reduced in size by at least 2.5% or at least 5.0% or at least 10% or at least 15% or at least 20% or at least 25% or at least 30% or at least 35% or at least 40% or at least 45% or at least 50%.

Genes are the basic unit of an inheritable trait in bacteria. Some genes can be further divided into regulatory elements, such as promoter/operators that regulate expression of the gene, and structural elements that comprise the coding portion. A genetic element refers to defined segments of DNA comprised in a cell's genome that perform a biological function within a cell. They can be naturally present or synthetic elements (added by human efforts). In some embodiments where *Vibrio* sp. is the host cell the genetic element is present on ChI or ChII and is not extrachromosomal DNA. Genetic elements can perform or support cellular functions, or encode proteins or peptides, or perform regulatory functions, bind ribosomes, or repair functions for nucleic acid sequences and can be part of the cellular machinery and/or replication machinery of the cell. Examples of genetic elements include, but are not limited to, a coding or non-coding gene, any sub-portion of a gene, a methyl-transferase encoding gene (e.g., Dam), a promoter, a termination sequence, a regulatory element, a 5' or 3' untranslated region, operators, a repeat, a control element, a protein or nucleic acid or ribosomal binding site, a transposon, or a structural "coding" portion of a gene, an initiation sequence (including, but not limited, to DnaA or RctB), multiple cloning sites, origins of transfer, conjugation or replication. In various embodiments a genetic element is involved in transcription, translation, recombination, the binding of a regulatory protein, the rate of transcription of a gene, or is a regulatory element. A "coding sequence" or "coding portion" refers to the portion of an mRNA or DNA molecule that codes for a polypeptide. It typically consists of the nucleotide residues of the molecule which are matched with an anticodon region of a transfer RNA molecule during translation of the mRNA molecule or which encode a stop codon. The coding sequence may include nucleotide residues corresponding to amino acid residues which are not present in the mature protein encoded by the mRNA molecule (e.g., amino acid residues in a protein export signal sequence).

An essential genetic element is one that, if not functionally present in the cell, results in the inability of the cell to replicate, survive, or maintain homeostasis in a specific environment in a substantially normal way. Some genetic elements are always essential, and some are only essential in a specific environment. Essential elements can be, but are not limited to, those required for a function such as basic metabolism needed for a cell to maintain homeostasis, DNA replication, transcription and/or translation of essential genes, proteins and peptides, functions necessary to maintain cellular structures, transport processes of essential materials into or out of the cell, or any combination thereof. Even essential genes or genetic elements can be deleted from ChII if moved to ChI or provided in trans.

Non-essential genetic elements can be identified experimentally, for example by using bioinformatics. Multiple wild types of *Vibrio* strain genomes can be evaluated and one can identify genes or nucleic acid sequences that are not consistently present in all strains. In other methods identification of non-essential genes can be achieved by transposon bombardment or other insertional mutagenesis screens that will produce multiple random integration mutants, and sequencing the genes disrupted in these viable mutants. Non-essential genes can also be sequentially removed by using homologous recombination. In some embodiments all essential genetic elements are comprised on Chromosome I or altered Chromosome II or extrachromosomal DNA. In another embodiment all essential elements are comprised on Chromosome I and no essential elements are comprised on Chromosome II or on extrachromosomal DNA. Non-limiting examples of non-essential genetic elements that can be deleted only from ChII or entirely from the organism include exonucleases, endonucleases, methylases, nucleases (e.g. Dns), restriction enzymes, partial or complete restriction-modification systems, mobile elements, phage proteins, a recombinase (e.g. recA), an endonuclease, a protease, a restriction enzyme, or any combination thereof. The non-essential genetic elements can be entirely deleted. In some embodiments all methylases can be deleted except for DAM methylases, which are required for chromosome replication.

Figure 15A:
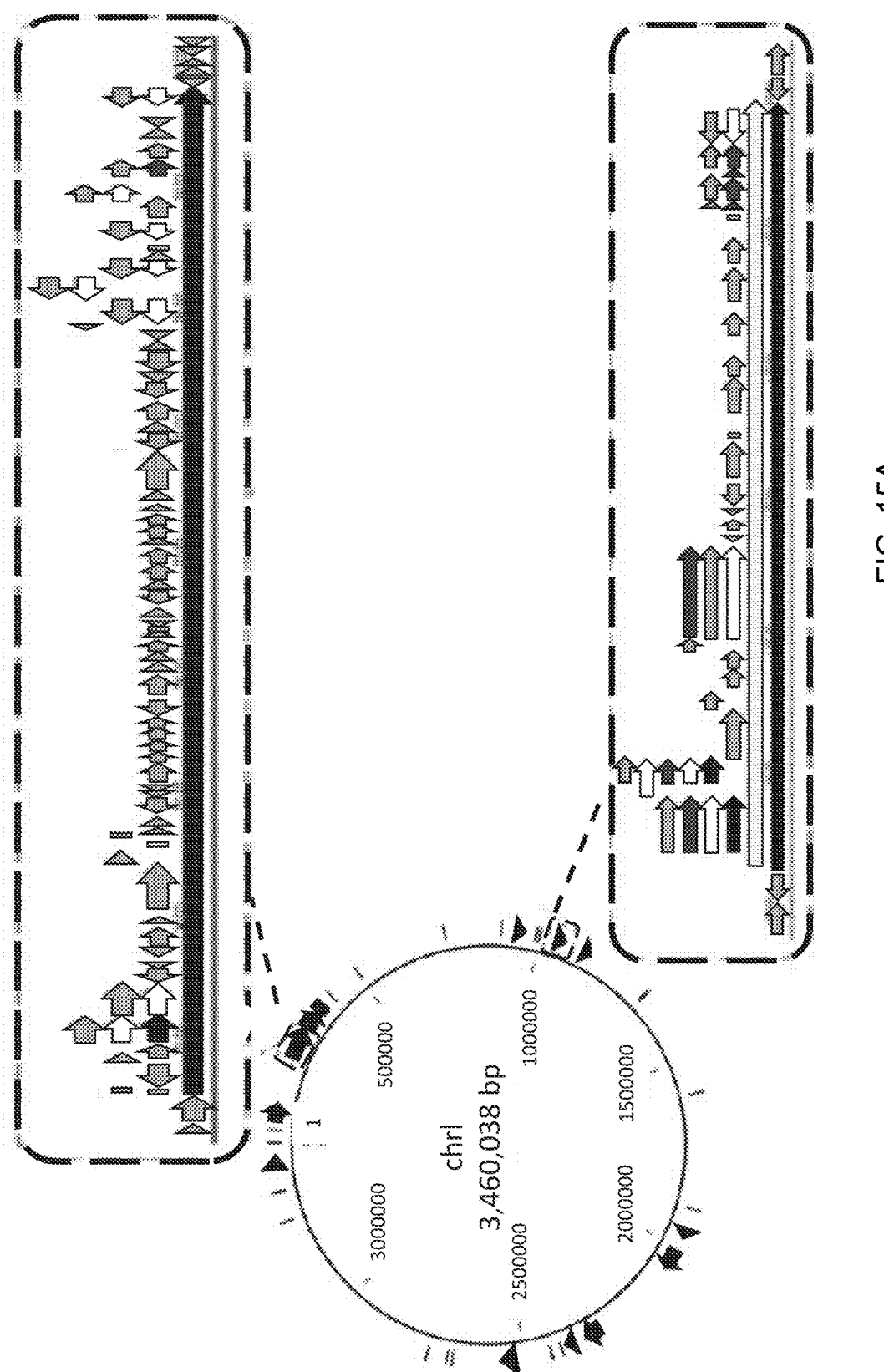
Figure 15B:
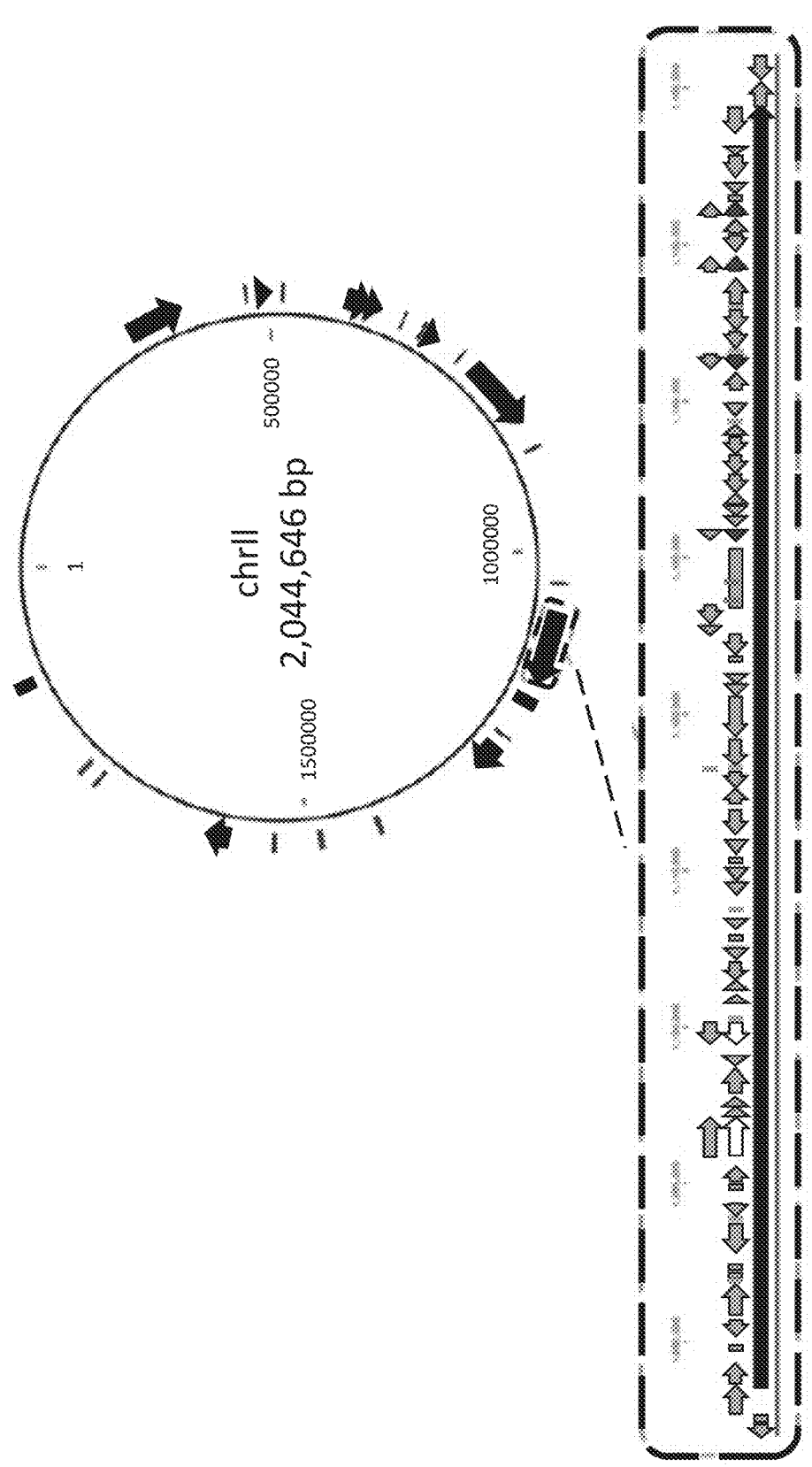

Additional genetic elements that can be deleted are also provides in FIG. 15. In a particular embodiment recA is deleted from ChI and/or the endonuclease Dns is deleted from ChI, where they are naturally present. In some embodiments all non-essential elements have been removed or deleted from ChI and ChII, but in other embodiments only most of the non-essential elements present on the natural chromosome have been removed or deleted from ChI and/or ChII.

Any of the organisms of the invention can comprise a deletion (or "knock out") of certain genes or genetic elements. In some embodiments the organism has a deletion or knock out of a gene encoding endotoxin or of a regulatory element necessary for the transcription of endotoxin.

ChII-Based Vector

A problem encountered with cloning large pieces of DNA in an organism is that the total DNA load in the organism becomes too large and the organism cannot efficiently replicate or even survive with the amount of total cellular DNA. The present invention therefore deletes many or all non-essential or otherwise unnecessary genetic elements from a cell.

In some embodiments the engineered organisms of the invention have a ChI containing essential genetic elements, an altered ChII that is missing or has deleted at least one genetic element compared to natural ChII. In various embodiments the total size of the at least one genetic element(s) deleted or missing from the altered ChII are at least 10 kb or at least or at least 50 kb, or at least 100 kb, or at least 200 kb, or at least 300 kb, or at least 500 kb, or at least 700 kb, or at least 1 Mb or 10-50 kb or 10-100 kb or 10-200 kb or 10-300 kb or 50-100 kb or 50-200 kb or 50-300 kb or 50-500 kb or 50 kb-1 Mb or more than 1 Mb or more than 1.5 Mb or more than 2 Mb or the entire ChII. Missing or deleted elements can be moved to ChI or to extrachromosomal DNA. The then available "free" space ChII can be leveraged as a nucleic acid construct as a cloning vector, expression vector, shuttle vector, plasmid, cosmid, or artificial chromosome The ChI and altered ChII together can have all essential elements of *Vibrio* sp., and the engineered organism can have all cellular and replication machinery necessary and functional for the cloning, replication and amplification of the heterologous DNA and altered ChII. During cell division or cellular growth, the exogenous DNA and altered ChII is therefore replicated and amplified. Cellular machinery refers to the physical and chemical components of a cell that function together to perform the physiological functions of the cell. In various embodiments the altered ChII can have less than 1.8 Mb or less than 1.6 Mb or less than 1.5 Mb or less than 1.3 Mb or less than 1.2 Mb or less than 1.0 Mb or less than 0.8 Mb of sequences present in the natural, unmodified ChII. The altered ChII can also have more than 2% or more than 3% or more than 5% or more than 10% or more than 25% or more than 50% or more than 75% of the sequences naturally present moved or deleted from ChII. These natural sequences that remain can be those that are naturally present in the organism and that function normally in the unmodified organism to conduct the physiological and other activities of the cell.

Thus, with nonessential elements deleted from ChII it can serve as a vector or plasmid or artificial chromosome carrying exogenous or heterologous DNA, for cloning, expression, or other purposes described herein. The heterologous or exogenous DNA comprised in ChII (or ChI) can comprise the sequence of a gene or other sequences, and can have a size of at least 10 kb, or at least 50 kb, or at least 100 kb, or at least 200 kb, or at least 300 kb, or at least 400 kb, or at least 500 kb, or at least 600 kb, or at least 700 kb, or at least 800 kb, or at least 900 kb, or at least 1 Mb, or at least 2 Mb, or 10 kb-200 kb, or 10 kb-300 kb, or 10 kb-500 kb, or 500 kb-1 Mb, or 300 kb-800 kb, or 10 kb-2 Mb, or 10 kb-1 Mb, or 10 kb-2 Mb, or 50 kb-500 kb, or 50 kb-1 Mb, or 50 kb-2 Mb, or 100 kb-1 Mb, or 100 kb-2 Mb, or 500 kb-1 Mb, or 500 kb-2 Mb, or 10 kb-3 Mb, or 50 kb-3 Mb, or 100 kb-3 Mb, or 500 kb-3 Mb. In some embodiments the heterologous or exogenous DNA will be a fragment of DNA that is a portion of a chromosome, or that expresses a protein of interest or other fragment of DNA that is to be cloned, amplified, or propagated.

In some embodiments an altered ChII can serve as a vector or plasmid or artificial chromosome having the exogenous or heterologous DNA and for the construction, cloning, maintenance, and/or recovery of large DNAs and for the expression, production, and secretion of proteins or peptides. The altered ChII can have genetic elements necessary for these function, including, for example, promoters, regulatory sequences, and/or signal sequences. In some embodiments the organism does not contain any extrachromosomal DNA. In some embodiments the organism does not contain any other exogenous or heterologous DNA other than that comprised on the altered ChII. But in other embodiments it can contain extra-chromosomal DNA as a natural plasmid and/or an optional exogenous plasmid, cosmid, artificial chromosome or an optional other vector. A natural plasmid or vector is one found in *Vibrio* sp. in any of the organism's natural environments and not present due to human efforts to place it there.

In some embodiments a plasmid, vector, or artificial chromosome of the invention comprising the DNA insert or essential genetic elements can be replicated and maintained in the host organism, which can be a *Vibrio* sp., an *E. coli*, a *Bacillus subtilis*, or a yeast.

"Exogenous nucleic acid molecule" or "exogenous gene" refers to a nucleic acid molecule or gene that has been introduced ("transformed") into a cell. A transformed cell may be referred to as a recombinant cell or an engineered cell. A nucleic acid molecule is also exogenous if it is present in a descendent cell and received from an ultimate parent cell where that nucleic acid molecule was exogenous nucleic acid. The exogenous gene may be from a different species (thus also "heterologous"), or from the same species (thus "homologous"), relative to the cell being transformed.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. Heterologous molecules are therefore always also exogenous, but exogenous molecules are not necessarily always heterologous. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

The altered Chromosome II can also comprise sequences of the natural Chromosome II. For example, it can contain a sequence of the replication machinery of the natural Chromosome II of *Vibrio* sp. The term "chromosomal replication machinery" or "replication machinery" refer to that part of an organism's chromosome which supports replication within the organism or in a different organism, and the replication machinery components can function together to perform the replication functions of the cell. In some embodiments replication machinery refers a 5.5 kb sequence from chromosome II of *V. natriegens* which is capable of supporting replication in an organism. In certain aspects, the replication machinery from *V. natriegens* can support replication in *V. natriegens* and *E. coli*. In some embodiments the sequence of replication machinery can have SEQ ID NO: 1 or a functional portion of SEQ ID NO: 1 or a variant of either. In some embodiments the SEQ ID NO: 1 can be operably linked to an exogenous nucleic acid sequence, which can also be heterologous. As used herein a "variant" of a nucleic acid or polypeptide sequence means having a sequence identity to a reference sequence (e.g. any of SEQ ID NO: 1-28) of at least 70% or at least 80% or at least 90% (and optionally less than 100%) or at least 95% (and optionally less than 100%) or at least 97% (and optionally less than 100%) or at least 98% (and optionally less than 100%) or at least 99% (and optionally less than 100%) or 90-99% or 90-95% or 95-99% or 97-99%. In other embodiments the variant has a sequence identity of at least 70% or at least 80% or at least 90% or at least 95% or at least 97% or at least 98% or at least 99% or 90-99% or 95-99% or 97-99% to a sequence of at least 10 or at least 15 or at least 20 or at least 30 or at least 40 or at least 50 or at least 100 or at least 200 or at least 300 or at least 400 or at least 500 or at least 600 or at least 700 or at least 800 or at least 900 or at least 1000 consecutive nucleotides or amino acids from the reference sequence (e.g. SEQ ID NO: 1-28). The invention also provides a genetically engineered nucleic acid molecule comprising any of SEQ ID NO: 1-28 or a variant of any of them. The nucleic acid molecule can also have an exogenous or heterologous sequence(s) on the 5' and/or 3' end, which exogenous or heterologous 5' and 3' sequence(s) can be compatible for cloning the nucleic acid molecule into a target vector (e.g., by homologous recombination).

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc.*

*Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A BESTFIT® comparison between sequences, available in the GCG package version 10.0, can use DNA parameters GAP=50 (gap creation penalty) and LEN=3 (gap extension penalty), and the equivalent settings in protein comparisons can be GAP=8 and LEN=2. When referring to the polypeptide or nucleic acid sequences of the present disclosure, included are sequences considered to be derived from the original sequence, which have sequence identities of at least 40%, at least 45%, at least 50%, at least 55%, of at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% or 90-99% or 95-99% or 97-99% or 98-99% sequence identity with the full-length polypeptide or nucleic acid sequence, or to fragments thereof comprising a consecutive sequence of at least 100, at least 125, at least 150 or more amino acid residues of the entire protein, or at least 100 or at least 200 or at least 300 or at least 400 or at least 500 or at least 600 or at least 700 or at least 800 or at least 900 or at least 1000 consecutive nucleotides; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms. (Schulz (1979) Principles of Protein Structure, Springer-Verlag). According to such analyses, groups of amino acids can be defined where amino acids within a group exchange preferentially with each other, and therefore resemble each other most in their impact on the overall protein structure. (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In some examples, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

In various embodiments the altered ChII can also comprise an origin of replication operable in *Vibrio* sp. (e.g. R6Kγ or another) for the replication of DNA, and optionally a pir gene sequence or variant thereof encoding π (pi) protein or a variant thereof. The π (pi) protein or a variant thereof can also be provided in trans (e.g. on extrachromosomal DNA) when advantageous. The altered ChII can also comprise any one or more of suitable resistance genes such as an antibiotic (e.g. tetA/tetR, chloramphenicol) or another suitable marker, and/or one or more origin(s) of transfer (e.g., oriT from RP4, oriV, or other suitable origins of transfer), which can be used to facilitate mobilization of the vector via conjugation, or one or more multiple cloning sites with restriction enzyme cut sites; ARS/CEN sequences for replication in yeast, and a yeast selection marker (e.g. Trp gene or another suitable yeast selection marker). The vector can also, optionally, contain a copy control sequence. The vector can be transferred between *Vibrio* sp. and other species, for example between *Vibrio* sp. and *E. coli* or between *Vibrio* sp. and *Bacillus subtilis* or *Vibrio* sp. and yeast (e.g. *Saccharomyces cerevisiae*) or other species in either direction. Transfer can occur through bacterial conjugation or other suitable methods. The vector can also be transformed into *Vibrio* sp., *E. coli, Bacillus subtilis*, or *Saccharomyces cerevisiae* cells by electroporation or by chemical transformation methods. Among other uses, the vector is useful in methods for cloning large DNA molecules in any of the aforementioned cells.

In addition to an origin of replication and a selection marker, ChI or ChII can also optionally have any one or more of an origin of transfer, a counter selection marker, a reporter gene, a regulatory element, an enzyme gene, or any combination of these. An origin of replication can be utilized from a variety of sources. In some embodiments the origin of replication is from the plasmid R6K. The gamma origin of replication from R6K (e.g., R6Kγ) can be utilized, but other origins of replication can also be utilized from other sources. When R6Kγ is the origin of replication it can be utilized with or without the pir gene encoding the pi (π) protein, which is necessary for plasmid replication. In other embodiments some or all of these elements can instead be provided on extrachromosomal DNA (e.g., a plasmid).

Selection markers can be utilized on the altered Chromosome II or on extrachromosomal DNA or any constructs described herein. In some embodiments the selection marker is a resistance gene, for example a gene conferring resistance to tetracycline, chloramphenicol, ampicillin, bleomycin, carbenicillin, gentamycin, glyphosate, hygromycin, kanamycin, neomycin, nourseothricin, phleomycin, puromycin, spectinomycin, streptomycin, or another antibiotic agent. In one embodiment the resistance gene is tetA/tetR. The resistance gene can also have an origin of replication from various sources, but in one embodiment is the RP4 oriT (which can be found on plasmid pJB3Tc20). The selection marker can also be ccdB.

In embodiments having a reporter gene, it can be a fluorescent protein or beta-galactosidase. In embodiments having an enzyme gene, it can be a recombinase, integrase, nuclease, recombineering enzymes, or polymerase. The recombinase can be Cre recombinase, the integrase can be PhiC31 or bxb1. The nuclease can be a Type II CRISPR Cas9 nuclease, and the polymerase can be a Sp6, T3, or T7 RNA polymerase. In some aspects, the vector is compatible with *E. coli, V. natriegens*, and/or *S. cerevisiae*.

Extra-chromosomal DNA (e.g. a plasmid) can be transformed into a cell by any suitable method, for example by bacterial conjugation (e.g. *E. coli* to *Vibrio* sp.), electroporation of electro-competent cells, chemical transformation into chemically competent cells, biolistics, transduction, or via natural competence. Efficiencies of transformation can be, for example, at least $1 \times 10^5$ or at least at least $1 \times 10^6$ at least $1 \times 10^7$ at least $1 \times 10^8$ cfu/ug DNA using any of the methods above.

Inducible Constructs

In some embodiments the *Vibrio* sp. organism of the invention has an inducible construct (e.g., a gene) engineered into ChI or ChII. The organism can also have a plasmid or other vector that has a nucleic acid sequence encoding an exogenous protein under the control of a promoter that is induced by the product of the inducible gene at ChI or ChII. Thus, when the inducer is provided to the cell transcription is initiated at the inducible gene, which produces a product that further induces transcription of the gene on the plasmid. In these embodiments the inducible gene can be any described herein and the promoter on the ChI or ChII can be any inducible promoter described herein. Also, the promoter on the plasmid or other vector can be any induced by the product of the inducible gene on ChI or ChII.

Inducible promoters used on any constructs described herein can include, but are not limited to, lacUV2 or lacUV5 promoter (which can be arabinose-inducible), a trc promoter (which is optionally regulated by lacI and can be arabinose inducible), the araBAD promoter (which can be regulated by araC and arabinose inducible), the phase lambda pR promoter (which can be regulated by cI857 and be temperature inducible).

In some embodiments the construct is a plasmid and contains a gene of interest under the control of either an arabinose-inducible, IPTG-inducible, or temperature-inducible promoter (araBAD, trc, and pR promoter (controlled by cI857ts), respectively) and can be replicated either by the pBR322 or p15a replication origins.

In some aspects, the genetically engineered *Vibrio* sp. of the invention further comprises a nucleic acid cassette having a heterologous nucleic acid sequence operably linked to a promoter, which can be a natural or a heterologous promoter. The heterologous promoter can be an inducible promoter, inducible by temperature, an aldopentose (e.g. arabinose) or IPTG, as non-limiting examples. In some examples the heterologous nucleic acid encodes T7 RNA polymerase.

In some aspects, the present invention provides a vector comprising *Vibrio* sp. chromosomal replication machinery. The replication machinery can contain any of the sequences described herein, e.g. SEQ ID NO: 1 or a variant thereof. In some examples, the vector also comprises a heterologous nucleic acid of interest. The vector can also have an inducible promoter operably linked to the nucleic acid of interest. In some embodiments the vector can be replicated in *Vibrio* sp., *E. coli* or *S. cerevisiae*. The invention also provides host cells, which can be any cell described herein. The host cells can comprise any nucleic acid or vector or expression cassette as described herein.

As used herein, "operably linked" is intended to mean a functional linkage between two or more sequences such that activity at or on one sequence affects activity at or on the other sequence(s). For example, an operable linkage between a polynucleotide of interest and a regulatory sequence (e.g., a promoter) is a functional link that allows for expression of the polynucleotide of interest. The term therefore refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site. Operably linked elements may be contiguous or non-contiguous. When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest. "Juxtaposed with" in the context of nucleic acid sequences, means the referenced sequences are part of the same continuous nucleic acid molecule.

Any of the organisms described herein can have a Chromosome I that contains a sequence encoding an inducible gene (e.g., T7 RNA polymerase or another inducible gene) although a non-inducible T7 RNA polymerase can also be used. The organism can also have an extra-chromosomal DNA that also has an inducible gene thereon that is transcribed when induced by the product of the inducible gene on ChI. Thus in one embodiment the extra-chromosomal DNA can have a T7 promoter or other suitable promoter recognized by T7 RNA polymerase (e.g. T3 or SP6) in front of a gene of interest. The extra-chromosomal DNA can be an RK2 plasmid containing an RK2 replicon, or can be any described herein. Using such a design the gene of interest can be transcribed (and translated) upon the production of T7 RNA polymerase or other inducible gene product from ChI. The inducible gene on ChI can be induced by any suitable molecule, as described herein. Therefore, under this design an extra-chromosomal DNA can be provided to a *Vibrio* cell that has an inducible gene on ChI. Upon being stimulated with the inducing molecule transcription occurs at the inducible gene. The product of the inducible gene triggers the promoter on the extra-chromosomal DNA and the exogenous DNA thereon is thus transcribed, producing the product of the gene of interest.

Signal Peptides

The engineered or recombinant *Vibrio* sp. of the invention can comprise an altered ChII or a plasmid, cosmid, artificial chromosome, or other vector that contains an exogenous or heterologous nucleic acid sequence that encodes an exogenous or heterologous protein or peptide, and a nucleic acid sequence encoding one or more functional *Vibrio* sp. signal peptides. The sequence encoding the functional signal peptide can be operably linked to the sequence encoding the protein or peptide. The signal peptide causes secretion of the expressed protein or peptide from the organism. The signal peptide can be expressed attached to the N-terminus or the C-terminus of the protein or peptide. The signal peptide can also be an internal signal sequence. The sequence encoding the protein or peptide can also be operably linked to a promoter (which can be exogenous, heterologous, or native) and/or other regulatory sequences. The protein or peptide can be secreted in various ways, for example through the Type III secretion system of *Vibrio* sp. In various embodiments the protein or peptide can be expressed from the altered ChII, from ChI, or from an exogenous vector, plasmid, cosmid, or artificial chromosome. In various embodiments the functional signal peptide can have a sequence of any of SEQ ID NO: 8-28 or a variant of any of them. A functional *Vibrio* sp. signal peptide is a sequence that causes the exogenous or heterologous protein or peptide to be secreted from a *Vibrio* sp. cell, which can be secreted into the periplasmic space or to the exterior of the organism. Signal peptides may be recognized by cellular structures or by the cell's secretory pathway that exports the protein or peptide from the cell. In some embodiments the sequences can be from 10-15 or 10-20 or 10-40 amino acids in length, or from 10-35 or from 10-25 or from 15-30 or from 15-30 or from 10-60 amino acids in length. In various embodiments the signal peptide can be any one or more of SEQ ID NO: 8-28 or a variant of any of them, or a functional fragment of any of them.

In various embodiments the organisms of the invention can secrete exogenous or heterologous proteins of interest in large amounts. The amount of exogenous or heterologous protein secreted can be expressed as mg of protein per liter of culture per time unit. The engineered organisms of the invention can secrete an exogenous or heterologous protein of interest in amounts of at least 1 mg/L/hour, or at least 5 mg/L/hour, or at least 10 mg/L/hour, or at least 20 mg/L/hour, or at least 50 mg/L/hour, or at least 70 mg/L/hour, or at least 100 mg/L/hour, or at least 200 mg/L/hour, or at least 300 mg/L/hour, or at least 500 mg/L/hour, or at least 1 g/L/hour, or 10-100 mg/L/hour, or 10-200 mg/L/hour, or 10-300 mg/L/hour, or 10-500 mg/L/hour, or 10 mg/L/hr to 1 g/L/hr or 10 mg/L/hr to 2 g/L/hr, or 50-100 mg/L/hour, or 50-200 mg/L/hour, or 50-500 mg/L/hour, or 50 mg/L/hr to 1 g/L/hr or 50 mg/L/hr to 2 g/L/hr.

The proteins or peptides that are expressed, produced, and secreted in the invention can be any protein or peptide, for example insulin, pro-insulin, glucagon-like peptide, a gonadotropin releasing hormone, an agonist of gonadotropin releasing hormone, somatostatin and inhibitors thereof, octreotide, goserelin, leuprolide, granulocyte stimulating factor (rh-GCSF), levansucrase, as some examples.

Shuttle Vector

The altered ChII of the invention can contain genetic elements that enable it to be replicated or used as a cloning or expression vector not only in *Vibrio* sp., but also in *E. coli.* or *Bacillus* sp., (e.g., *Bacillus subtilis*), or in *E. coli* and *Bacillus* sp. The altered ChII can therefore serve as a shuttle vector between *Vibrio* sp. and *E. coli,* or between *Vibrio* sp. and *Bacillus* sp., or between *E. coli* and *Bacillus* sp. In various embodiments the shuttle vector comprises a sequence from ChII, an origin of replication for each cell type (a *Vibrio* organism and a non-*Vibrio* organism, e.g., *E. coli*), and one or more selection markers. It can have any of the promoters described herein, for example lambda phage pR, pL, trc, lacUV5, araBAD, or a tet-inducible promoter.

The shuttle vector of the present invention contains the replication machinery from *Vibrio* sp. In one embodiment the replication machinery of *Vibrio* sp. has SEQ ID NO: 1 or a variant thereof. Shuttle vectors can carry any DNA of interest. Examples include DNA encoding for a protease, a phytase, a metabolic enzyme, proinsulin, or a granulocyte colony stimulating factor (GCSF). The DNA can also encode for an entire enzymatic pathway or a partial or complete bacterial chromosome.

Cold Tolerance

Reactive oxygen species (ROS) such as singlet oxygen, superoxide anion, hydrogen peroxide, and hydroxyl radicals are a consequence of aerobic metabolism and can cause cellular damage through the oxidation of biological molecules. These oxygen species can be generated in an enhanced amount as a result of various types of cellular stress, including cold stress. The invention provides an engineered *Vibrio* sp. organism comprising one or more nucleotide sequence(s) encoding one or more enzyme(s) from an ROS detoxification system. The one or more enzyme can be selected from one or more of a peroxidase, a dismutase, a reductase, and a transferase, or any combination of them, and which enzyme can be an algal, microalgal, bacterial, cyanobacterial or other type or source of enzyme. The enzyme can be selected from one or more of glutathione peroxidase (which can have reduced monomeric glutathione (GSH) as substrate), superoxide dismutase, guaiacol peroxidase (GPX), enzymes of ascorbate-glutathione (AsA-GSH) cycle ascorbate peroxidase (APX), monodehydroascorbate reductase (MDHAR), dehydroascorbate reductase (DHAR), glutathione reductase (GR), catalase peroxidase (e.g. katG and/or katE), alkyl hydroperoxide reductase, and glutathione S-transferase. The nucleotide sequence(s) can be exogenous or heterologous, and the one or more enzymes can be exogenous or heterologous enzymes.

The invention provides engineered *Vibrio* sp. organisms having a heterologous or exogenous nucleic acid sequence encoding at least one enzyme from an ROS detoxification system, which can be present on a plasmid or other vector. It was discovered unexpectedly that the engineered organisms have a greater ability to tolerate cold stress than non-engineered organisms and can therefore remain viable and culturable after incubation at lower temperatures and for substantially greater periods of time than non-engineered organisms. An ROS detoxification system can convert any of the reactive oxygen species into one or more of oxygen or water. The enzyme from an ROS system can be operably linked to or under the control of an exogenous or heterologous promoter and/or other regulatory sequences.

Some organisms are cold sensitive, meaning that when stored or incubated at lower temperatures they go into a non-viable or non-culturable state when incubated at low temperatures (e.g., below 6° C. or below 5° C. or below 4° C.) for as little as 2-3 days and cannot be grown up or amplified efficiently to produce new colonies. Natural *Vibrio* sp. are cold sensitive organisms. In one embodiment the engineered *Vibrio* sp. organism is maintained on a solid media, i.e. one that does not flow when tilted against gravity. But liquid or semi-solid media can also be used depending on the application. Some solid media contain 0.6% or more, or at least 0.7% or at least 0.8% or at least 0.9% or at least 1.0% or at least 1.1% or at least 1.2% or at least 1.3% or at least 1.4% agar. Semi-solid media are soft enough so that motile bacteria can swim through it. An example of semi-solid media would be one having less than 0.6% agar.

In some embodiments the *Vibrio* sp. of the invention is able to remain viable and culturable after incubation or storage at temperatures of less than 20° C. or less than 15° C. or less than 10° C. or less than 8° C. or less than 6° C. or less than 5° C., or less than 4° C., or less than 3° C., or less than 2° C., or less than 1° C. or 0-4° C. or 0-5° C. or 0-6° C. or 1-4° C. or 1-5° C. or 1-6° C. or 3-5° C. or 2-6° C. The organism can be stored or incubated at these temperatures for a least 1 hour or at least 2 hours or at least 6 hours or at least 12 hours or at least 24 hours or at least 48 hours or at least 3 days or at least 5 days or at least 7 days or at least 9 days or at least 10 days or at least 12 days or at least 14 days or at least 16 days or at least 18 days or at least 19 days or at least 20 days or at least 22 days or at least 24 days or at least 26 days or at least 28 days or at least 30 days and remain culturable and/or viable. In some embodiments the organism retains viability or culturability after storage or incubation at the stated temperatures and the stated time periods on solid medium as described above or in a liquid broth or semi-solid medium. Viability or culturability refers to the ability of a colony to generate new colonies after incubation at low temperatures described herein and re-streaking. This can be determined by touching a colony and spreading it on a culture plate and determining the number of colonies that are generated. Non-viable or non-culturable colonies produce substantially fewer or no colonies while culturable or viable colonies produce a normal number of colonies and/or can show robust growth after such incubations. In other embodiments the engineered organism remains substantially more viable or more culturable than non-engineered organisms after being cultivated at low temperature under the same conditions. The engineered organisms can produce at least 2× or at least 3× or at least 5× or at least 10× or at least 20× or at least 30× or at least 40× or at least 50× or at least 100× as many colonies as non-engineered organisms when re-cultured under the same conditions.

Figure 10A:
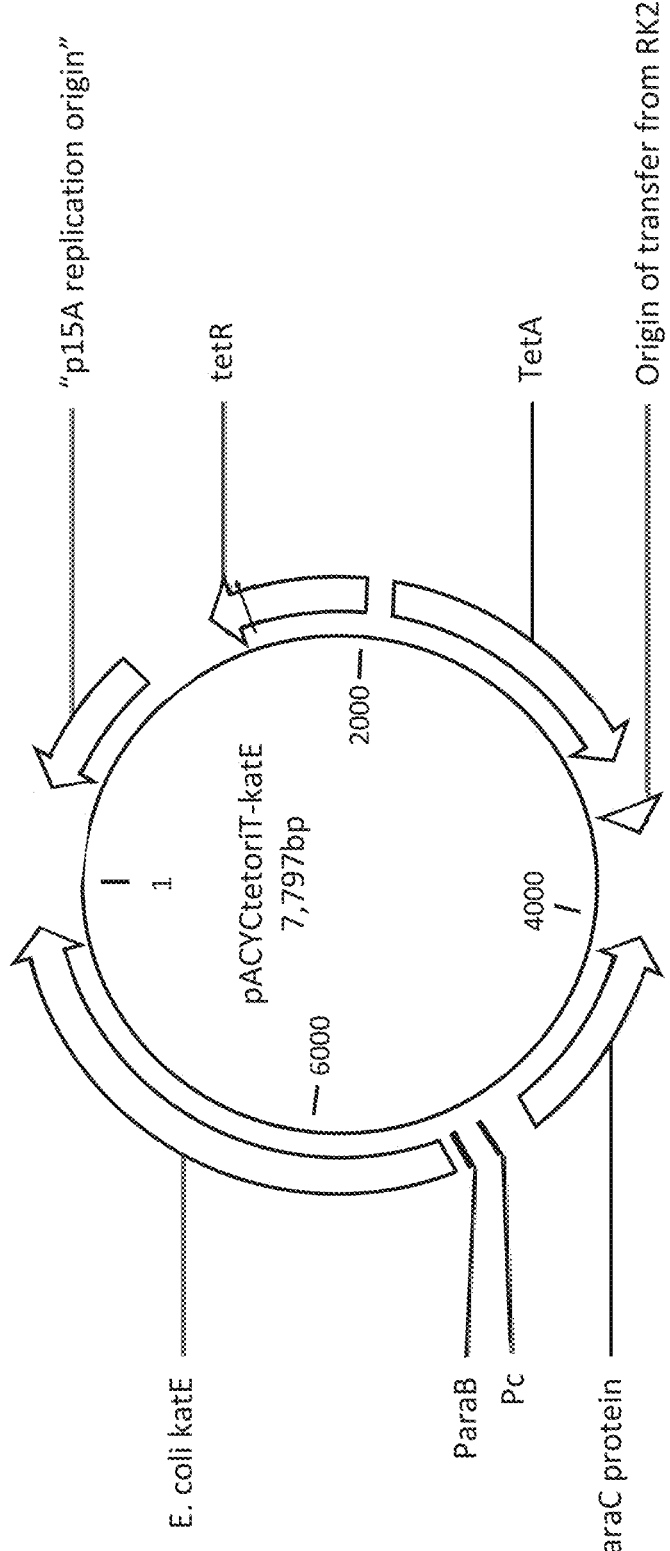
FIG. 10A-10C are schematic illustrations of plasmids conferring cold tolerance to *Vibrio* sp. organisms. The PCR product for the 1566 bp ahpCF operon begins at the ahpC start codon (ATG), includes the native ahpF promoter, and ends at the ahpF stop codon. ahpCF and katG were amplified from *E. coli* strain W3110 while katG was amplified from *E. coli* strain BW25141. The plasmids also contain an arabinose-inducible copy of katE (FIG. 10A), katG (FIG. 10B), or ahpCF (FIG. 10C), an origin of transfer from plasmid RK2 (aka RP4) for mobilization via conjugation, a tetracycline resistance cassette, and the p15A origin of replication.
Figure 10B:
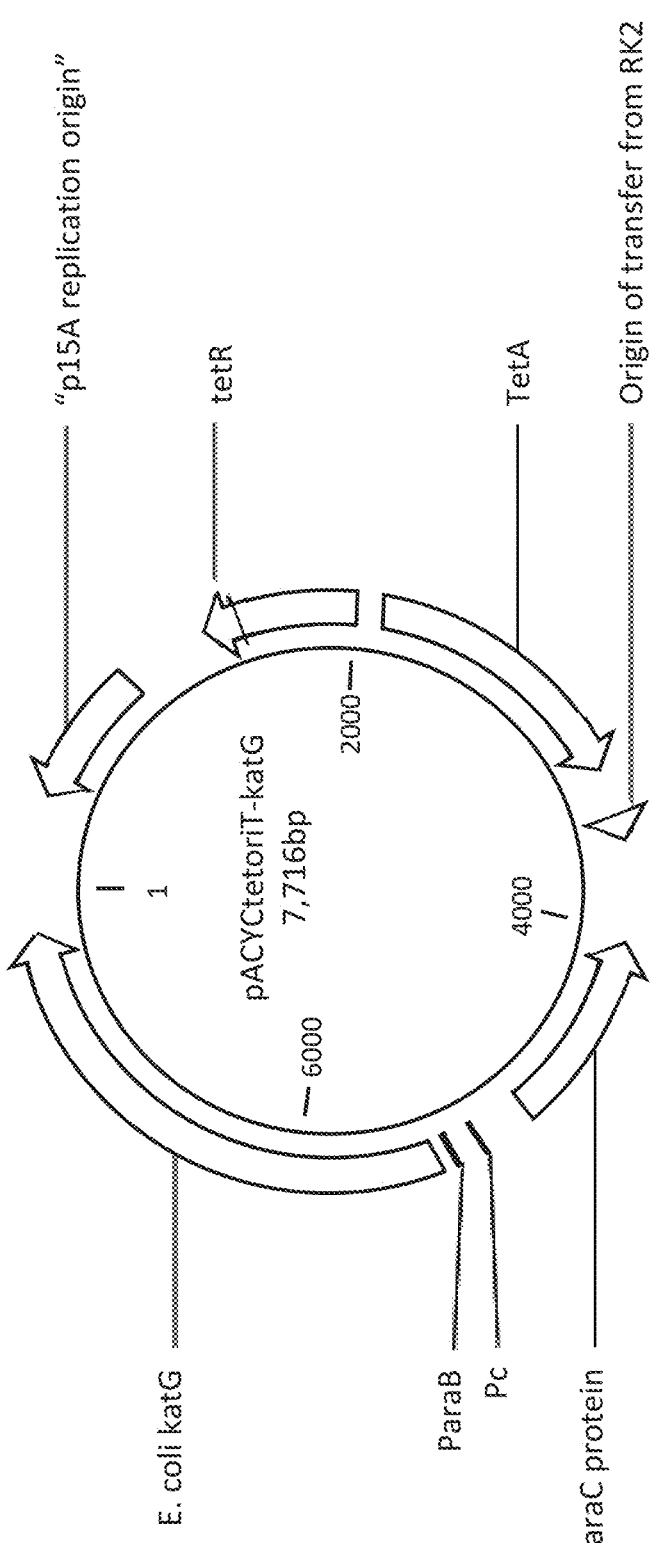
Figure 10C:
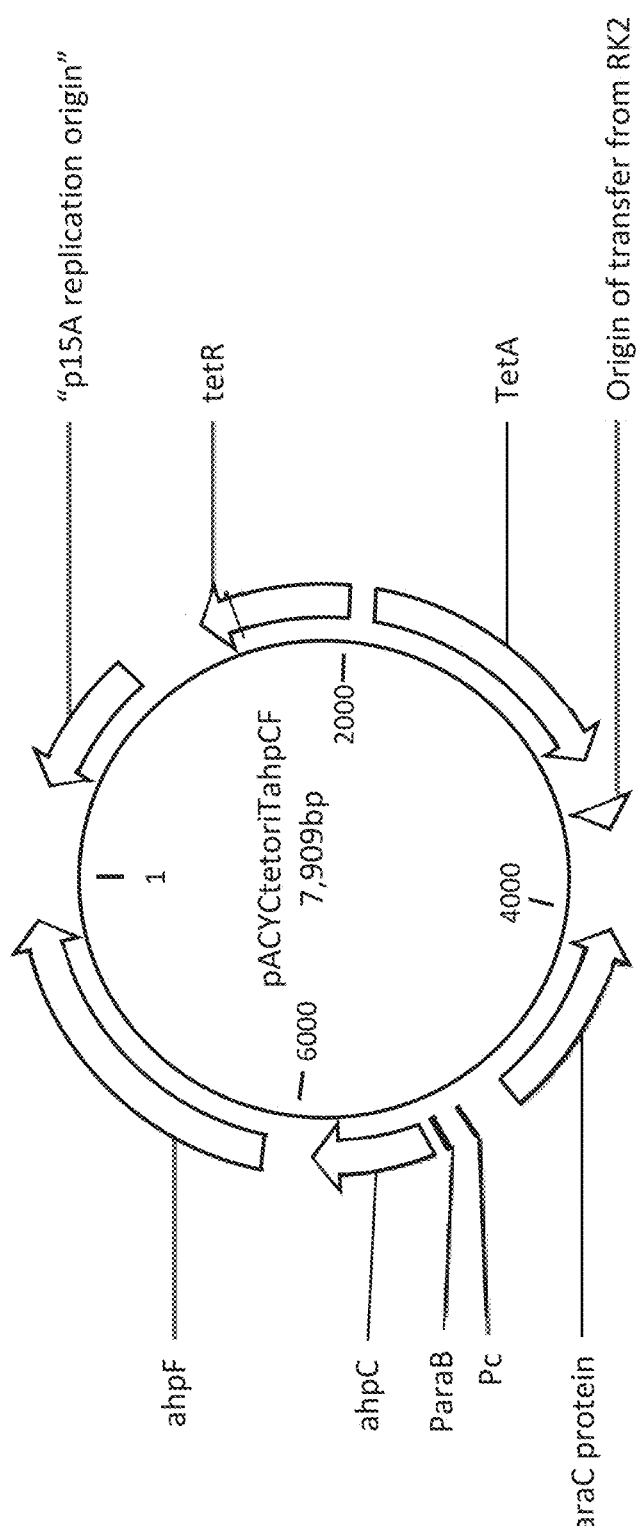

In various embodiments the cold tolerant *Vibrio* sp. of the invention is a *Vibrio* sp. described herein. Cold tolerance can be conferred by engineering one or more exogenous or heterologous nucleic acid sequences conferring cold tolerance, as described herein, into a vector (e.g. a plasmid, cosmid, artificial chromosome or other vector), or into ChI or ChII or a combination thereof. The organism can be transformed with the vector. In some embodiments the engineered *Vibrio* sp. organism contains an exogenous or heterologous nucleotide sequence encoding at least one alkyl hydroperoxide reductase gene (e.g. an ahp operon), or a catalase gene katG and/or katE, or a glutathione S-transferase gene, or any combination of these. The sequences can be under the control of or operably linked to a promoter and/or other appropriate regulatory sequences, which can be exogenous or heterologous. The nucleic acid sequences can be operable in *Vibrio* sp. and in other organisms as well. In embodiments where the alkyl hydroperoxide reductase operon is present it can be the ahpCF from *E. coli* or a variant thereof. In embodiments where the catalase peroxidase gene is present it can be katG or katE, but both can also be used. katG and katE can be obtained from *E. coli* or other sources. In embodiments where the glutathione S-transferase gene is present it can be gstA, and can be from *E. coli* or another suitable source. FIG. 10*a-c* provides non-limiting examples of vectors for expressing cold tolerance.

In one embodiment the vector or construct is a plasmid and has a p15A origin of replication, a tetracycline resistance cassette, the origin of transfer for plasmid RP4, and *E. coli* katE, katG, or the ahpCF operon, optionally under the control of an arabinose-inducible promoter (as described herein) or another promoter.

Expression Cassettes

In another aspect the invention provides expression cassettes operable in *Vibrio* sp. that has a promoter inducible with sucrose. The promoter can be operably linked to a heterologous gene that encodes a protein or peptide or other desirable nucleic acid molecule. The expression cassette can further encode a signal peptide that causes the secretion of the heterologous protein or peptide from the organism. The inducible promoter, and the sequences encoding the signal peptide and heterologous protein or peptide can all be operably linked so that upon inducing the promoter the organism produces and secretes the heterologous protein or peptide. The heterologous protein or peptide can be secreted with the signal peptide attached or the signal peptide can be removed by the organism and secrete the heterologous protein or peptide without the signal peptide. The signal peptide can be any described herein. In one embodiment the inducible promoter has SEQ ID NO: 5 or 6 or a portion or variant of SEQ ID NO: 5 or 6. When the inducible promoter comprises a portion of SEQ ID NO: 5 or 6 it can comprise at least 50% or at least 60% or at least 70% or at least 80% or at least 90% or at least 95% or at least 97% or at least 98% or at least 99% of SEQ ID NO: 5 or 6.

In some embodiments the inducible promoter has a sequence identity of at least 70% or at least 80% or at least 90% or at least 95% or at least 97% or at least 98% or at least 99% of any of SEQ ID NO: 5-6, or a variant thereof. In other embodiments the inducible promoter has a sequence identity of at least 70% or at least 80% or at least 90% or at least 95% or at least 97% or at least 98% or at least 99% to a sequence of at least 100 or at least 200 or at least 300 or at least 400 or at least 500 consecutive nucleotides from SEQ ID NO: 5 or 6.

The expression cassettes can be comprised in any vector operable in *Vibrio* sp. The expression cassette can also include a 3' untranslated region (e.g., a poly-A sequence) and/or a 5' untranslated region (or leader sequence).

"Expression cassette" as used herein means a DNA sequence capable of directing expression of a particular nucleotide sequence in an appropriate host cell, comprising a promoter operably linked to a nucleotide sequence of interest, which can optionally be operably linked to termination signals and/or other regulatory elements. An expression cassette can also have sequences that enable, mediate, or enhance translation of the nucleotide sequence. The coding region usually codes for a protein or peptide of interest but may also code for a functional RNA of interest, for example antisense RNA or a non-translated RNA, in the sense or antisense direction. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby instructions for cloning DNA or for producing the protein or peptide. The kits of the invention can contain any one or more of the above components in any combination of the components. The host cells provided with the kit can optionally contain the vector of the kit. The host cells can also optionally be provided in a container having the buffer provided with the kit or on a solid or semi-solid media. The vector provided in the kit can optionally have an inducible promoter described herein. In various embodiments the host cells are any *Vibrio* sp. bacteria disclosed herein, but the host cells can also be *E. coli* or *S. cerevisiae* or *Bacillus* cells.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Growth of *V. natriegens* In a Range of Growth Media as Well a at Multiple Temperatures Growth of *V. natriegens* was examined on a number of different growth media and at multiple temperatures. A glycerol stock of *V. natriegens* was used to inoculate liquid cultures or was streaked out on agar plates. Liquid cultures were cultivated with agitation ranging from 175-220 RPM at the indicated temperatures. After overnight incubation, plates/cultures were examined for growth. Growth was defined as turbidity (in the case of liquid cultures) or visible colonies (in the case of agar plates).

Media Compositions are as Follows

LB broth: 10.0 g/L Tryptone, 5.0 g/L Yeast Extract, 10.0 g/L NaCl

LB broth+v2 salts: LB broth supplemented with additional salts (204 mM NaCl, 4.2 mM KCl, and 23.14 mM MgCl2)

LB broth+v2 salts+glucose: LB broth supplemented with additional salts (204 mM NaCl, 4.2 mM KCl, and 23.14 mM MgCl2)+0.2% glucose LB broth+v3 salts: LB broth supplemented with additional salts (475 mM NaCl, 9.7 mM KCl, and 54 mM MgCl2)

LB broth+v3 salts+glucose: LB broth supplemented with additional salts (475 mM NaCl, 9.7 mM KCl, and 54 mM MgCl2)+0.2% glucose LB agar: LB media+1.5% agar-agar LB agar+v2 salts: LB broth supplemented with additional salts (204 mM NaCl, 4.2 mM KCl, and 23.14 mM MgCl2)+1.5% agar-agar LB agar minus NaCl with 6% sucrose: 10.0 g/L Tryptone, 5.0 g/L Yeast Extract, 1.5% agar-agar, 6% sucrose Nutrient Broth+1.5% NaCl: 8 g/L DIFCO™ Nutrient Broth (Cat. No. 234000) supplemented with 1.5% NaCl Nutrient Agar+1.5% NaCl: 8 g/L DIFCO™ Nutrient Broth (Cat. No. 234000) supplemented with 1.5% NaCl and 1.5% agar-agar Brain Heart Infusion Broth: 37 g/L TEKNOVA® Brain Heart Infusion Broth Dry Media (Cat. No. B9500)

Brain Heart Infusion Broth+2% NaCl: 37 g/L TEKNOVA® Brain Heart Infusion Broth Dry Media (Cat. No. B9500)+20 g/L NaCl Brain Heart Infusion Broth+1.5% Instant Ocean: 37 g/L TEKNOVA® Brain Heart Infusion Broth Dry Media (Cat. No. B9500)+15 g/L Instant Ocean Sea Salt Mixture Brain Heart Infusion Broth+v2 salts: 37 g/L TEKNOVA® Brain Heart Infusion Broth Dry Media (Cat. No. B9500) supplemented with additional salts (204 mM NaCl, 4.2 mM KCl, and 23.14 mM MgCl2)

Brain Heart Infusion Broth+v3 salts: 37 g/L TEKNOVA® Brain Heart Infusion Broth Dry Media (Cat. No. B9500) supplemented with additional salts (475 mM NaCl, 9.7 mM KCl, and 54 mM MgCl2)

Brain Heart Infusion Agar+1.5% Instant Ocean: 52 g/L DIFCO™ Brain Heart Infusion Agar (Cat. No. 241830)+15 g/L Instant Ocean Sea Salt Mixture Brain Heart Infusion Agar: 37 g/L TEKNOVA® Brain Heart Infusion Broth Dry Media (Cat. No. B9500)+1.5% agar-agar Brain Heart Infusion Agar+v2 salts: 37 g/L TEKNOVA® Brain Heart Infusion Broth Dry Media (Cat. No. B9500)+1.5% agar-agar supplemented with additional salts (204 mM NaCl, 4.2 mM KCl, and 23.14 mM MgCl2)

M9 glucose media (500 mL): 1×M9 Salts, 0.4% glucose, 2 mM $MgSO_4$, 0.1 mM $CaCl_2$)

M9 glucose agar: M9 glucose media supplemented with 1.5% agar-agar

M9 glucose with 1% sucrose: 1×M9 Salts, 0.4% glucose, 2 mM $MgSO_4$, 0.1 mM $CaCl_2$, 1% sucrose M9 glucose with 2% sucrose: 1×M9 Salts, 0.4% glucose, 2 mM $MgSO_4$, 0.1 mM $CaCl_2$, 2% sucrose M9 glucose with 4% sucrose: 1×M9 Salts, 0.4% glucose, 2 mM $MgSO_4$, 0.1 mM $CaCl_2$, 4% sucrose M9 1% sucrose: 1×M9 Salts, 2 mM $MgSO_4$, 0.1 mM $CaCl_2$, 1% sucrose M9 2% sucrose: 1×M9 Salts, 2 mM $MgSO_4$, 0.1 mM $CaCl_2$, 2% sucrose M9 4% sucrose: 1×M9 Salts, 2 mM $MgSO_4$, 0.1 mM $CaCl_2$, 4% sucrose marine agar: 55.1 g/L Difco™ Marine Agar 2216 (Cat. No. 212185)

Bacto Heart Infusion Broth: 25 g/L BACTO™ Heart Infusion Broth (Cat. No. 238400)

SSG agar: 28 g/L BACTO™ SOB Medium (Cat. No. 244310), 17% Fetal Bovine Serum, 1% glucose, 4 mL/L Phenol Red Solution (Sigma P0290)

2×YT+v2 salts+glucose+phosphate buffer: 2×YT media (16 g/L Tryptone, 10 g/L Yeast Extract, 5 g/L NaCl) is supplemented with v2 salts (204 mM NaCl, 4.2 mM KCl, 23.14 mM $MgCl_2$), 17.61 mM $Na_2HPO_4$, 0.2% glucose. pH is adjusted to 7.4.

Vegitone Infusion Broth+v2 salts: Vegitone Infusion Broth (Sigma Aldrich cat #41960) supplemented with v2 salts (204 mM NaCl, 4.2 mM KCl, 23.14 mM $MgCl_2$).

LB+v2 salts+glucose+phosphate buffer: LB media (10 g/L Tryptone, 5 g/L Yeast Extract, 10 g/L NaCl) is supplemented with v2 salts (204 mM NaCl, 4.2 mM KCl, 23.14 mM MgCl$_2$), 17.6 mM K$_2$HPO$_4$, 0.200 glucose. pH is adjusted to 7.0.

TABLE 1

| Media | Format | 25° C. | 30° C. | 37° C. |
|---|---|---|---|---|
| LB broth | liquid culture | Growth | growth | no growth |
| LB broth + v2 salts | liquid culture | N/A | growth | growth |
| LB broth + v2 salts + glucose | liquid culture | N/A | growth | growth |
| LB broth + v3 salts | liquid culture | N/A | growth | growth |
| LB broth + v3 salts + glucose | liquid culture | N/A | growth | growth |
| LB agar | agar plate | Faint | growth | growth |
| LB agar + v2 salts | agar plate | N/A | growth | growth |
| LB agar minus NaCl with 6% sucrose | agar plate | N/A | no growth | no growth |
| Nutrient Broth + 1.5% NaCl | liquid culture | Growth | growth | no growth |
| Nutrient Agar + 1.5% NaCl | agar plate | slow growth | growth | attenuated growth |
| Brain Heart Infusion Broth | liquid culture | Growth | growth | attenuated growth |
| Brain Heart Infusion Broth + 2% NaCl | liquid culture | Growth | growth | growth |
| Brain Heart Infusion Broth + 1.5% Instant Ocean | liquid culture | Growth | growth | growth |
| Brain Heart Infusion Broth + v2 salts | liquid culture | N/A | growth | growth |
| Brain Heart Infusion Broth + v3 salts | liquid culture | N/A | growth | growth |
| Brain Heart Infusion Agar + 1.5% Instant Ocean | agar plate | slow growth | growth | growth |
| Brain Heart Infusion agar | agar plate | N/A | growth | N/A |
| Brain Heart Infusion agar + v2 salts | agar plate | Growth | growth | growth |
| M9 glucose media | liquid culture | slow growth | growth | N/A |
| M9 glucose agar | agar plate | slow growth | growth | slow growth |
| M9 glucose with 1% sucrose | agar plate | N/A | growth | growth |
| M9 glucose with 2% sucrose | agar plate | N/A | growth | growth |
| M9 glucose with 4% sucrose | agar plate | N/A | growth | growth |
| M9 1% sucrose | agar plate | N/A | growth | growth |
| M9 2% sucrose | agar plate | N/A | growth | growth |
| M9 4% sucrose | agar plate | N/A | growth | growth |
| marine agar | agar plate | slow growth | growth | growth |
| Bacto Heart Infusion Broth | liquid culture | N/A | growth | attenuated growth |
| SSG agar | agar plate | Growth | growth | growth |
| 2xYT + v2 salts + glucose + phosphate buffer | Liquid culture | N/A | growth | growth |
| Vegitone Infusion Broth + v2 salts | Liquid culture | N/A | growth | growth |
| LB + v2 salts + glucose + phosphate buffer | Liquid culture | N/A | growth | growth |

Example 2

Transformation of *V. natriegens* with Exogenous DNA Constructs Via Conjugation

This method was used to transfer a mobilizable plasmid from *E. coli* into *V. natriegens* where:

1) the plasmid was maintained as an episomal molecule in *V. natriegens*, or 2) where (with appropriate plasmid design) the plasmid integrated into the *V. natriegens* chromosome via a single or double-crossover integration event.

Donor preparation: 10 mL of LB medium containing appropriate antibiotic was inoculated with *E. coli* donor strain (containing mobilizable plasmid of interest) and incubated overnight at 37° C. with agitation (200 RPM). Acceptable donor strains include, but are not limited to strain S17-1 λpir (containing the RP4 conjugation machinery integrated into the chromosome) or EPI300 cells harboring the pRL443 conjugative plasmid.

Recipient preparation: 10 mL of LB medium was inoculated with *V. natriegens* recipient strain and incubated overnight at room temperature with agitation (175 RPM).

Conjugative mating: Donor and recipient cultures were retrieved from incubators. 1 mL of each culture was separately centrifuged at 5000×g for 3 min in a 1.5 mL Eppendorf tube to pellet the cells. The supernatant was decanted and the cell pellets were each resuspended in 1 mL fresh LB medium. The wash (centrifugation/decanting/resuspension) was repeated for the donor strain to further reduce residual antibiotic carryover. Donor and recipient cultures were then mixed in multiple different ratios (e.g., 1:9, 1:4, 1:1, 4:1, 9:1 donor:recipient) in a total volume of 100 μL. The 100 μL of cells were spotted out as 10 μL spots on prewarmed LB plates, and incubated at 30° C. for 3-5 hours. Cells were washed from plate with 1 mL M9 glucose medium. Various volumes of cells (1 μL, 5 μL, 20 L) were plated out on M9 glucose plates containing appropriate antibiotic and incubated overnight at 30° C. The *E. coli* donor strains mentioned above will not grow on the M9 medium utilized for this procedure (see recipe below). Individual *V. natriegens* colonies that grew on the M9 selective plate were then screened for successful conjugation event via standard methods.

M9 glucose medium (500 mL):

100 mL 5×M9 Salts 390 mL ddH2O 7.5 g agar-agar*

10 mL 20% glucose**

1 mL 1 M MgSO$_4$**

50 μL 1 M CaCl$_2$)**

*for solid media, add agar-agar

**added after autoclaving

Example 3

Transformation of *V. natriegens* with Exogenous DNA Constructs Via Electroporation Preparation of Electrocompetent cells: 10 mL of Brain Heart Infusion Broth supplemented with supplemented salts (204 mM NaCl, 4.2 mM KCl, and 23.14 mM MgCl2) was inoculated with *Vibrio natriegens* and incubated overnight at 30° C. with agitation. On the following day, 250-500 mL of the same growth media was inoculated with the overnight culture at a dilution of 1:100 to 1:200 (overnight culture: fresh media). The culture was grown at 37° C. with shaking until an OD600 of 0.5. The culture was then split into two pre-chilled 250 mL centrifuge bottles which were then incubated on ice for 0-20 min. The cells were pelleted at 6500 RPM in a JA-14 centrifuge rotor for 20 min at 4° C. The supernatant was carefully decanted and the cell pellets were gently resuspended in 5-10 mL of electroporation buffer (680 mM sucrose, 7 mM K$_2$HPO$_4$, pH 7). The suspension was transferred to centrifuge tubes and the tube was filled to top (~35 mL) with additional electroporation buffer and inverted several times to mix. The cells were spun down at 6750 RPM for 15 min at 4° C. in a JA-17 rotor. The supernatant was decanted with pipette. The wash was repeated two times for a total of three washes. After the final wash, the cells were gently resuspended in residual electroporation buffer. The volume was adjusted with additional electroporation buffer to bring the final OD600 to 16. Cells were aliquoted into pre-chilled tubes and were stored at −80° C. until use.

Electroporation protocol: A vial of competent cells was retrieved from storage at −80° C. and allowed to thaw on ice. Plasmid DNA and electrocompetent cells were combined and gently mixed in a pre-chilled 1.5 mL microfuge tube. The cell/DNA suspension was transferred to a pre-chilled electroporation cuvette with a 0.1 cm gap size. Cells were electroporated with the following parameters: 700-900 V, 25 pF, 200Ω, 1 mm cuvette. Cells were immediately recovered in 500 µL recovery media (Brain Heart Infusion Broth supplemented with supplemented salts (204 mM NaCl, 4.2 mM KCl, 23.14 mM MgCl2, and 0-680 mM sucrose) and transferred to a 15 mL culture tube. The cells were recovered by incubating at 30-37° C. for 1-2 hours. Aliquots of the recovery media were plated out on pre-warmed agar plates containing appropriate antibiotic. Acceptable agar media include, but are not limited to: M9 glucose, Brain Heart Infusion Agar (with or without additional salt supplementation), and LB (with our without additional salt supplementation). The plates were incubated for several hours to overnight at 30-37° C. for colonies to appear.

Example 4

The Use of *V. natriegens* as a Host for Molecular Cloning

Recombinant DNA fragments for assembly were derived from multiple sources including, but not limited to: digestion of existing recombinant DNA using nucleases (e.g., restriction enzymes, homing endonucleases, zinc-finger nucleases, TALENs, Cas9 nuclease with appropriate guide RNAs, etc.), PCR amplification, or de novo gene assembly from synthesized oligonucleotides.

In vitro assembly was carried out with any number of standard DNA construction techniques or commercially available kits including, but not limited to: ligation of DNA fragments using a suitable DNA ligase and GIBSON ASSEMBLY®. Alternatively, in vivo assembly can be performed in a compatible host cell, such as, for example, *E. coli* or *S. cerevisiae* followed by isolated of the assembled product.

Once in vitro or in vivo assembly and isolation, if appropriate, is complete, *V. natriegens* competent cells that have been prepared according to the conjugation or electroporation protocol were transformed according to the appropriate protocol in either Example 2 or Example 3. Cells were plated on agar plates containing the appropriate antibiotic and incubated for several hours to overnight at 30-37° C. for colonies to appear.

Colonies isolated from agar plates containing appropriate antibiotics were used to inoculate growth media containing the same antibiotic. Cells were grown for ~3 hours to overnight at 30-37° C. Cells were harvested by centrifugation, and DNA was then extracted via standard methods (e.g., alkaline lysis techniques) or commercially available kits (e.g., QIASPIN™ Miniprep Kit from QIAGEN®). Extracted DNA was analyzed by standard methods.

Example 5

The Use of *V. NATRIEGENS* as a Host for Inducible Protein Expression

A series of plasmids were designed for inducible protein expression of green fluorescent protein (GFP) in various experiments. The plasmids were designed to contain:

1) one of three promoters (the IPTG-inducible trc promoter, arabinose-inducible araBAD promoter, or the temperature inducible X pR promoter modulated by the temperature-sensitive cI857 repressor.
2) one of two origins of replication (the p15a origin of replication or the origin from plasmid pBR325)
3) a green fluorescent protein (GFP) under the control of the inducible promoter to monitor expression
4) a transcriptional terminator following GFP (rrnB transcriptional termination sequence)
5) a chloramphenicol resistance gene for antibiotic selection The functional elements and their source plasmids are listed in Table 2:

TABLE 2

| Element | Source Plasmid |
|---|---|
| trc promoter | pTrcHisA |
| araBAD promoter | pKD46 |
| λ pR promoter/temperature-sensitive cI857 repressor | 705-cre |
| p15a origin | pACYC184 |
| pBR325 origin | pBR325 |
| GFP gene | synthesized from oligos |
| rrnB transcriptional termination sequence | pTrcHisA |
| chloramphenical acyl transferase gene | pCC1BAC |

The maps for the six plasmids are shown in FIG. 1. The plasmids were assembled in vitro using GIBSON ASSEMBLY® and electroporated into *V. natriegens* following the protocols described in Example 4.

Figure 2:
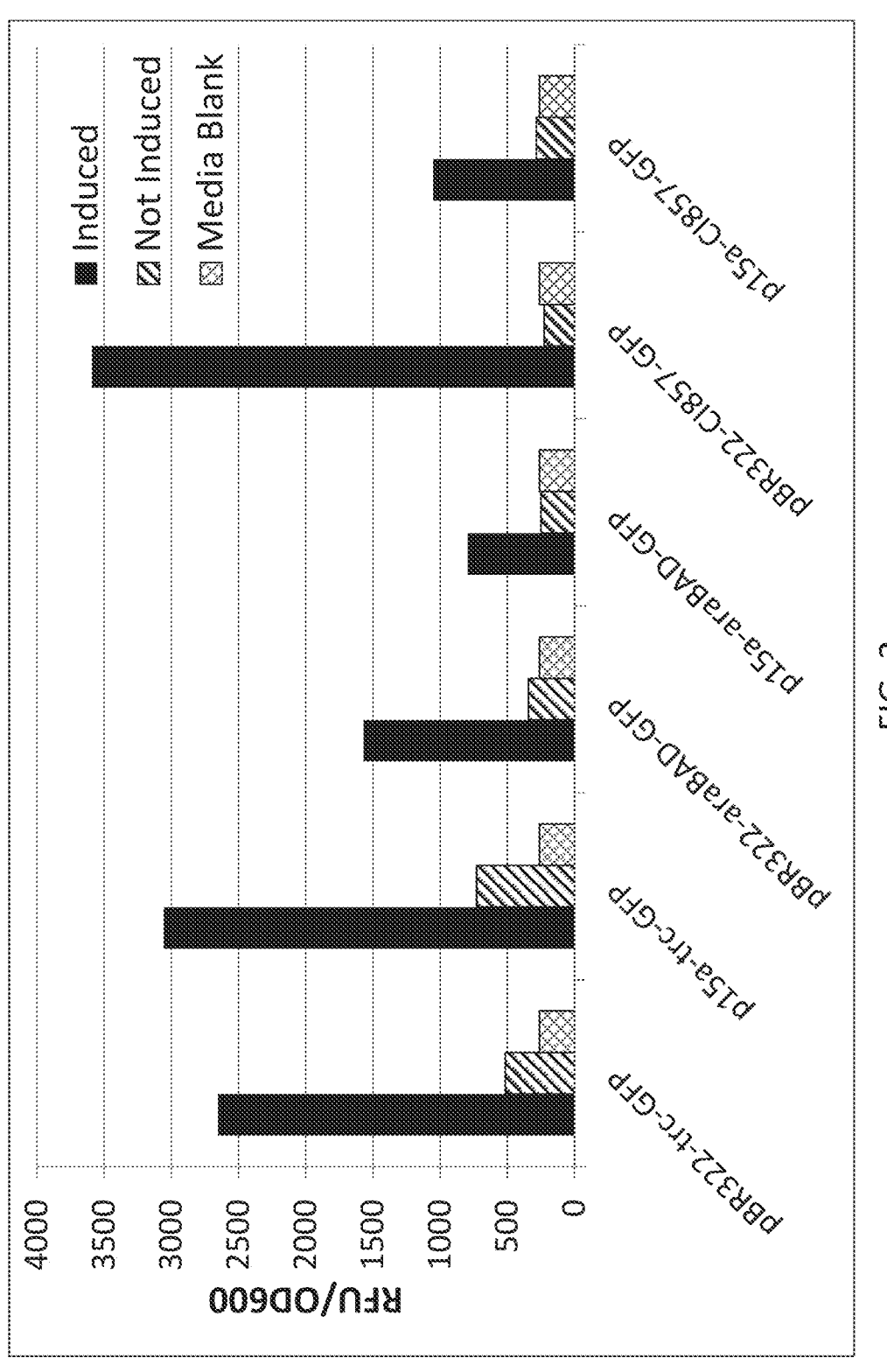
FIG. 2 shows GFP fluorescence normalized to OD600 for induced and non-induced cultures harboring each of the six expression plasmids.

Cultures of individual transformed colonies were grown overnight in LB media (10.0 g/L Tryptone, 5.0 g/L Yeast Extract, 10.0 g/L NaCl) supplemented with additional salts (204 mM NaCl, 4.2 mM KCl, and 23.14 mM MgCl2) at 30° C. with agitation at 200 RPM. On the following day the cultures were used to inoculate fresh salt-supplemented LB media at a ratio of 1:100 overnight culture:fresh media. The cultures were grown at 30° C. with agitation until an OD600 of 0.5. Cultures were then induced with appropriate inducer (0.2% arabinose, 1 mM IPTG, or shifting temperature to 42° C., for the araBAD, trc, and pR promoters respectively). After about 4 hours, the OD600 and GFP fluorescence (excitation 480 nm/emission 510 nm) were measured. FIG. 2 shows GFP fluorescence normalized to OD600 for induced and non-induced cultures harboring each of the six expression plasmids. The data demonstrates the functionality of these inducible promoter systems in this species.

Figure 3:
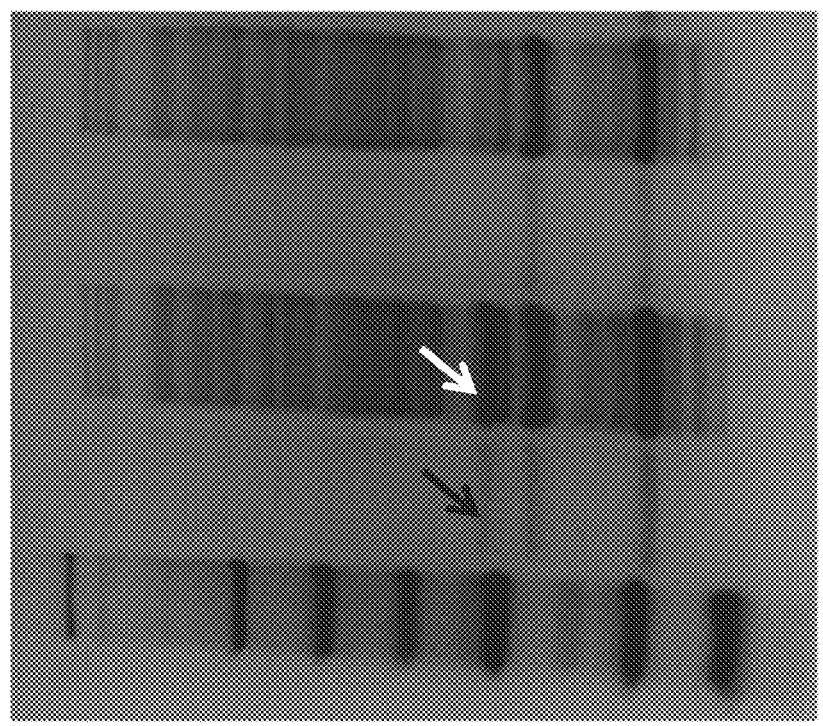
FIG. 3 shows the presence of GFP from cultures of *V. natriegens* harboring pBR322-trc-GFP. Lane 1: SeeBlue Plus2 Protein Standard; Lane 2: 1 μL *V. natriegens* pBR322-trc-GFP lysate from IPTG-induced culture; Lane 3: 10 μL *V. natriegens* pBR322-trc-GFP lysate from IPTG-induced culture; Lane 4: 1 μL *V. natriegens* pBR322-trc-GFP lysate from non-induced culture and Lane 5: 10 μL *V. natriegens* pBR322-trc-GFP lysate from non-induced culture. Arrows indicate GFP.

For further analysis, cultures of *V. natriegens* harboring pBR322-trc-GFP (induced and non-induced) were collected via centrifugation, resuspended in lysis buffer (20 mM Tris pH 8, 2 mM MgCl₂), lysed via sonication, clarified via centrifugation, and run on a 4-12% 10-well BOLT® Bis-Tris gel (LIFE TECHNOLOGIES©) with MES running buffer, which was subsequently stained with SIMPLYBLUE™ safe stain (LIFE TECHNOLOGIES©). In FIG. 3, Lane 1: SEE-BLUE™ Plus2 Protein Standard (LIFE TECHNOLOGIES®); Lane 2: 1 pL *V. natriegens* pBR322-trc-GFP lysate from IPTG-induced culture; Lane 3: 10 μL *V. natriegens* pBR322-trc-GFP lysate from IPTG-induced culture; Lane 4: 1 μL *V. natriegens* pBR322-trc-GFP lysate from non-induced culture and Lane 5: 10 μL *V. natriegens* pBR322-trc-GFP lysate from non-induced culture. The GFP protein can be seen in the lanes corresponding to the induced culture, but is present at much lower levels in the non-induced culture.

Example 6

The Use of ChII as a Cloning/Shuttle Vector in *Vibrio* or Non-*Vibrio* Species (e.g., *E. coli*)

The replication machinery of *V. natriegens* ChII comprises SEQ ID NO: 1.

The vector designated pVnatoriCII was prepared by assembling the following DNA regions from the following sources:

1) *V. natriegens* chrII sequence (amplified from *V. natriegens* genomic DNA) (SEQ ID NO: 1);
2) R6Kγ origin of replication (amplified from plasmid pR6Kan from EPICENTRE®)(SEQ ID NO: 2); and
3) tetA/tetR resistance genes+RP4 oriT (amplified from plasmid pJB3Tc20) (SEQ ID NO: 3).

Figure 4:
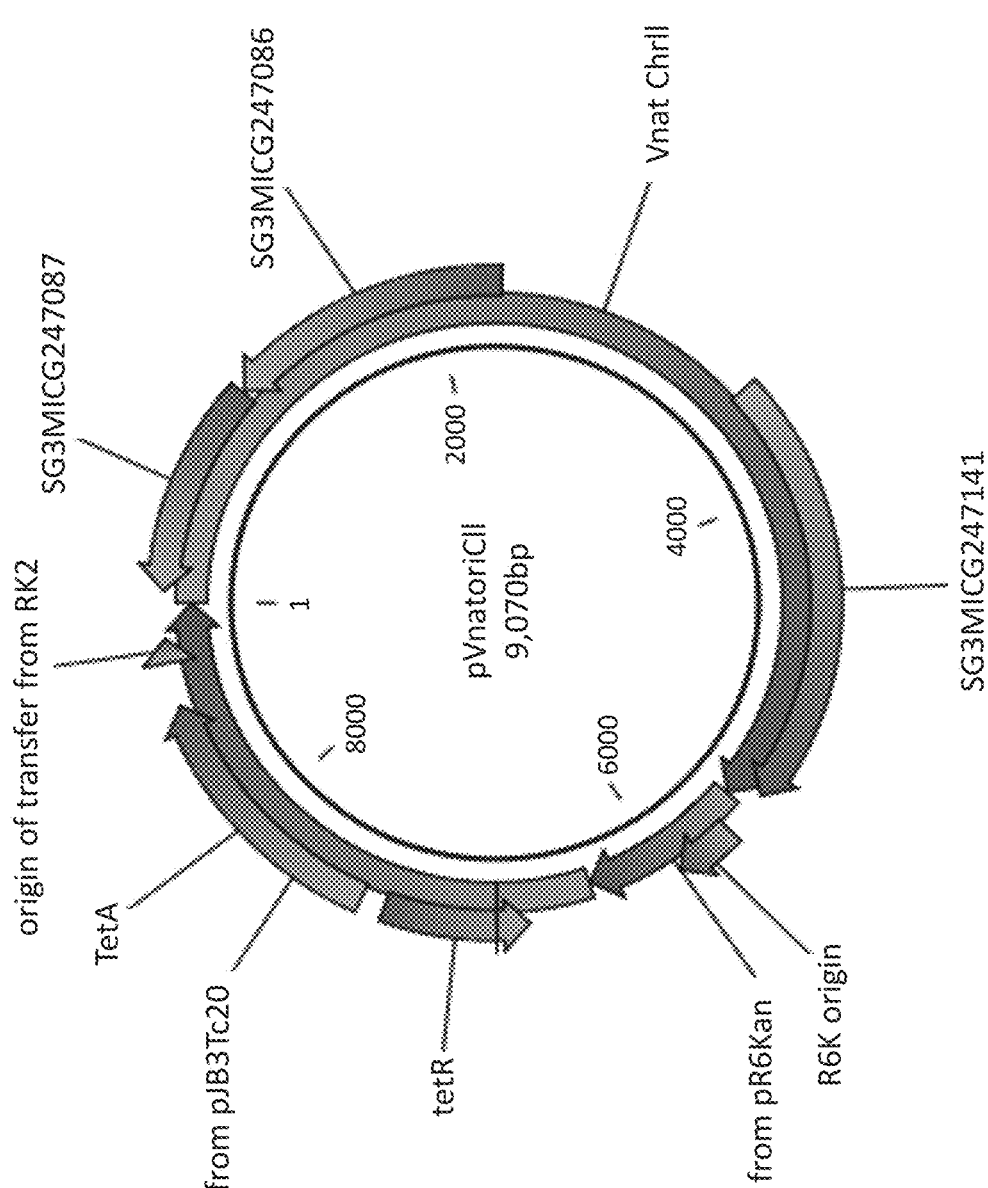
FIG. 4 shows a plasmid comprising the replication machinery sequence from *V. natriegens* chrII, the R6K7 origin of replication and the tetA/tetR resistance genes along with the RP4 oriT region of plasmid pJB3Tc20, which facilitates mobilization of the plasmid by bacterial conjugation.

The PCR primers were designed to generate sufficient homology overlaps between the PCR products to facilitate vector construction via GIBSON ASSEMBLY© to generate the plasmid shown in FIG. 4.

The plasmid comprises the sequence from *V. natriegens* ChII, the R6Kγ origin of replication (without the pir gene encoding the pi n protein necessary for plasmid replication) and the tetA/tetR resistance genes (as a selective marker) along with the RP4 oriT region (to facilitate mobilization of plasmid via conjugation) of plasmid pJB3Tc20 (NCBI genbank U75324).

The vector was assembled in vitro according to standard methods and was transformed into EC100D pir-116 *E. coli* cells from EPICENTRE© via electroporation. These cells contain the pir gene encoding the pi n protein necessary for replication of plasmids containing the R6KT origin of replication. Because the designed plasmid contains the R6Kγ origin, the plasmid will be able to replicate in this strain regardless of the functionality of the *V. natriegens* chrII machinery in *E. coli*. Cells were plated out on LB agar plates containing 10 g/mL tetracycline. Individual colonies were grown up in LB media containing 10 g/mL tetracycline, and DNA was recovered using the QIAPREP® Spin Miniprep Kit from QIAGEN®. Proper vector assembly was verified via restriction digestion analysis. Plasmids with the correct restriction pattern were then electroporated into EPI300 *E. coli* cells from EPICENTRE© via electroporation. Because EPI300 cells do not contain the pir gene encoding the pi n protein necessary for replication of plasmids containing the R6Kγ origin of replication, the only way this plasmid will replicate is if the *V. natriegens* ChII replication machinery is able to support plasmid replication in *E. coli*. The transformation of EPI300 cells with pVnatoriCII resulted in tetracycline resistant colonies, indicating the plasmid successfully replicated in this strain.

Conjugation Mediated Transfer of pVnatoriCII to from *E. coli* to *V. Natriegens:*

The plasmid was also transferred to *V. natriegens* via conjugation from *E. coli* strain S17-1 λpir following the conjugation protocol described in Example 2, giving rise to tetracycline-resistant *V. natriegens* colonies.

Figure 5:
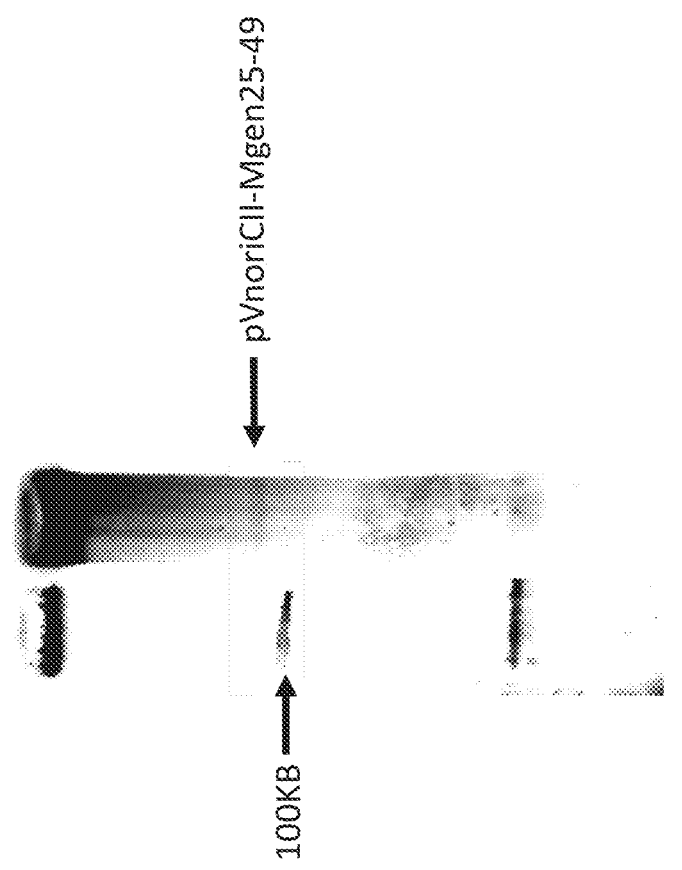
FIG. 5 shows plasmid pVnoriCII-Mgen25-49 run on an agarose gel.

Cloning Large DNAs into pVnatoriCII:

To assess the utility of pVnatoriCII for harboring large DNA molecules in E. co/i, we cloned an about 135 kb sequence from the *Mycoplasma genitalium* genome into the plasmid (by replacing the R6Kγ origin with *M. genitalium* sequence) to generate plasmid pVnoriCII-Mgen25-49. A plasmid carrying a fragment of DNA of greater than 100 kb was recovered from EPI300 cells harboring the plasmid as can be seen by running supercoiled plasmid DNA on an agarose gel (FIG. 5).

Sequencing of the plasmid (ILLUMINA® MISEQ®) confirmed the expected sequence, demonstrating that pVnoriCII can be used to clone fragments of exogenous DNA of greater than 100 kb in *E. coli*.

Improved *E. coli/V. natriegens* Shuttle Vector:

In order to improve upon the design of pVnatoriCII, a second *V. natriegens* ChII plasmid was created (designated pVnatCII-YACTRP-copycontrol (SEQ ID NO: 4)) by leveraging features from the following plasmids:

From pVnoriCII:
 oriT for RP4-mediated conjugal transfer
 *V. natriegens* chrII origin of replication for low copy replication of plasmid
From pCC1BAC™ from EPICENTRE®:
 oriV for use with *E. coli* strains containing the trfA gene product under an inducible promoter (e.g., EPI300 cells from Epicentre®)
 chloramphenicol resistance marker for antibiotic selection
 Multiple Cloning Site (MCS) with convenient restriction enzyme cut sites
 loxP site for recombination via Cre-recombinase
In addition, the plasmid also contains:
ARS/CEN for stabile replication in *Saccharomyces cerevisiae*
Trp gene for selection in a Trp auxotroph of *Saccharomyces cerevisiae*

Figure 6:
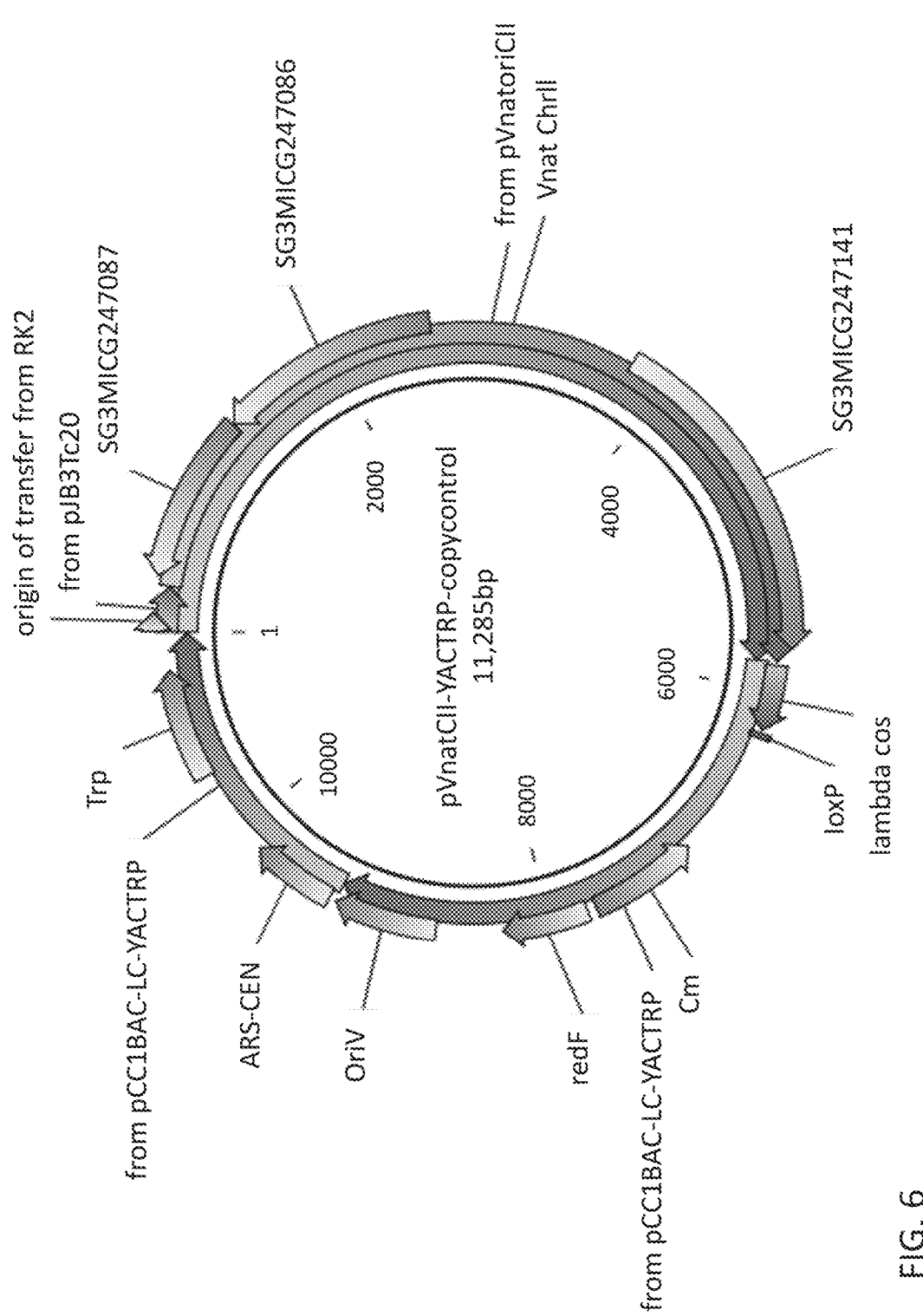
FIG. 6 shows the vector map and sequence of pVnatCII-YACTRP-copy control.

The vector map and sequence of pVnatCII-YACTRP-copy control are shown in FIG. 6. The plasmid pVnatCII-YACTRP-copycontrol was replicated in *E. coli* at low copy, and the copy number was also increased by supplementing the trfA gene product in trans (e.g., via EPI300 cells, which contain an inducible copy of trfA on the chromosome).

The plasmid pVnatCII-YACTRP-copycontrol was also introduced into *E. coli*, *V. natriegens*, and *Saccharomyces cerevisiae* via transformation and maintained under the appropriate selection.

Example 7

Use of a Suicide Plasmid System to Engineer the Genome of *V. natriegens*

We have developed a suicide plasmid system that can be used to remove endogenous DNA sequence or introduce exogenous DNA into the chromosome of *V. natriegens*. The plasmid was constructed with the following DNA elements in the following order:

a) 500 bp of chromosomal sequence directly upstream of the location where an insertion/deletion event was desired to start.
b) A "knock-out/knock-in" cassette containing an antibiotic resistance marker (e.g., Cm antibiotic resistance marker (from pACYC184)) flanked by lox66 and lox71 sites. In addition, if exogenous DNA was to be added into the chromosome, that DNA was contained in this fragment after the lox-bounded Cm marker.
c) 500 bp of chromosomal sequence directly downstream of the location where an insertion/deletion event was desired to end.

d) the R6K origin of replication from pR6Kan (Epicentre®).

e) the RK2 origin of transfer (oriT) from pRL443.

f) the ccdB toxin under control of the arabinose-inducible araBAD promoter (SEQ ID NO:5) (the araC gene and araBAD promoter are from plasmid pKD46).

Because the plasmid lacks the n replication protein necessary to initiate replication from the R6K origin, the plasmid will only replicate when n is supplied in trans (e.g., from the EC100D pir-116 strain from Epicentre®). The plasmid was introduced into an *E. coli* strain capable of supplying the n protein in trans that also contained the conjugation machinery from plasmid RP4 (we use strain S17-1 λpir). The strain was then mated with *V. natriegens* (following the conjugation protocol described in Example 2) to allow mobilization of the plasmid from the donor *E. coli* strain to *V. natriegens*. Because the plasmid is incapable of replicating in *V. natriegens*, the only way that antibiotic-resistant clones were isolated was if the plasmid integrated into the chromosome via the regions of the plasmid that are homologous to the *V. natriegens* genome. Double-crossover integration events were selected for by growing the strain in media (e.g., LB) containing 0.2-0.4% L-arabinose as well as an antibiotic which is contained in the cassette flanked by homology to the *V. natriegens* genome). The presence of arabinose induced the araBAD promoter, thereby producing the ccdB toxin and removing cells that had not undergone integration via double-crossover recombination from the population (the toxin is not present in cells that have undergone double-crossover recombination). Surviving clones were screened for successful integration via standard methods.

Use of the System to Remove Endogenous DNA Sequence from the Chromosome

Figure 7:
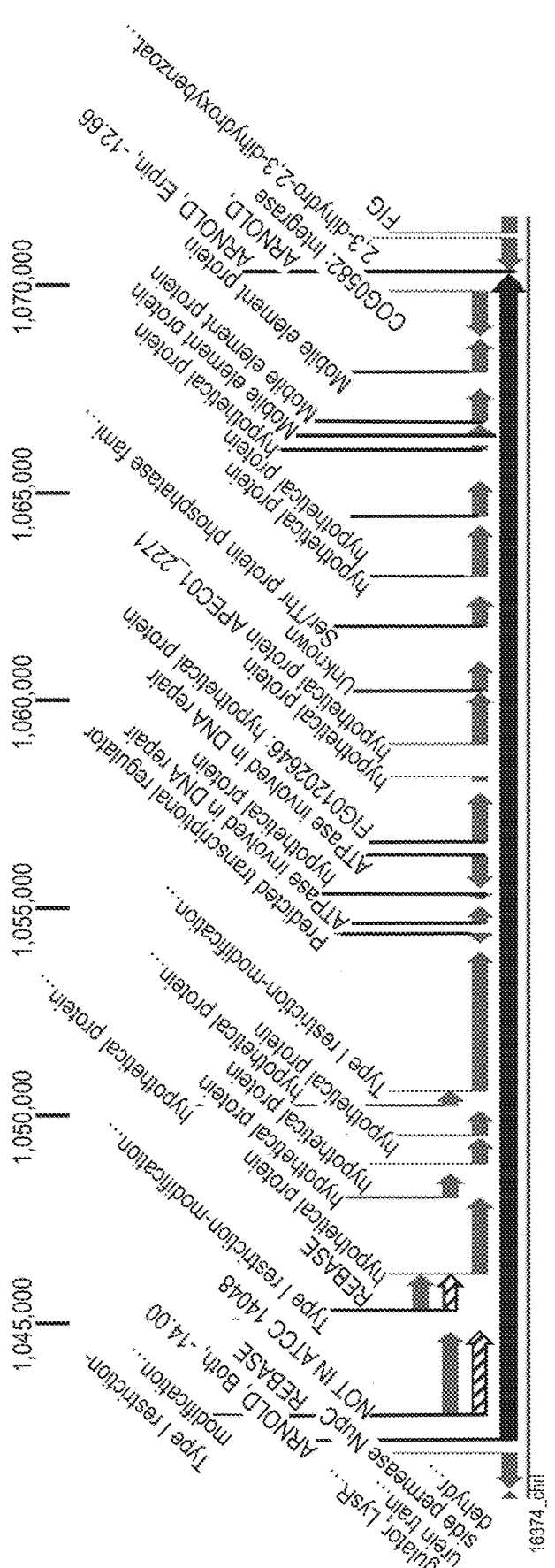
FIG. 7 shows a region of *V. natriegens* strain CCUG16374 chromosome I containing a 28 kb genetic island demarcated by the black arrow. Genes are depicted with grey arrows. The enzymes involved in the putative restriction-modification system are demarcated by striped arrows.

In this embodiment, the "knock-out/knock-in" cassette was composed simply of an antibiotic resistance gene flanked by lox sites oriented in the same direction (e.g., the orthogonal and uni-directional lox66/lox71 pair). The "knock-out/knock-in" cassette was flanked on either side by 500-750 bp of *V. natriegens* chromosomal sequence that was chosen such that the antibiotic cassette was flanked by 500-750 bp of sequence immediately upstream of the start point of the desired deletion, and 500-750 bp immediately downstream of the end point for the desired deletion. Upon successful integration via double-crossover recombination, the region of the genome to be deleted was replaced by the antibiotic cassette flanked by lox sites. The antibiotic cassette was later removed from the genome via the expression of Cre recombinase, which recombined the lox sites, thus looping the antibiotic cassette out of the chromosome (see discussion of engineering with Cre recombinase in Example 8). In some examples, we used this technique to remove the ORF for the Dns exonuclease. In another example, we used this technique to remove a 28 kb region of Chromosome I from strain CCUG 16374 harboring a putative restriction-modification system (FIG. 7).

Use of the System to Introduce Exogenous DNA into the Chromosome

In this embodiment, the "knock-out/knock-in" cassette was composed of an antibiotic resistance gene (which may or may not be flanked by lox sites oriented in the same direction) as well as additional exogenous DNA to be added into the chromosome. The "knock-out/knock-in" cassette was flanked on either side by 500 bp of *V. natriegens* chromosomal sequence that was chosen such that the "knock-in" cassette is flanked by 500 bp of sequence immediately upstream of the start point of the desired insertion, and 500 bp immediately downstream of the end point for the desired insertion. Upon successful integration via double-crossover recombination, the exogenous DNA along with the antibiotic marker was inserted into the genome at the desired location. If the antibiotic cassette is flanked by lox sites, it was later removed from the genome via the expression of Cre recombinase, which recombined the lox sites, looping the antibiotic cassette out of the chromosome (see discussion of engineering with Cre recombinase in Example 8). In some examples, we used this technique to introduce an inducible T7 RNA polymerase gene (SEQ ID NO:7) into the genome (see discussion of protein expression via an inducible T7 RNA polymerase in Example 9).

Example 8

Use of Site-Specific Recombinase to Engineer the Genome of *V. natriegens*

The use of site specific recombinases along with their target sequences was used to carry out insertions and deletions in the chromosome of *V. natriegens* and could additionally be used to carry out inversions. We have demonstrated the use of the Cre-lox system to remove sequences present in the chromosome that have been flanked by lox sites.

In Example 7 (Use of a suicide plasmid system to engineer the genome of *V. natriegens*), a chloramphenicol marker flanked by lox66 and lox71 sites (that are oriented in the same direction) was introduced into the chromosome in such a manner as to replace the entire ORF for the Dns nuclease. By expressing Cre recombinase, recombination between the lox sites resulted in the removal of the antibiotic marker from the chromosome, leaving behind a native loxP site (thus allowing us to recycle our antibiotic marker). To this end we designed the plasmid pACYCtetoriTCre, which contains:

a) the p15a origin of replication from plasmid pACYC184 b) the tetracycline resistance cassette from plasmid pJB3Tc20 c) the RK2 the RK2 origin of transfer (oriT) from pRL443 d) the temperature-inducible Cre expression cassette from plasmid 705-Cre (from Gene Bridges GmbH)

Introduction of the plasmid into the strain (carrying the lox site flanked modification) via electroporation, followed by incubation at 37° C. (to induce expression of Cre recombinase) resulted in the desired phenotype (i.e., a strain that had undergone Cre-mediated recombination to remove the antibiotic marker).

In addition to carrying out deletions, this system can be used to introduce novel DNA into a chromosome (via recombination with an exogenous circular DNA containing a lox site) and additionally or alternatively to invert regions of the chromosome (with proper orientation of the lox site).

Analogous systems are envisioned which rely on other site-specific recombinases or integrases (e.g., phiC31 integrase, bxb1 integrase, etc.).

Example 9

The Introduction of an Inducible T7 RNA Polymerase Gene into the *V. natriegens* Chromosome and its Use in Recombinant Protein Expression Using the suicide plasmid system described in Example 7, we introduced the gene for T7 RNA polymerase (SEQ ID NO:7) under the control of either a) The arabinose-inducible araBAD promoter (SEQ ID NO:5) and araC regulator protein (from *E. coli*); or b) the IPTG-inducible lac operon regulatory elements and lacI regulator protein (SEQ ID NO:6) (from *E. coli*) into the chromosome of *V. natriegens*. This system allowed for inducible, robust protein expression from a plasmid-borne gene under control of the T7 promoter.

In conjunction with the strain, we designed a plasmid known as pET325Cm-YGFP which is based off of plasmid pET28a (Novagen) and contains the YGFP fluorescent protein under the T7 promoter.

Figure 8A:
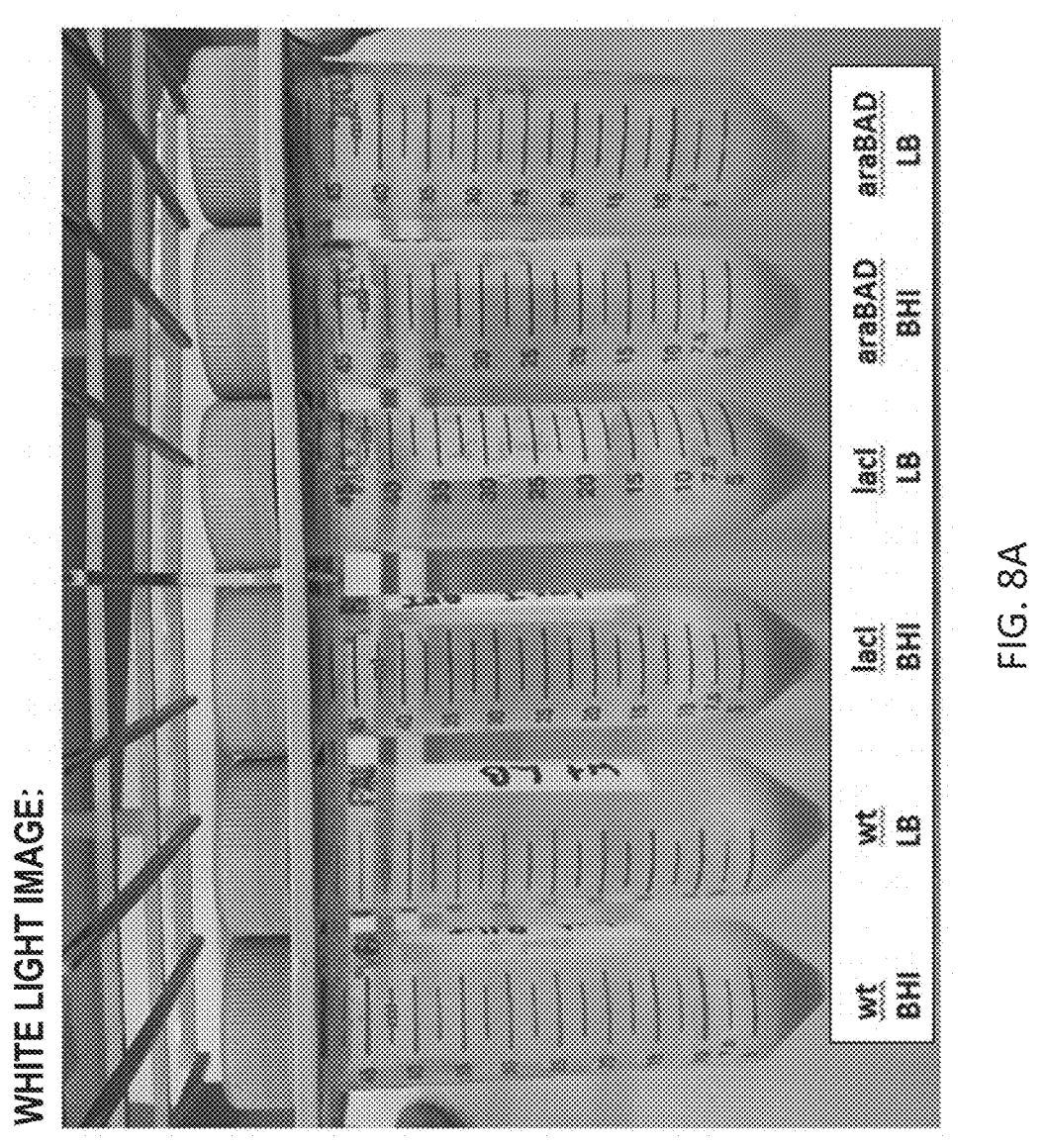
Figure 8B:
FIG. 8B) Blue light transilluminator image displaying the positive expression of GFP in the right four cultures, while the two wild type cultures on the left are not expressing GFP and therefore lack the trademark green fluorescent color.
Figure 9:
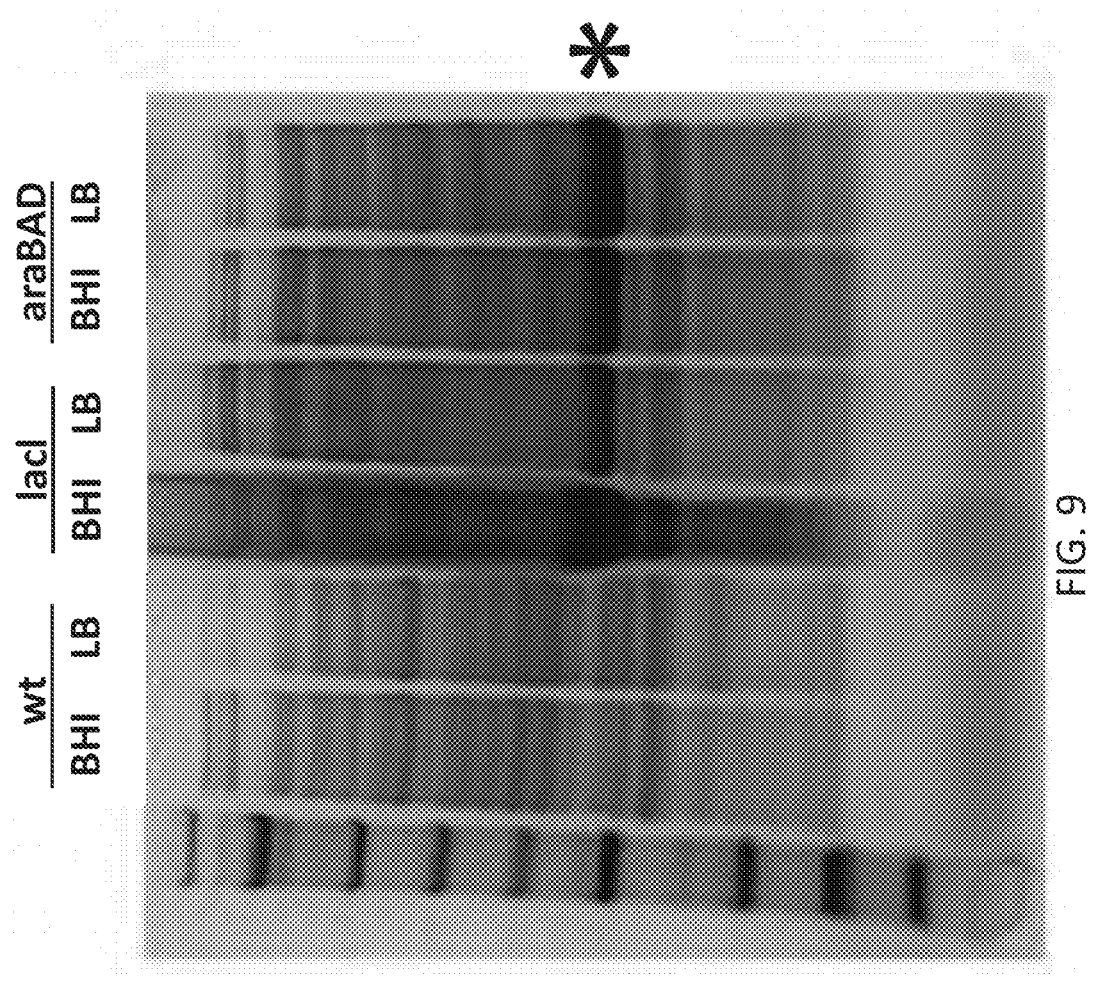
FIG. 9 shows a stained gel of bacterial lysates from wild type (two left cultures) and the indicated four strains expressing inducible GFP. The dark band demarcated with the asterisk is the GFP protein, which is only present in the engineered strains (BHI lacI, LB lacI, BHI araBAD, LB araBD), and not wild type (wt) cultures.

The plasmid was introduced into *V. natriegens* araBAD-T7 and lacI-T7 strains as well as the wild type (wt) parental strain via electroporation, as described above (Example 3). Strains harboring the plasmid were grown up overnight in Brain Heart Infusion Broth+v2 salts with 12.5 ug/mL chloraphenicol at 30° C. with shaking at 200 RPM (v2 salts means the media was supplemented with additional salts at the following concentrations: 204 mM NaCl, 4.2 mM KCl, 23.14 mM $MgCl_2$). The next day 50 mL of either LB+v2 salt media or BHI+v2 salt media with 15 μg/mL chloramphenicol in a 250 mL baffled flask was inoculated with $\frac{1}{100}^{th}$ volume of overnight culture and incubated at 30° C. When the OD600 was between 0.6 and 0.9 the cultures were induced with 1 mM IPTG (wt and lacI-t7 strains) or 1 mM IPTG+0.2% arabinose (araBAD-T7 strain). At 6.5 hrs post induction, the cultures were retrieved and the cells were harvested via centrifugation. The pellets were suspended in buffer (50 mM Tris pH 7.4, 300 mM NaCl, 5 mM imidazole) to a total volume of about 7 mL. The cells were then imaged under white light (FIG. 8A), or under a blue light transilluminator with orange filter (FIG. 8B). As can be seen in FIG. 8, the wt strain, even when induced did not make any protein. Both versions of the T7 expression system (araBAD-T7 and lacI-T7) expressed YGFP. The pellets were lysed via sonication, clarified via centrifugation, and the lysate was analyzed by SDS-PAGE (FIG. 9). The overexpressed YGFP construct is visible in the lacI-T7 and araBAD-T7 strains.

Many configurations of this system are envisioned. In some embodiments the RNA polymerase could reside on a plasmid and the gene that is to be overexpressed could be cloned into any number of vectors under control of the T7 promoter.

Analogous expression strains could be generated using other configurations of chromosomally integrated or plasmid-borne inducible RNA polymerases, relying on other RNA polymerases (e.g., SP6 RNA polymerase, etc.) or inducible promoters (e.g., other chemically inducible promoters, temperature inducible promoters, etc.)

Example 10

Chemically Competent *V. natriegens* Cells

This example provides a protocol for preparing chemically competent *V. natriegens* cells. This protocol has been used to prepare competent cells of CCUG 16364 and ATCC 14048 strains (that have a deletion of the Dns chromosomal nuclease) that achieve transformation efficiencies between $10^5$ and $10^6$ cfu/ug DNA (plasmid pACYC184).

Preparation of chemically competent cells. 10 mL of BHI+v2 salts (Brain Heart Infusion Broth supplemented with salts (204 mM NaCl, 4.2 mM KCl, and 23.14 mM $MgCl_2$)) is inoculated with a colony of *V. natriegens* (carrying a deletion of the chromosomal Dns endonuclease) from an agar plate, and incubated overnight at 30° C. with agitation at 200 RPM. On the following day, 150 mL of the same growth media is inoculated with the overnight culture at a dilution of 1:100 (overnight culture:fresh media). The culture is grown at 30° C. in a baffled flask with shaking at 200 RPM until an OD500 of 0.4. Working as quickly as possible, all subsequent steps are performed at room temperature. The culture is split into four 50 mL centrifuge tubes, and the cells are pelleted by centrifuging at 2300×g for 7 min. The supernatant is carefully removed, and each pellet is gently suspended with 5 mL of 100 mM $MgCl_2$. The cells from all four centrifuge tubes are consolidated into two centrifuge tubes, the volume of each is brought up to 30 mL with 100 mM $MgCl_2$, and the tubes are mixed by gentle inversion. Cells are pelleted by centrifuging at 2300×g for 4.5 min. The supernatant is completely removed from each tube, and the pellets are each suspended in 5 mL of 100 mM $CaCl_2$). The two suspensions are combined, and the volume adjusted to 30 mL with 100 mM $CaCl_2$. The tubes are gently mixed by inversion and then incubated at room temperature for 20 min. Following the incubation, cells are pelleted by centrifuging at 2300×g for 4.5 min. The supernatant is drawn off, each the pellets are collected in a combined volume of ~1 mL of 100 mM $CaCl_2$, transferred to a 1.5 mL Eppendorf tube, and pelleted by centrifuging at 2300×g for 1-2 min. The supernatant is removed, and the cells are resuspended in resuspension buffer (a modified version of that described by Inoue[1]: 55 mM $MnCl_2$, 15 mM $CaCl_2$, 250 mM KCl, 10 mM PIPES (from 0.5 M pH 6.7 stock), 10% glycerol (w/v), 5% PEG 8000). Cells are aliquoted into pre-chilled tubes, frozen in a dry ice bath, and are stored at −80° C. until use.

Transformation of chemically competent cells. A vial of competent cells is retrieved from storage at −80° C. and allowed to thaw on ice. Plasmid DNA and 50 μL of competent cells are combined and gently mixed in a pre-chilled 1.5 mL microfuge tube and incubated on ice for 20-30 min. During incubation, a tube for each transformation is prepared by adding 1 mL BHI+v2 salts (Brain Heart Infusion Broth supplemented with salts (204 mM NaCl, 4.2 mM KCl, and 23.14 mM $MgCl_2$)) to a culture tube and warming to 37° C. in a water bath. At the end of the ice incubation, use some of the pre-warmed media to transfer the cells out of the Eppendorf tube and into the culture tube. Let tube sit at 37° C. for 1 min. Following 1 minute at 37° C., allow the cells to recover by incubating at 30° C. for 2 hrs. with agitation at 200 RPM. Plate out dilutions of cells on pre-warmed selective plates and incubate overnight at 30° C.

Example 11

Figure 14A:
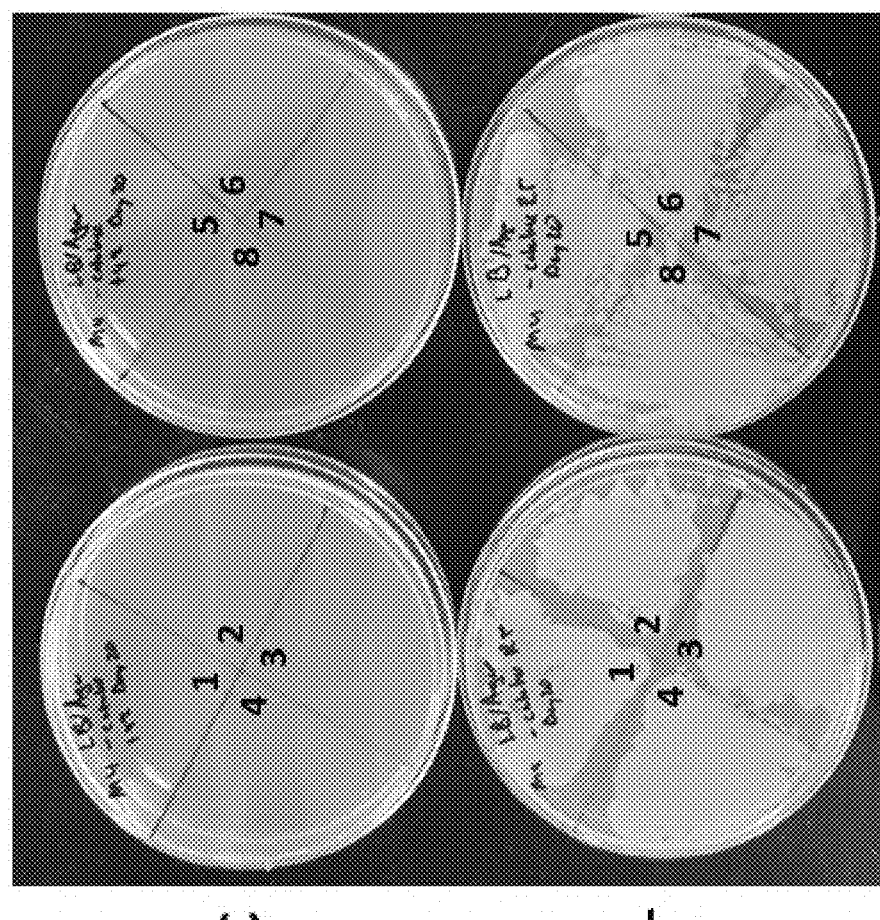
FIG. 14A is an illustration of the viability of *V. natriegens* colonies on LB agar plates stored at 4° C. vs. room temperature. The Figure demonstrates that *V. natriegens* stored as colonies on LB agar plates remain viable when stored for 20 days at room temperature, but not at 4° C. A variant of *V. natriegens* CCUG 16374 was initially streaked out on LB agar plates and incubated at either room temperature (RT) or 4° C. for 20 days. After 20 days of storage, eight colonies each from the plates stored at 4° C. (top row) and room temperature (bottom row) were streaked out on quadrants of fresh LB agar plates and incubated overnight at 30° C. No growth was observed from the eight colonies re-streaked from plates stored at 4° C. for 20 days (top row). Robust growth was observed from the eight colonies re-streaked from plates stored at RT for 20 days (bottom row).

Engineering Cold Tolerance into *V. natriegens* Via Inclusion of Heterologous Genes Storage of *V. natriegens* on solid media (LB agar) is not robust. Colonies on LB agar plates can maintain viability for at least 3 weeks at room temperature, but colonies on plates stored at 4° C. were not viable after 3 weeks (FIG. 14A).

Figure 14B:
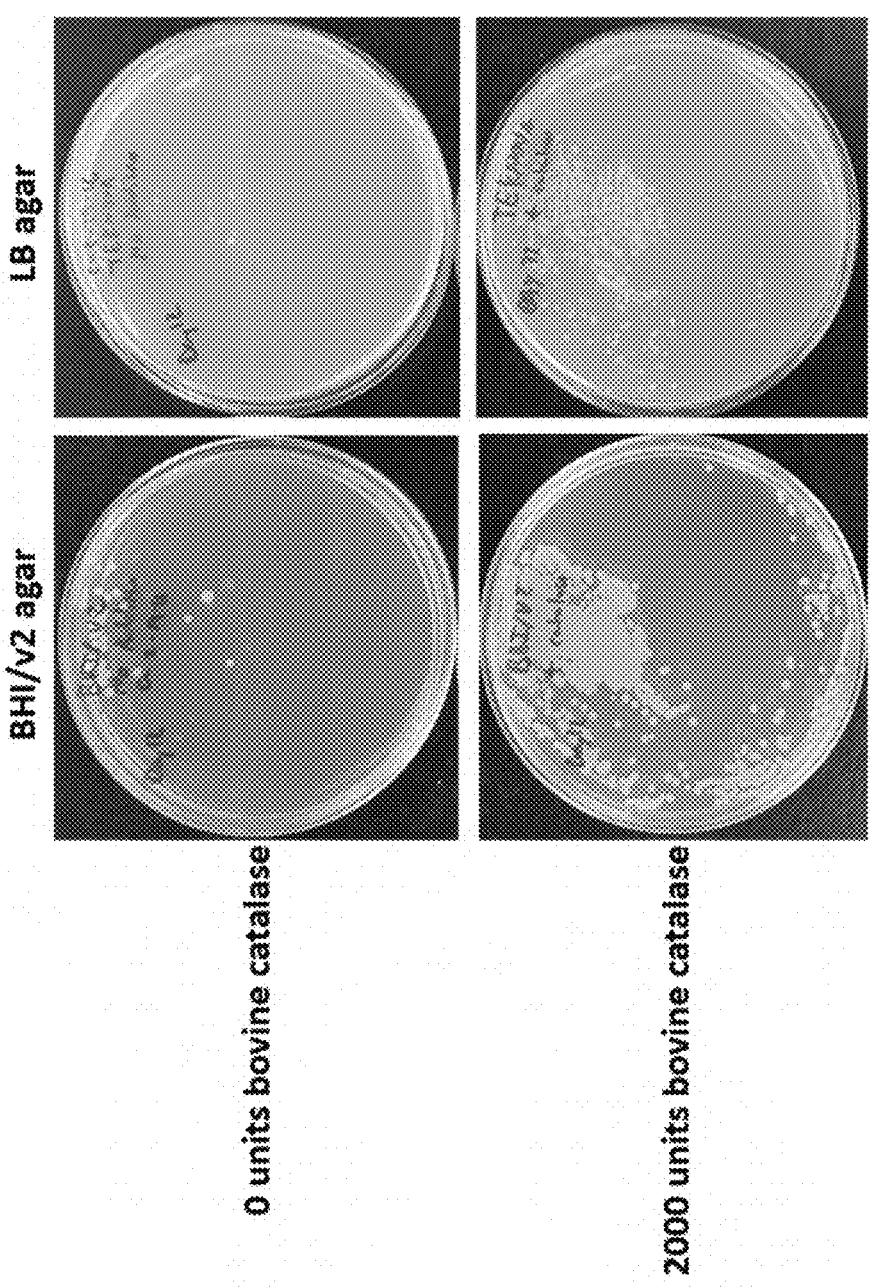
FIG. 14B demonstrates that catalase exhibits a protective effect on *V. natriegens* cells stored as colonies on agar plates at 4° C. A variant of *V. natriegens* CCUG 16374 was plated out onto an LB agar plate and incubated overnight at 30° C. This plate was then stored at 4° C. After 10 days at 4° C., a colony was streaked out on both BHI/v2 agar plates and LB agar plates with or without the addition of 2000 units of bovine catalase. The streak plates were incubated overnight at 30° C. and examined the following day. Note that plating on plates containing catalase dramatically increases the viability of cold-stored cells.
Figure 14C:
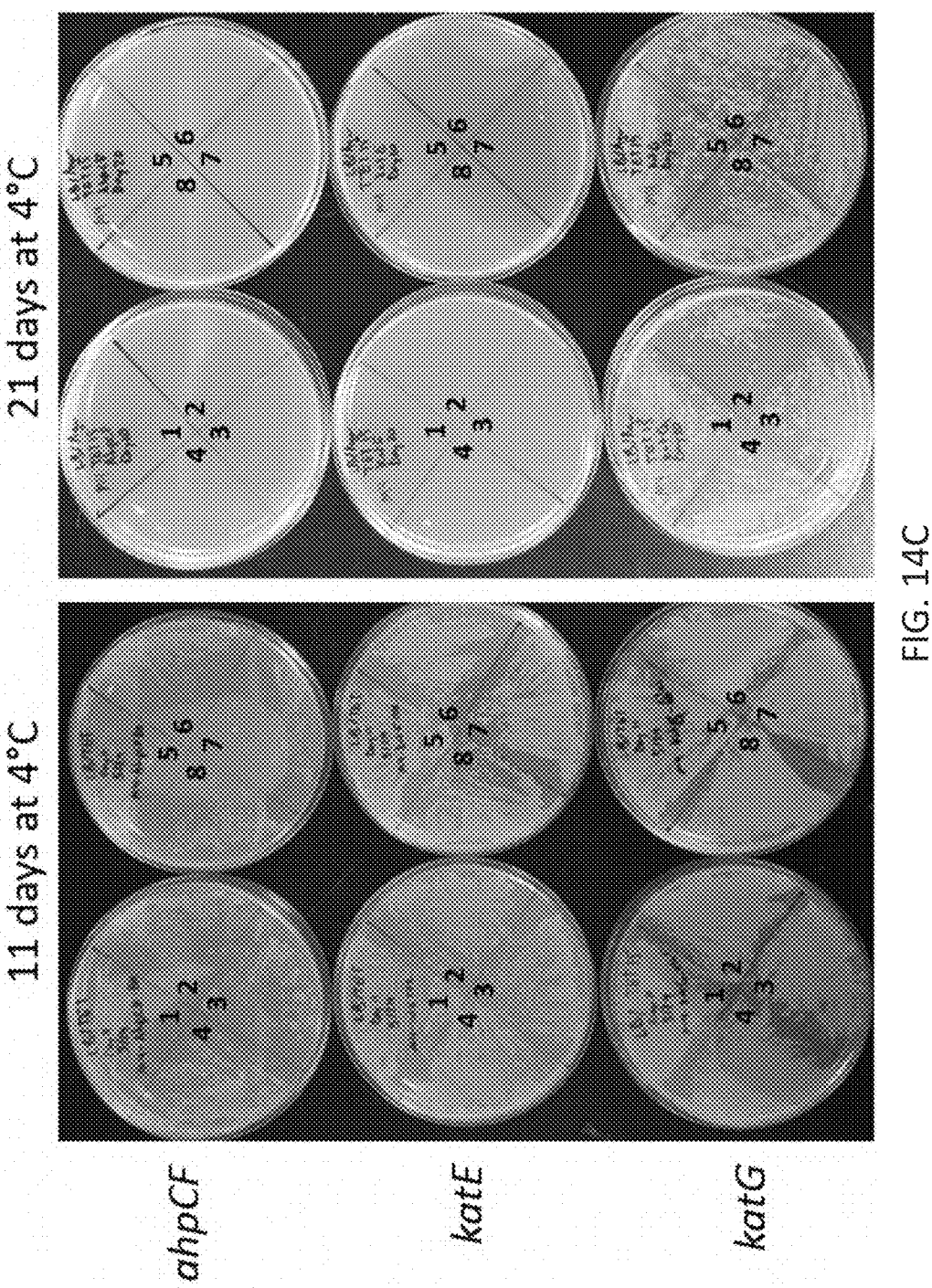
FIG. 14C demonstrates the improved tolerance to prolonged cold storage at 4° C. of a *V. natriegens* strain harboring plasmids encoding for *E. coli* ROS detoxification systems. LB+tetracycline (15 ug/mL) agar plates with colonies of a variant of *V. natriegens* (CCUG 16374) containing plasmids encoding the *E. coli* ahpCF operon, katE, or katG were stored at 4° C. for 21 days. On Day 11 and day 21, eight single colonies from each plate were picked using sterile inoculating loops and struck in quadrants on fresh LB+tetracycline (15 ug/mL) plates. The plates were incubated overnight and examined for bacterial growth. The presence of the plasmid-borne detox systems improved the viability of *V. natriegens* upon prolonged storage at 4° C., with katG having the most robust effect.

This Example illustrates that the cold tolerance of *V. natriegens* was improved by importing a heterologous ROS detoxification system from other organisms. *V. natriegens* strains carrying various ROS detoxification systems remained viable and culturable after exposure to low temperatures. *V. natriegens* having the *E. coli* alkyl hydroperoxide reductase operon (ahpCF), (katG or katE) (FIG. 14C), catalase (FIG. 14B), or glutathione S-transferase (gstA) genes (under control of heterologous promoters) on plasmids showed a marked improvement of viability over the wt cells after 11 days of cold storage, with cells carrying katG showing robust survival out to at least 3 weeks (ahpCF, katG, and katE results pictured in FIG. 14C). The inclusion of these heterologous genes on plasmids or integrated into the *V. natriegens* chromosome was therefore shown to preserve and extend the viability and culturability of cells exposed to refrigeration.

Example 12

Sucrose Induced Protein Secretion in *V. natriegens*

This Example shows the ability of a protein production host to secrete the synthesized protein directly into the growth media when induced with sucrose. *V. natriegens* strains were grown in a minimal media with a variety of different carbon sources. A minimal growth media was prepared by combining 66 mL 10× phosphate/citric acid buffer (133 g/L $KH_2PO_4$, 40 g/L $(NH_4)_2HPO_4$, 17 g/L citric acid, pH 6.3), 27.9 mL 70% glucose, 1.58 mL $MgSO_4 \cdot 7H_2O$ (500 g/L stock), 45.6 mL 5 M NaCl, and 518.92 mL $ddH_2O$. The pH was adjusted to 6.8 and the media filter sterilized. 10 ml aliquots of 10 mL of BHI+v2 salts (Brain Heart Infusion Broth supplemented with salts (204 mM NaCl, 4.2 mM KCl, and 23.14 mM $MgCl_2$)) were inoculated with either *V. natriegens* ATCC 14048 or CCUG 16374 from glycerol stocks and grown overnight at 30° C. The next day, 625 μL of each strain was used to inoculate three separate 50 ml centrifuge tubes containing 12.5 ml of the aforementioned minimal growth media. Of the three tubes for each strain, one was left as is, the second was supplemented with 0.2% (w/v) additional glucose, and the third was supplemented with 0.2% (w/v) sucrose. The three cultures for each strain were grown at 37° C. in a shaking incubator for 5 hours and 20 minutes. Cultures were spun down at 3000 rpm for 3 min at room temperature, and the supernatant was carefully drawn off and filtered through a 50 ml 0.22 uM Tube Top filter (430320). The flow-through (about 10 ml) was transferred to a 15 ml centrifuge tube. To this, 2.5 ml of 100% TCA (Trichloroacetic acid) was added, mixed by inversion, and incubated on ice for 10 min. The mixture was spun down at 7197×g at room temperature for 10 min. The resulting pellet was washed twice with 500 μl acetone, also spun at max speed for 10 min. At this point, samples were either analyzed by SDS-PAGE or submitted for 2D nano LC-MS/MS analysis.

Figure 13:
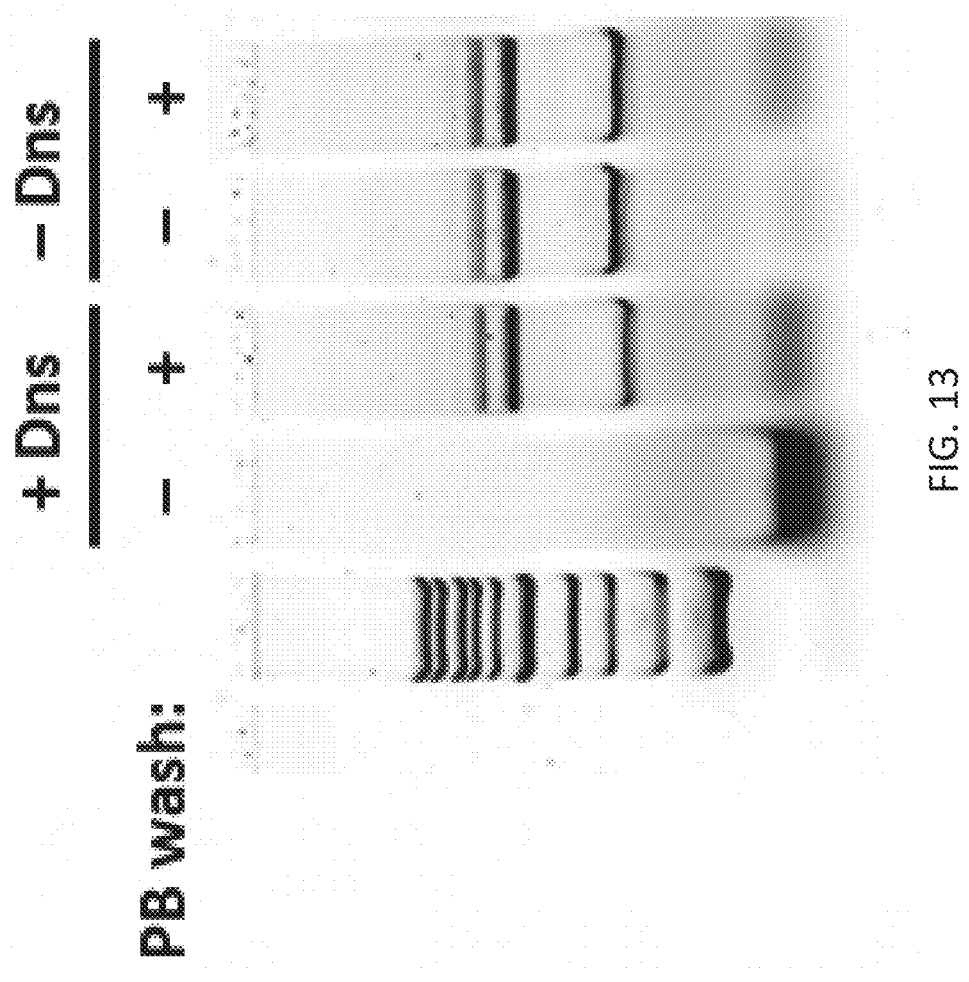
FIG. 13 is a comparison of plasmid DNA isolated from *V. natriegens* strain E with or without the endogenous Dns nuclease. Plasmid pACYC184 was isolated from strain E with or without a chromosomal deletion of Dns and purified using a commercial prep kit with or without a PB wash step. The isolated DNA was then subjected to restriction digest with NheI and analyzed by gel electrophoresis. Without the PB wash step (which removes nuclease) during plasmid isolation, the DNA is completed degraded by the Dns nuclease; however, in a nuclease deficient strain, the PB wash step was not required to preserve the integrity of the DNA.

For samples analyzed by SDS-PAGE, the tubes were placed in an 85° C. heat block for 5-10 min to remove acetone. Each pellet was then resuspended with 10 ul 4×LDS BOLT® Sample Buffer, 4 μl 10× BOLT® Sample Reducing agent and 26 μL $ddH_2O$ by pipetting up and down vigorously. Samples were heated at 85° C. for about 7 min, spun down briefly, and loaded onto BOLT® 4-12% Bis Tris Plus 10-well protein gel with MES SDS running buffer, and run at 180 V for approximately 30 min. Gels were washed and stained with Coomasie G-250 and destained O/N. Interestingly, culturing in the presence of sucrose resulted in the presence of several proteins in high concentration in the growth media (FIG. 13).

Figure 12:
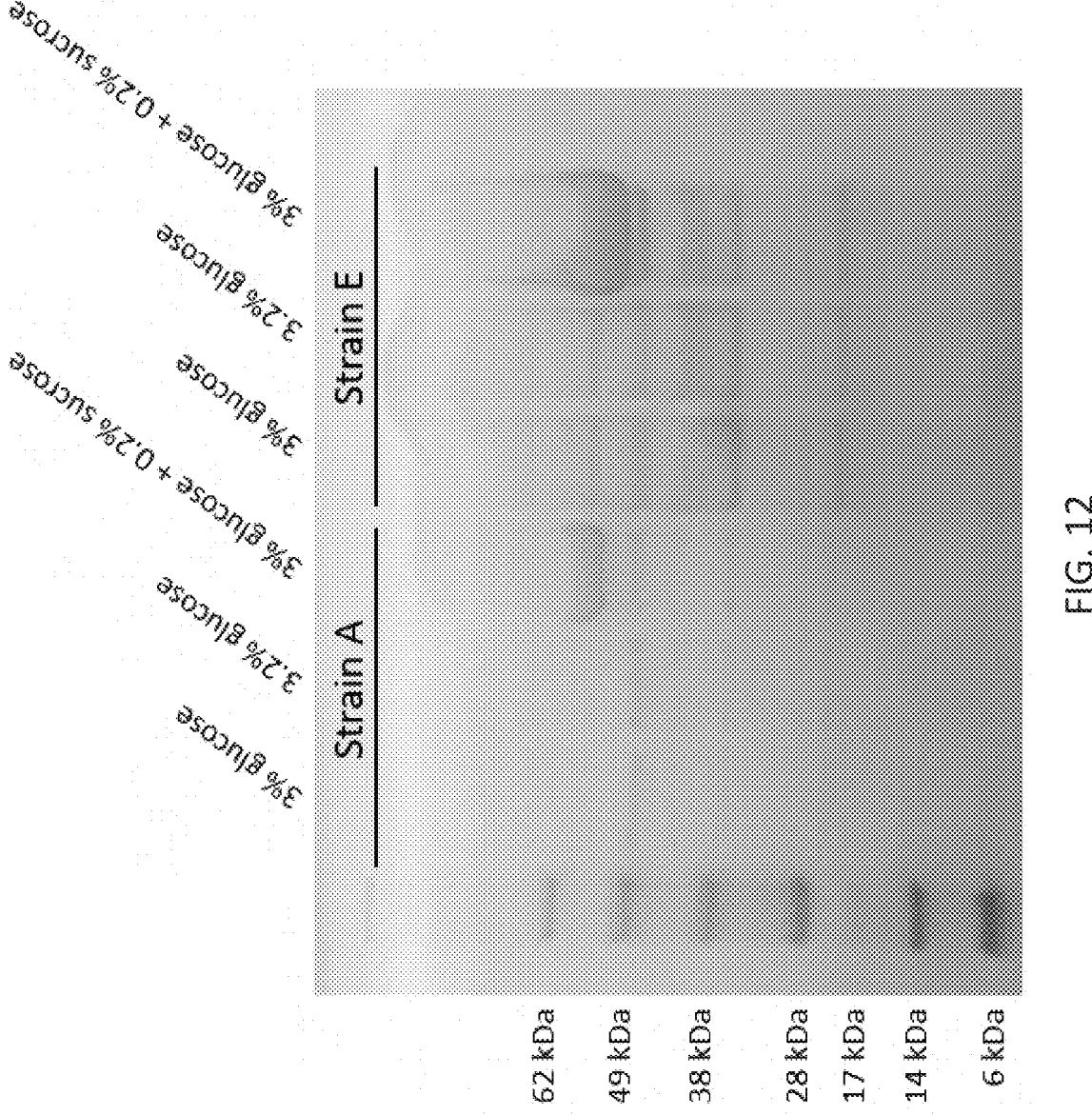
FIG. 12 is a depiction of an SDS-PAGE gel showing the secretome of *V. natriegens* strains grown on different carbon sources. When 0.2% sucrose (w/v) was spiked into a minimal media containing 3% glucose (w/v), a large protein band appeared between 49 kDa and 62 kDa.

Acetone-washed protein precipitates were subjected to 2D nano LC-MS/MS analysis. Raw MS/MS spectra were searched against a protein database for the strain prepared from the genome annotation as well as a decoy sequence database, giving a false discovery rate of <<0.1% at the peptide level. Proteomics analysis enabled positive identification of the *V. natriegens* secretome (FIG. 12). The most abundant protein identified by proteomics in the sucrose-containing media is consistent with the molecular weight of the protein identified via SDS-PAGE, and was annotated as an arabinase/levansucrase/invertase, a class of proteins known to be involved in sucrose catabolism. MS analysis revealed that the putative tag has been removed from the secreted protein during the export process. In view of these data it is seen that one can achieve recombinant protein expression by fusing these secretion tags with a recombinant protein of interest in order to direct the protein into the growth media.

Example 13

Effect of Removal of Endogenous DNs from *V. natriegens* CCUG 16374

The cellular endonuclease (Dns) in *V. natriegens* CCUG 16374 was identified and removed and found to markedly improve the quality and stability of isolated plasmid DNA. Plasmid DNA isolated from *V. natriegens* CCUG 16374 with or without the endogenous Dns nuclease is depicted in FIG. 14. Plasmid pACYC184 was isolated from CCUG 16374 with or without a chromosomal deletion of Dns and purified. The isolated DNA was then subjected to restriction digest with NheI and analyzed by gel electrophoresis. It was found that in the nuclease deficient strain, the integrity of the DNA was greatly preserved (FIG. 14).

Although the disclosure has been described with reference to the above examples, it will be understood that modifications and variations are encompassed within the spirit and scope of the disclosure. Accordingly, the disclosure is limited only by the following claims.

Example 14

Secretion of Modified Levansucrase

Figure 16:
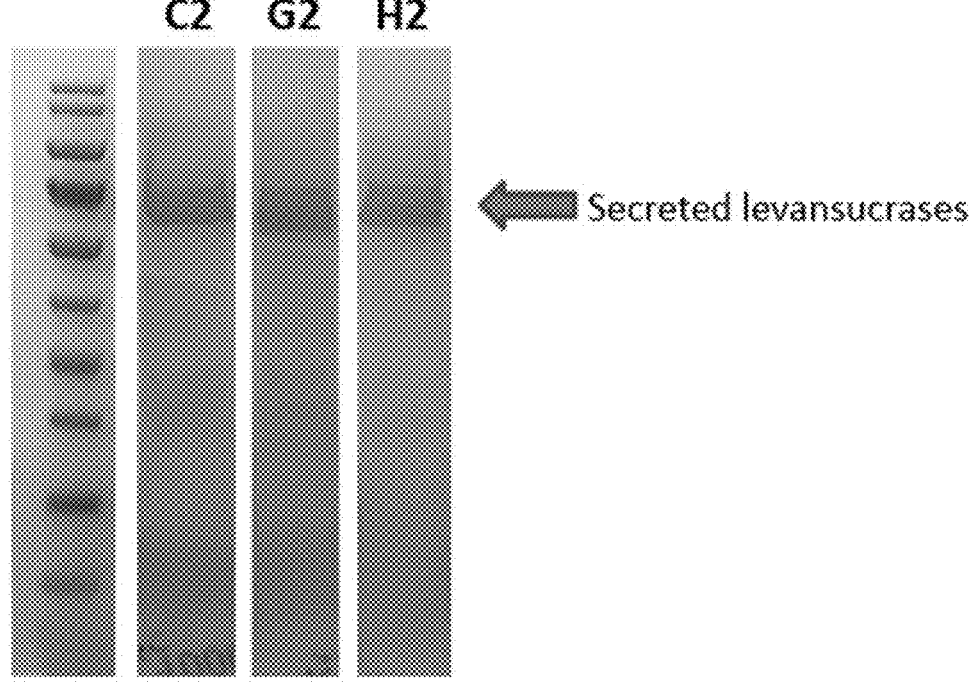
FIG. 16 provides an image of an SDS-PAGE gel of the supernatant *V. natriegens* comprising the signal sequence of SEQ ID NO: 8 fused to modified forms of the endogenous *V. natriegens* levansucrase as three recombinant constructs, C2, G2, and H2. The Figure shows all three constructs were efficiently secreted by *V. natriegens*. The molecular weight markers are (from bottom to top): 10, 15, 25, 30, 40, 50, 70, 80, 115, 140 kD.

The signal sequence of SEQ ID NO: 8 was fused to modified forms of the endogenous *V. natriegens* levansucrase as three recombinant constructs. All three constructs were efficiently secreted by *V. natriegens*, as evidenced by FIG. 16, which depicts an SDS-PAGE gel of extracellular culture supernatant.

Example 15

Periplasmic Secretion of Beta-Lactamase in *V. natriegens*

The *V. natriegens* trimethylamine-N-oxide signal sequence of SEQ ID NO: 28 was fused to the N-terminus of a variant of beta-lactamase lacking its natural N-terminal signal sequence. The construct was inserted into a pMB1 plasmid where the recombinant gene is under a lac promoter. The plasmid was introduced and conferred resistance to carbenicillin as determined by growth on LB agar plates containing carbenicillin.

Beta-lactamase confers resistance to carbenicillin only if it is successfully secreted into the periplasm of gram negative bacteria, and depends upon its natural N-terminal signal sequence for secretion. Cells carrying the recombinant plasmid described above were resistant to carbenicillin (50 ug/mL), demonstrating that the cells were successfully secreting beta-lactamase since *Vibrio* sp. does not naturally have beta lactamase.

What is claimed is:

1. A *Vibrio* sp. organism comprising
   a. a Chromosome I comprising essential genetic elements; and
   b. an altered Chromosome II comprising at least one piece of exogenous DNA of greater than 10 kb in size that encodes at least one heterologous protein or peptide; and
   c. wherein the organism comprises all cellular components functional for the replication and amplification of the altered Chromosome II, and the altered Chromosome II is replicated during cellular growth of the organism.

2. The organism of claim 1 wherein Chromosome II comprises SEQ ID NO: 1 or a variant thereof having at least 90% sequence identity to SEQ ID NO: 1.

3. The organism of claim 2 wherein the at least one piece of exogenous DNA comprised on the altered Chromosome II is greater than 50 kb in size.

4. The organism of claim 2 wherein the at least one piece of exogenous DNA comprised on the altered Chromosome II is greater than 100 kb in size.

5. The organism of claim 1 further comprising an additional vector encoding at least one origin of replication and at least one selection marker.

6. The organism of claim 5 comprising tetA/tetR or chloramphenicol resistance genes, an R6Kgamma origin of replication, and further comprising an RP4 oriT region.

7. The organism of claim 1 wherein at least one essential genetic element removed from Chromosome II is comprised on Chromosome I.

8. The organism of claim 1 wherein the *Vibrio* sp. is *Vibrio natriegens*.

9. The organism of claim 1 wherein the altered Chromosome II comprises an inducible promoter.

10. The organism of claim 9 wherein the inducible promoter is selected from the group consisting of: the IPTG inducible trc promoter, the temperature inducible lambda pR promoter, and arabinose inducible araBAD promoter.

11. The organism of claim 1 further comprising that Chromosome I or Chromosome II comprise at least one deletion of a gene encoding a protein selected from the group consisting of: a recombinase, an endonuclease, a protease, and a restriction enzyme.

12. The organism of claim 11 wherein the recombinase is recA and the endonuclease is Dns.

* * * * *

SEQUENCE LISTING

<160> NUMBER OF SEQ ID NOS: 28

<210> SEQ ID NO 1
<211> LENGTH: 5544
<212> TYPE: DNA
<213> ORGANISM: Vibrio natriegens

<400> SEQUENCE: 1

```
aacaactggc ataaaaaaac cgcccgaagg cggttgaagt tttgattaac gttattgcaa        60
tttgctgtga acaaaagcaa gaatttcttc catcaaacta tcatctactt ttttaaggtt       120
cagtgccaga ttactgcctt tgcggctgta actcgcgcga cctttatca aatcgacttt       180 gtctaccttt ggcgatggtt tggctggtga taattcagta atccaacttt ctaggctttc       240
tgtgacttct tttgttagac gagcaacacc ttgcgctgtg ctacgctgcc acaagtatcc       300
gtctgttgta cggcatttat ctaacaaccc ttgctgatgt tcagggctta gattcgtaaa       360
ctgcttgtgc aatttaacaa tggttgggcg accaaggtcg ccaacatttg gatacgcttg       420
aagcaactct agtggtaaag aagccgcttt taacgctcca cttaccaatg cctcactgca       480
ttggaacatt ttcgccagcg ctttctggtc ttctgcttca ccgctgtcta acttggcttg       540
catctccttg cctttttcat aaagagagag aggcttgtga gcgtttgcca catcagacag       600
gaacttagca tgattagagt taatgttgtc gccaacataa accagaaaat cttgctcagc       660
cagaatacaa gatttacgac gacgactacc gtctaatacc tcaatcttgc catcttcagt       720
gcgacggccg acggccggat actgctgacc acgctctttt aacgtaacca atacatcgga       780
taaagcatgc tcattcaaga aagattgttc gcgtgcgtta tcaacaaaga ctgtcgtttc       840
agactcaacc ttgtcagcag gaatacgaac caactcgaat tgaacggtat tctcaccagc       900
gaccgctaac tcaatggttt gcgttttttc ttttgcagcg gtttgcgctt cttgaggcgt       960
agccacgcgg cgtttattag ttttgccaaa taattttgcg tttaattcag acgttttcaa      1020
agccatttac ttattacccc tgattcaatg acggccaatt agagtgcaat acacgctcta      1080
gttcaagtgc gctcttatga acggcgtctt gagcggttgc gagcgttttc ttaccacctt      1140
caaaatcact cacagtgaga tcaaataccg tactgtaggt gtcagcacag gtttcaaacg      1200
ctcgactacg cggaatggta gccatcataa cttggtcacc tagaagatag ttcatttcag      1260
ttaaaacaga aacttgcttc ttattgtcgt cctcaaacat ggttggcatt aagcgcacaa      1320
actcaaggcc attccaatct tctgggaaca tttcatacac tgtcggtaag tgttggaaaa      1380
agtttaccgt tgaagcccag tcaagacgtt tggcagcaca tggaatcagc aatgcgttag      1440
aagcatacat tgcattccaa actagcggat ccacgtgcgg gccggtatca atcatgatga      1500
tatcgaaatc atctgcaata atgtcgataa gctgctcttt aacaaacgc acgatatcta      1560 aagatgggtc ttcagataag gtttgccacg cttcggcatt aaacatcgcg tcttctggga      1620
aagcagagat tgacttcaag tttggatatt gcgtaggtag caatacattc ttatgcaaaa      1680
actcactatc aatctcaaca ccgtctggta cgttacctaa cataatatca acggcagaat      1740
agatattatc gtgttcagcg acactgattt gtgggtttag gaatagacgt aatgagcctt      1800
gtggatctaa gtcaatcaaa caaatacggt agcgtttatc taagttaagc gctaaacaag      1860
ccgctaaatg caccgccgac atcgatttac ccgtaccacc ctttttggttt tgtacgttga      1920 taatccacgg cttattgcca ttgtttttttt tacgctcgtg gaatttaggc acctcagccg      1980
catccatcag catatgtgct tcttctaacg taatggaata atgattggcg ttattctttg      2040
taaattgatg gccagcggct tccattttac caatcgcgtc atcgagtttt cgacgagtca      2100
```

-continued

```
aacccgatcg ggtttccatc attgccttag acattggagg gaagtagttg tcacttcgct      2160
cttccaaaac aatctcaata cggtcagctt gaacttgttg tgtgagttct gctaactcat      2220
gaagattttc aatcgttttt tctcttttca tgccaatttc cgttgaaagg atatctgatt      2280
gcaattgtac agcagtgaac accaataaca acaaaaaggt gcacaaacat tttgaataac      2340
aatcacatat aaaaacaata aaatcgactc ttttatgaat tatggtaaaa aatatatcaa      2400
aatataatca aacaagttcg cacaaacgct ttgctaactc tataaattaa aagtgttaca      2460
gcgtcacaca tttacattgt aaattaaaaa ttatacggaa cgattatatt gaccggctaa      2520
attacggatt atgtaaaatc aacatgttta caacaaaaaa tgcagaaacg gggacaagat      2580
tcattcacgg ataccctctt gatcatgctt ccaaagcatt tgaggccgtt tttttaatag      2640
atggaccgga aagatgatca agagagttac ttgatcatct ttccgtgtta tatcctactt      2700
acgaaagcat gatcatggca aaagtagggg agtgcatgag tagatggacg ttattctatg      2760
cgatcaaacc atcggaaaaa tgatcaagtg aataggtttc tcggaagcat gctttttact      2820
cgccatttta cggacgaatg cagatatact ggggcattca gagaatcaag cgtaaacaaa      2880
cctcggaacg atgaaataaa aacatggtat ttgataagta cggctatcat gatcatgctt      2940
cctaaattta gaacagatat aggatttaca cgcttagtac tgatatctga tgatattttc      3000
agcacatgaa taaattaccg ccgaaatgag actttaactt ggcattaacg ctactcttga      3060
tcatcgatcc ggaaccaagg aggcgataaa atccatggtg tttacacctt tgttgatcaa      3120
gcaaacccgc atttctgtgg ataacctgta caaatgtcat gatcatcgtt tcaagaccat      3180
tttgatcatc ttttcagaaa cttaatgatc atgcttacga gaggatatga tcatgctttc      3240
aagatattgt tgatcatcgt ttcgttatat tcatgatcat ggttccgaaa gggatttcaa      3300
taattccttt ttataacaac aacttaaaat gataaaaatt gccagatcaa tagatcatat      3360
aatcaattaa gatcagaata atcaaaaaga tcagttattt aaaaaacaag attttttctt      3420
tatttatgat ctgtttttct ttattcttcg gaaccatagc acaactacgg ctagtgtgat      3480
ctggatctaa aatgatggct gatgaaaaaa ttctgattaa agcaccaaga agccacaaag      3540
acgggcatct ttttgaagtg cacgaatctt ctgcagattg ggtagaacaa taccaacact      3600
tcaaaggggt gaccaaaagc atcttagaat tgcttaatct gatctcgttg agaggtttca      3660
gcagcaaaga tggacttgta tcaaccactg aaatcgttga agcaacagat ggtcaactga      3720
ctcgtgctgc gttacaacaa cgattacgag cagcggtgaa cattggttta tttacgcaaa      3780
ctccagttcg ctttgaagaa ggactggcag gtaaaaccat gcttcacacg tttgttaatc      3840
ccaataagct catttccgct ttgggtgcaa cgagcttagt tactgaaaaa gtccgccaga      3900
atgaaaaaca aaaacgctca aaagcactag ctcagacgca agtaaacaaa cgcttgctga      3960
cagaacatgg cttaaacacg ccgccgacga tgaaagatga agcggatcaa ttcgtcgtct      4020
ctccaactaa ttgggcaggg atcattgacc aagctttggc gccaccacgt actcgtaaga      4080
gttatcagaa gtcgatggtg tcgatctctg gtacgaaagc ggtaatagaa actcgatcgt      4140
caaaaaatat catgacagtc gatgatctga tgaccttgtt tgcgctgttt accctgaccg      4200
tgcaatacca tgatcatcac aaagatcagt accatcttga tgcagctcat gtaccgaata      4260
aaacaccgct gtatatcacc gacatcctgt cattgcgtgg caaaaaggac agtggacctg      4320
ctcgtgattc cattcgtgac agtatcgata gaatcgaatt caccgacttc cagttacatg      4380
agcttacagg ccgctggtta agtgaaaaca tgccggaagg ttttaaaagt gatcgattcc      4440
```

-continued

```
gctttctagc gcgaacgatc accgcatcag aagaagcgcc agttgagggc agcgacggtg    4500
agatccgaat caaacctaat ttgtacatat tggtttggga gccgtcgttt tacgaggaat    4560
tactgactcg tgattacttc ttcctgtttc cgccagagat tctgaaacaa catactttgg    4620
tgttccagtt atattccttt ttccgtagcc ggatggttcg tcgccatacg gattgtatgt    4680
tgcttagtga actgaatcag aagttagcgc gtaacatcga gtggcgtcga ttctccatgg    4740
atcttatccg ggaactgaaa cgattatctg atggaaaagg gacggaagat cttttttgttg    4800 ttaacttatg gggctaccac ctgacgatcg aaaccatgat cgagaaaggc aaaatcatgg    4860
attaccagat cgatatcaag tgtgatgttg aggaagtctt gcgttattca cgtgctcgta    4920
ccacaaacgc aggaaagcgt aacatggctc ctacgctgcc aaacccactt cgtaatgaga    4980
tggtatccaa acaacagcta gaagagctct caggcatcat tgacggcgaa tttgagccta    5040
ttcagcgcaa agcaccgtct cctcgtggta atttagggcg taggatcaag caaagaaaac    5100
atctggttga gattaatgca gatgaaatta ccattactct atccaaatat acctcaccag    5160
aggctctgga acgcagcata acggcgttat cagcaatgac agggcactca tacgcctcga    5220
ttaaggaaga gtgctctgag tacattgaga agcttgattg gttaagagtt ggagatgacc    5280
cattacctta tgagactctg agtaagaccg ttgagctgtt caatacgcaa aatgatctca    5340
aacatcttac tattgagcgt ctgattgccg gtttagctgt tcgtcgcaag gtctgcagac    5400
aaatttatga tggccatatg gatgagatgg tgtatcgagc tcttgatgaa atggcgattt    5460
aacatcattc agctttatga attgaaaccg attaatgtga ctgattgatt ttaaatgtaa    5520
atatatattt cgataataga aaac                                          5544
```

```
<210> SEQ ID NO 2
<211> LENGTH: 799
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: R6Ky origin of replication

<400> SEQUENCE: 2
```

```
caaccatcat cgatgaattg cttcgttaat acagatgtag gtgttccaca gggtagccag      60
cagcatcctg cgatgcagat ccggatgcca tttcattacc tctttctccg cacccgacat     120
agatccgaag atcagcagtt caacctgttg atagtacgta ctaagctctc atgtttcacg     180
tactaagctc tcatgtttaa cgtactaagc tctcatgttt aacgaactaa accctcatgg     240
ctaacgtact aagctctcat ggctaacgta ctaagctctc atgtttcacg tactaagctc     300
tcatgtttga acaataaaat taatataaat cagcaactta atagcctct aaggtttttaa     360 gttttataag aaaaaaaaga atatataagg cttttaaagc ttttaaggtt taacggttgt     420
ggacaacaag ccagggatct gccatttcat tacctctttc tccgcacccg acatagatcc     480
ggaacataat ggtgcagggc gctgacttcc gcgtttccag actttacgaa acacggaaac     540
cgaagaccat tcatgttgtt gctcaggtcg cagacgtttt gcagcagcag tcgcttcacg     600
ttcgctcgcg tatcggtgat tcattctgct aaccagtaag gcaaccccgc cagcctagcc     660
gggtcctcaa cgacaggagc acgatcatgc gcacccgtgg ccaggaccca acgctgcccg     720
agatgcgccg cgtgcggctg ctggagatgg cggacgcgat ggatatgttc tgccaagggt     780
tggtttgcgc attcacagg                                                 799
```

-continued

```
<210> SEQ ID NO 3
<211> LENGTH: 2727
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: tetA/tetR resistance genes + RP4 oriT

<400> SEQUENCE: 3
ccgtcgatct atctcatctg cgcaaggcag aacgtgaaga cggccgccct ggacctcgcc      60
cgcgagcgcc agcgcacgag gccggcgcgc ggacccgccg cggcccacga gcggacgccg     120
cagcaggagc gccagaaggc cgccagagag gccgagcgcg gcgtgaggct tggacgctag     180
ggcagggcat gaaaaagccc gtagcgggcg ctacgggggt ctgacgcggt ggaaaggggg     240
aggggatgtt gtctacatgg ctctgctgta gtgagtgggt tgcgctccgg cagcggtcct     300
gatcaatcgt caccctttct cggtccttca acgttcctga caacgagcct ccttttcgcc     360
aatccatcga caataccgc gagtccctgc tcgaacgctg cgtccggacc ggcttcgtcg     420
aaggcgtcta tcgcggcccg caacagcggc gagagcggag cctgttcaac ggtgccgccg     480
cgctcgccgg actcgctgtc gccggcctgc tcctcaagca cggccccaac agtgaagtag     540
ctgattgtca tcagcgcatt gacggcgtcc ccggccgaaa aacccgcctc gcagaggaag     600
cgaagctgcg cgtcggccgt ttccatctgc ggtgcgcccg gtcgcgtgcc ggcatggatg     660
cgcgcgccat cgcggtaggc gagcagcgcc tgcctgaagc tgcgggcatt cccagtcaga     720
aatgagcgcc agtcgtcgtc ggctctcggc accgaagtgc tatgattctc cgccagcatg     780
gcttcggcca gtgcgtcgag cagcgcccgc ttgttcctga agtgccagta aagcgccggc     840
tgctgaaccc ccaaccgttc cgccagtttg cgtgtcgtca gaccgtctac gccgacctcg     900
ttcaacaggt ctagggcggc acggatcact gtattcggct gcaactttgt catgcttgac     960
actttatcac tgataaacat aatatgtcca ccaacttatc agtgataaag aatccgcgcg    1020
ttcaatcgga ccagcggagg ctggtccgga ggccagacgt gaaacccaac atacccctga    1080
tcgtaattct gagcactgtc gcgctcgacg ctgtcggcat cggcctgatt atgccggtgc    1140
tgccgggcct cctgcgcgat ctggttcact cgaacgacgt caccgcccac tatggcattc    1200
tgctggcgct gtatgcgttg gtgcaatttg cctgcgcacc tgtgctgggc gcgctgtcgg    1260
atcgtttcgg cggcggcca atcttgctcg tctcgctggc cggcgccact gtcgactacg    1320
ccatcatggc gacagcgcct ttcctttggg ttctctatat cgggcggatc gtggccggca    1380
tcaccggggc gactggggcg gtagccggcg cttatattgc cgatatcact gatggcgatg    1440
agcgcgcgcg gcacttcggc ttcatgagcg cctgtttcgg gttcgggatg gtcgcgggac    1500
ctgtgctcgg tgggctgatg ggcggttttct ccccccacgc tccgttcttc gccgcggcag    1560
ccttgaacgg cctcaatttc ctgacgggct gtttcctttt gccggagtcg cacaaaggcg    1620
aacgccggcc gttacgccgg gaggctctca acccgctcag cttcgttcgg tgggcccggg    1680
gcatgaccgt cgtcgccgcc ctgatggcgg tcttcttcat catgcaactt gtcggacagg    1740
tgccggccgc gctttgggtc attttcggcg aggatcgctt tcactgggac gcgaccacga    1800
tcggcatttc gcttgccgca tttggcattc tgcattcact cgcccaggca atgatcaccg    1860
gccctgtagc cgcccggctc ggcgaaaggc gggcactcat gctcggaatg attgccgacg    1920
gcacaggcta catcctgctt gccttcgcga cacggggatg gatggcgttc ccgatcatgg    1980
```

-continued

```
tcctgcttgc ttcgggtggc atcggaatgc cggcgctgca agcaatgttg tccaggcagg   2040
tggatgagga acgccagggg cagctgcaag gctcactggc ggcgctcacc agcctgacct   2100
cgatcgtcgg acccctcctc ttcacggcga tctatgcggc ttctataaca acgtggaacg   2160
ggtgggcatg gattgcaggc gctgccctct acttgctctg cctgccggcg ctgcgtcgcg   2220
ggctttggag cggcgcaggg caacgagccg atcgctgatc gtggaaacga tagggacgga   2280
tctgctggcg aaaggggggat gtgctgcaag gcgattaagt tgggtaacgc cagggttttc   2340
ccagtcacga cgttgtaaaa cgacggccag tgaattaatt cttgaagacg aaagggcctc   2400
gtgatacgcc tattttttata ggttaatgtc atgataataa tggtttctta gagcttacgg   2460
ccagcctcgc agagcaggat tcccgttgag caccgccagg tgcgaataag ggacagtgaa   2520
gaaggaacac ccgctcgcgg gtgggcctac ttcacctatc ctgcccggct gacgccgttg   2580
gatacaccaa ggaaagtcta cacgaaccct ttggcaaaat cctgtatatc gtgcgaaaaa   2640
ggatggatat accgaaaaaa tcgctataat gaccccgaag cagggttatg cagcggaaaa   2700
gatccgtcga tcgacccagg tggcact                                       2727
```

```
<210> SEQ ID NO 4
<211> LENGTH: 11285
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pVnatCII-YACTRP-copycontrol

<400> SEQUENCE: 4
```

```
agcttacggc cagcctcgca gagcaggatt cccgttgagc accgccaggt gcgaataagg     60
gacagtgaag aaggaacacc cgctcgcggg tgggcctact tcacctatcc tgcccggctg    120
acgccgttgg atacaccaag gaaagtctac acgaaccctt tggcaaaatc ctgtatatcg    180
tgcgaaaaag gatggatata ccgaaaaaat cgctataatg accccgaagc agggttatgc    240
agcggaaaag atccgtcgat cgacccaggt ggcactaaca actggcataa aaaaaccgcc    300
cgaaggcggt tgaagttttg attaacgtta ttgcaatttg ctgtgaacaa agcaagaat    360 ttcttccatc aaactatcat ctactttttt aaggttcagt gccagattac tgcctttgcg    420
gctgtaactc gcgcgacctt ttatcaaatc gactttgtct acctttggcg atggtttggc    480
tggtgataat tcagtaatcc aactttctag gctttctgtg acttctttttg ttagacgagc    540 aacaccttgc gctgtgctac gctgccacaa gtatccgtct gttgtacggc atttatctaa    600
caacccttgc tgatgttcag ggcttagatt cgtaaactgc ttgtgcaatt taacaatggt    660
tgggcgacca aggtcgccaa catttggata cgcttgaagc aactctagtg gtaaagaagc    720
cgcttttaac gctccactta ccaatgcctc actgcattgg aacattttcg ccagcgcttt    780
ctggtcttct gcttcaccgc tgtctaactt ggcttgcatc tccttgcctt tttcataaag    840
agagagaggc ttgtgagcgt ttgccacatc agacaggaac ttagcatgat tagagttaat    900
gttgtcgcca acataaacca gaaaatcttg ctcagccaga atacaagatt tacgacgacg    960
actaccgtct aatacctcaa tcttgccatc ttcagtgcga cggccgacgg ccggatactg   1020
ctgaccacgc tctttttaacg taaccaatac atcggataaa gcatgctcat tcaagaaaga   1080
ttgttcgcgt gcgttatcaa caaagactgt cgtttcagac tcaaccttgt cagcaggaat   1140
acgaaccaac tcgaattgaa cggtattctc accagcgacc gctaactcaa tggtttgcgt   1200
```

-continued

```
ttttttctttt gcagcggttt gcgcttcttg aggcgtagcc acgcggcgtt tattagtttt      1260
gccaaataat tttgcgttta attcagacgt tttcaaagcc atttacttat tacccctgat      1320
tcaatgacgg ccaattagag tgcaatacac gctctagttc aagtgcgctc ttatgaacgg      1380
cgtcttgagc ggttgcgagc gttttcttac caccttcaaa atcactcaca gtgagatcaa      1440
ataccgtact gtaggtgtca gcacaggttt caaacgctcg actacgcgga atggtagcca      1500
tcataacttg gtcacctaga agatagttca tttcagttaa aacagaaact tgcttcttat      1560
tgtcgtcctc aaacatggtt ggcattaagc gcacaaactc aaggccattc caatcttctg      1620
ggaacatttc atacactgtc ggtaagtgtt ggaaaaagtt taccgttgaa gcccagtcaa      1680
gacgtttggc agcacatgga atcagcaatg cgttagaagc atacattgca ttccaaacta      1740
gcggatccac gtgcgggccg gtatcaatca tgatgatatc gaaatcatct gcaataatgt      1800
cgataagctg ctctttttaac aaacgcacga tatctaaaga tgggtcttca gataaggttt      1860
gccacgcttc ggcattaaac atcgcgtctt ctgggaaagc agagattgac ttcaagtttg      1920
gatattgcgt aggtagcaat acattcttat gcaaaaactc actatcaatc tcaacaccgt      1980
ctggtacgtt acctaacata atatcaacgg cagaatagat attatcgtgt tcagcgacac      2040
tgatttgtgg gtttaggaat agacgtaatg agccttgtgg atctaagtca atcaaacaaa      2100
tacggtagcg tttatctaag ttaagcgcta aacaagccgc taaatgcacc gccgacatcg      2160
atttacccgt accaccctttt tggttttgta cgttgataat ccacggctta ttgccattgt      2220
tttttttacg ctcgtggaat ttaggcacct cagccgcatc catcagcata tgtgcttctt      2280
ctaacgtaat ggaataatga ttggcgttat tctttgtaaa ttgatggcca gcggcttcca      2340
ttttaccaat cgcgtcatcg agttttcgac gagtcaaacc cgatcgggtt tccatcattg      2400
ccttagacat tggagggaag tagttgtcac ttcgctcttc caaaacaatc tcaatacggt      2460
cagcttgaac ttgttgtgtg agttctgcta actcatgaag atttttcaatc gttttttctc      2520 tttttcatgcc aatttccgtt gaaaggatat ctgattgcaa ttgtacagca gtgaacacca      2580
ataacaacaa aaaggtgcac aaacattttg aataacaatc acatataaaa acaataaaat      2640
cgactctttt atgaattatg gtaaaaaata tatcaaaata taatcaaaca agttcgcaca      2700
aacgctttgc taactctata aattaaaagt gttacagcgt cacacattta cattgtaaat      2760
taaaaattat acggaacgat tatattgacc ggctaaatta cggattatgt aaaatcaaca      2820
tgtttacaac aaaaaatgca gaaacgggga caagattcat tcacggatac cctcttgatc      2880
atgcttccaa agcatttgag gccgttttttt taatagatgg accggaaaga tgatcaagag      2940
agttacttga tcatctttcc gtgttatatc ctacttacga aagcatgatc atggcaaaag      3000 tagggagtg catgagtaga tggacgttat tctatgcgat caaaccatcg gaaaaatgat      3060
caagtgaata ggtttctcgg aagcatgctt tttactcgcc attttacgga cgaatgcaga      3120
tatactgggg cattcagaga atcaagcgta aacaaacctc ggaacgatga aataaaaaca      3180
tggtatttga taagtacggc tatcatgatc atgcttccta aatttagaac agatatagga      3240
tttacacgct tagtactgat atctgatgat attttcagca catgaataaa ttaccgccga      3300
aatgagactt taacttggca ttaacgctac tcttgatcat cgatccggaa ccaaggaggc      3360
gataaaatcc atggtgttta cacctttgtt gatcaagcaa acccgcattt ctgtggataa      3420
cctgtacaaa tgtcatgatc atcgtttcaa gaccattttg atcatctttt cagaaactta      3480
atgatcatgc ttacgagagg atatgatcat gctttcaaga tattgttgat catcgtttcg      3540
ttatattcat gatcatggtt ccgaaaggga tttcaataat tccttttttat aacaacaact      3600
```

```
taaaatgata aaaattgcca gatcaataga tcatataatc aattaagatc agaataatca    3660
aaaagatcag ttatttaaaa aacaagattt tttctttatt tatgatctgt ttttctttat    3720
tcttcggaac catagcacaa ctacggctag tgtgatctgg atctaaaatg atggctgatg    3780
aaaaaattct gattaaagca ccaagaagcc acaaagacgg gcatcttttt gaagtgcacg    3840
aatcttctgc agattgggta gaacaatacc aacacttcaa aggggtgacc aaaagcatct    3900
tagaattgct taatctgatc tcgttgagag gtttcagcag caaagatgga cttgtatcaa    3960
ccactgaaat cgttgaagca acagatggtc aactgactcg tgctgcgtta caacaacgat    4020
tacgagcagc ggtgaacatt ggtttattta cgcaaactcc agttcgcttt gaagaaggac    4080
tggcaggtaa aaccatgctt cacacgtttg ttaatcccaa taagctcatt tccgctttgg    4140
gtgcaacgag cttagttact gaaaaagtcc gccagaatga aaaacaaaaa cgctcaaaag    4200
cactagctca gacgcaagta aacaaacgct tgctgacaga acatggctta aacacgccgc    4260
cgacgatgaa agatgaagcg gatcaattcg tcgtctctcc aactaattgg gcagggatca    4320
ttgaccaagc tttggcgcca ccacgtactc gtaagagtta tcagaagtcg atggtgtcga    4380
tctctggtac gaaagcggta atagaaactc gatcgtcaaa aaatatcatg acagtcgatg    4440
atctgatgac cttgtttgcg ctgtttaccc tgaccgtgca ataccatgat catcacaaag    4500
atcagtacca tcttgatgca gctcatgtac cgaataaaac accgctgtat atcaccgaca    4560
tcctgtcatt gcgtggcaaa aaggacagtg gacctgctcg tgattccatt cgtgacagta    4620
tcgatagaat cgaattcacc gacttccagt tacatgagct tacaggccgc tggttaagtg    4680
aaaacatgcc ggaaggtttt aaaagtgatc gattccgctt tctagcgcga acgatcaccg    4740
catcagaaga agcgccagtt gagggcagcg acggtgagat ccgaatcaaa cctaatttgt    4800
acatattggt ttgggagccg tcgtttttacg aggaattact gactcgtgat tacttcttcc    4860
tgtttccgcc agagattctg aaacaacata ctttggtgtt ccagttatat tccttttttcc    4920 gtagccggat ggttcgtcgc catacggatt gtatgttgct tagtgaactg aatcagaagt    4980
tagcgcgtaa catcgagtgg cgtcgattct ccatggatct tatccgggaa ctgaaacgat    5040
tatctgatgg aaaagggacg gaagatcttt ttgttgttaa cttatggggc taccacctga    5100
cgatcgaaac catgatcgag aaaggcaaaa tcatggatta ccagatcgat atcaagtgtg    5160
atgttgagga agtcttgcgt tattcacgtg ctcgtaccac aaacgcagga aagcgtaaca    5220
tggctcctac gctgccaaac ccacttcgta atgagatggt atccaaacaa cagctagaag    5280
agctctcagg catcattgac ggcgaatttg agcctattca gcgcaaagca ccgtctcctc    5340
gtggtaattt agggcgtagg atcaagcaaa gaaaacatct ggttgagatt aatgcagatg    5400
aaattaccat tactctatcc aaatatacct caccagaggc tctggaacgc agcataacgg    5460
cgttatcagc aatgacaggg cactcatacg cctcgattaa ggaagagtgc tctgagtaca    5520
ttgagaagct tgattggtta agagttggag atgacccatt accttatgag actctgagta    5580
agaccgttga gctgttcaat acgcaaaatg atctcaaaca tcttactatt gagcgtctga    5640
ttgccggttt agctgttcgt cgcaaggtct gcagacaaat ttatgatggc catatggatg    5700
agatggtgta tcgagctctt gatgaaatgg cgatttaaca tcattcagct ttatgaattg    5760
aaaccgatta atgtgactga ttgattttaa atgtaaatat atatttcgat aatagaaaac    5820
gtcgacgagc tcgcgagctc ggacatgagg ttgccccgta ttcagtgtcg ctgatttgta    5880
ttgtctgaag ttgtttttac gttaagttga tgcagatcaa ttaatacgat acctgcgtca    5940
```

```
taattgatta tttgacgtgg tttgatggcc tccacgcacg ttgtgatatg tagatgataa    6000
tcattatcac tttacgggtc ctttccggtg atccgacagg ttacggggcg gcgacctcgc    6060
gggttttcgc tatttatgaa aattttccgg tttaaggcgt ttccgttctt cttcgtcata    6120
acttaatgtt tttatttaaa ataccctctg aaaagaaagg aaacgacagg tgctgaaagc    6180
gagctttttg gcctctgtcg tttcctttct ctgtttttgt ccgtggaatg aacaatggaa    6240
gtccgagctc atcgctaata acttcgtata gcatacatta tacgaagtta tattcgatgc    6300
ggccgcaagg ggttcgcgtc agcgggtgtt ggcgggtgtc ggggctggct taactatgcg    6360
gcatcagagc agattgtact gagagtgcac catatgcggt gtgaaatacc acacagatgc    6420
gtaaggagaa aataccgcat caggcgccat tcgccattca gctgcgcaac tgttgggaag    6480
ggcgatcggt gcgggcctct tcgctattac gccagctggc gaaagggggga tgtgctgcaa    6540 ggcgattaag ttgggtaacg ccagggtttt cccagtcacg acgttgtaaa acgacggcca    6600
gtgaattgta atacgactca ctatagggcg aattcgagct cggtacccgg ggatcctcta    6660
gagtcgacct gcaggcatgc aagcttgagt attctatagt ctcacctaaa tagcttggcg    6720
taatcatggt catagctgtt tcctgtgtga aattgttatc cgctcacaat tccacacaac    6780
atacgagccg gaagcataaa gtgtaaagcc tggggtgcct aatgagtgag ctaactcaca    6840
ttaattgcgt tgcgctcact gcccgctttc cagtcgggaa acctgtcgtg ccagctgcat    6900
taatgaatcg gccaacgcga accccttgcg gccgcccggg ccgtcgacca attctcatgt    6960
ttgacagctt atcatcgaat ttctgccatt catccgctta ttatcactta ttcaggcgta    7020
gcaaccaggc gtttaagggc accaataact gccttaaaaa aattacgccc cgccctgcca    7080
ctcatcgcag tactgttgta attcattaag cattctgccg acatggaagc catcacaaac    7140
ggcatgatga acctgaatcg ccagcggcat cagcaccttg tcgccttgcg tataatattt    7200
gcccatggtg aaaacggggg cgaagaagtt gtccatattg ccacgtttaa atcaaaact    7260 ggtgaaactc acccagggat tggctgagac gaaaaacata ttctcaataa acccttatgg    7320
gaaataggcc aggttttcac cgtaacacgc cacatcttgc gaatatatgt gtagaaactg    7380
ccggaaatcg tcgtggtatt cactccagag cgatgaaaac gtttcagttt gctcatggaa    7440
aacggtgtaa caagggtgaa cactatccca tatcaccagc tcaccgtctt tcattgccat    7500
acgaaattcc ggatgagcat tcatcaggcg ggcaagaatg tgaataaagg ccggataaaa    7560
cttgtgctta ttttctttta cggtctttaa aaaggccgta atatccagct gaacggtctg    7620
gttataggta cattgagcaa ctgactgaaa tgcctcaaaa tgttctttac gatgccattg    7680
ggatatatca acggtggtat atccagtgat ttttttctcc attttagctt ccttagctcc    7740
tgaaaatctc gataactcaa aaaatacgcc cggtagtgat cttatttcat tatggtgaaa    7800
gttggaacct cttacgtgcc gatcaacgtc tcattttcgc caaaagttgg cccagggctt    7860
cccggtatca acagggacac caggatttat ttattctgcg aagtgatctt ccgtcacagg    7920
tatttattcg cgataagctc atggagcggc gtaaccgtcg cacaggaagg acagagaaag    7980
cgcggatctg ggaagtgacg gacagaacgg tcaggacctg gattggggag gcggttgccg    8040
ccgctgctgc tgacggtgtg acgttctctg ttccggtcac accacatacg ttccgccatt    8100
cctatgcgat gcacatgctg tatgccggta taccgctgaa agttctgcaa agcctgatgg    8160
gacataagtc catcagttca acggaagtct acacgaaggt ttttgcgctg gatgtggctg    8220
cccggcaccg ggtgcagttt gcgatgccgg agtctgatgc ggttgcgatg ctgaaacaat    8280
tatcctgaga ataaatgcct tggcctttat atggaaatgt ggaactgagt ggatatgctg    8340
```

-continued

```
ttttttgtctg ttaaacagag aagctggctg ttatccactg agaagcgaac gaaacagtcg    8400
ggaaaatctc ccattatcgt agagatccgc attattaatc tcaggagcct gtgtagcgtt    8460
tataggaagt agtgttctgt catgatgcct gcaagcggta acgaaaacga tttgaatatg    8520
ccttcaggaa caatagaaat cttcgtgcgg tgttacgttg aagtggagcg gattatgtca    8580
gcaatggaca gaacaaccta atgaacacag aaccatgatg tggtctgtcc ttttacagcc    8640
agtagtgctc gccgcagtcg agcgacaggg cgaagccctc gagctggttg ccctcgccgc    8700
tgggctggcg gccgtctatg gccctgcaaa cgcgccagaa acgccgtcga agccgtgtgc    8760
gagacaccgc ggccggccgc cggcgttgtg gatacctcgc ggaaaacttg gccctcactg    8820
acagatgagg ggcggacgtt gacacttgag gggccgactc acccggcgcg gcgttgacag    8880
atgaggggca ggctcgattt cggccggcga cgtggagctg gccagcctcg caaatcggcg    8940
aaaacgcctg attttacgcg agtttcccac agatgatgtg gacaagcctg gggataagtg    9000
ccctgcggta ttgacacttg aggggcgcga ctactgacag atgaggggcg cgatccttga    9060
cacttgaggg gcagagtgct gacagatgag gggcgcacct attgacattt gaggggctgt    9120
ccacaggcag aaaatccagc atttgcaagg gtttccgccc gttttttcggc caccgctaac    9180 ctgtctttta acctgctttt aaaccaatat ttataaacct gttttttaac cagggctgcg    9240
ccctgtgcgc gtgaccgcgc acgccgaagg ggggtgcccc ccttctcga accctcccgg     9300 cagttcgctc gctatgctcg gttacacggc tgcggcgagc atcacgtgct ataaaaataa    9360
ttataattta aatttttttaa tataaatata taaattaaaa atagaaagta aaaaaagaaa    9420
ttaaagaaaa aatagttttt gttttccgaa gatgtaaaag actctagggg gatcgccaac    9480
aaatactacc ttttatcttg ctcttcctgc tctcaggtat taatgccgaa ttgtttcatc    9540
ttgtctgtgt agaagaccac acacgaaaat cctgtgattt tacattttac ttatcgttaa    9600
tcgaatgtat atctatttaa tctgcttttc ttgtctaata aatatatatg taaagtacgc    9660
tttttgttga aattttttaa acctttgttt atttttttttt cttcattccg taactcttct    9720 accttctttta tttactttct aaaatccaaa tacaaaacat aaaaataaat aaacacagag    9780
taaattccca aattattcca tcattaaaag atacgaggcg cgtgtaagtt acaggcaagc    9840
gatccgtcct aagaaaccat tattatcatg acattaacct ataaaaatag gcgtatcacg    9900
aggccctttc gtctcgcgcg tttcggtgat gacggtgaaa acctctgaca catgcagctc    9960
ccggagacgg tcacagcttg tctgtaagcg gatgccggga gcagacaagc ccgtcagggc    10020
gcgtcagcgg gtgttggcgg gtgtcggggc tggcttaact atgcggcatc agagcagatt    10080
gtactgagag tgcaccataa acgacattac tatatatata atataggaag catttaatag    10140
acagcatcgt aatatatgtg tactttgcag ttatgacgcc agatggcagt agtggaagat    10200
attctttatt gaaaaatagc ttgtcacctt acgtacaatc ttgatccgga gcttttcttt    10260
ttttgccgat taagaattaa ttcggtcgaa aaaagaaaag gagagggcca agagggaggg    10320
cattggtgac tattgagcac gtgagtatac gtgattaagc acacaaaggc agcttggagt    10380
atgtctgtta ttaatttcac aggtagttct ggtccattgg tgaaagtttg cggcttgcag    10440
agcacagagg ccgcagaatg tgctctagat tccgatgctg acttgctggg tattatatgt    10500
gtgcccaata gaaagagaac aattgacccg gttattgcaa ggaaaatttc aagtcttgta    10560
aaagcatata aaaatagttc aggcactccg aaatacttgg ttggcgtgtt tcgtaatcaa    10620
cctaaggagg atgttttggc tctggtcaat gattacggca ttgatatcgt ccaactgcat    10680
```

-continued

```
ggagatgagt cgtggcaaga ataccaagag ttcctcggtt tgccagttat taaaagactc   10740
gtatttccaa aagactgcaa catactactc agtgcagctt cacagaaacc tcattcgttt   10800
attcccttgt ttgattcaga agcaggtggg acaggtgaac ttttggattg gaactcgatt   10860
tctgactggg ttggaaggca agagagcccc gaaagcttac attttatgtt agctggtgga   10920
ctgacgccag aaaatgttgg tgatgcgctt agattaaatg gcgttattgg tgttgatgta   10980
agcggaggtg tggagacaaa tggtgtaaaa gactctaaca aaatagcaaa tttcgtcaaa   11040
aatgctaaga aataggttat tactgagtag tatttattta agtattgttt gtgcacttgc   11100
ctatgcggtg tgaaataccg cacagatgcg taaggagaaa ataccgcatc aggaaattgt   11160
aaacgttaat attttgttaa aattcgcgtt aaattttgt taaatcagct catttttttaa   11220 ccaataggcc gaaatcggca aaatcgctag tgataataag tgactgaggt atgtgctctt   11280
cttat                                                              11285
```

<210> SEQ ID NO 5
<211> LENGTH: 1217
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: araC-araBAD promoter fragment

<400> SEQUENCE: 5

```
ttatgacaac ttgacggcta catcattcac tttttcttca caaccggcac ggaactcgct     60
cgggctggcc ccggtgcatt ttttaaatac ccgcgagaaa tagagttgat cgtcaaaacc    120
aacattgcga ccgacggtgg cgataggcat ccgggtggtg ctcaaaagca gcttcgcctg    180
gctgatacgt tggtcctcgc gccagcttaa gacgctaatc cctaactgct ggcggaaaag    240
atgtgacaga cgcgacggcg acaagcaaac atgctgtgcg acgctggcga tatcaaaatt    300
gctgtctgcc aggtgatcgc tgatgtactg acaagcctcg cgtacccgat tatccatcgg    360
tggatggagc gactcgttaa tcgcttccat cgcccgcagt aacaattgct caagcagatt    420
tatcgccagc agctccgaat agcgcccttc cccttgcccg cgttaatga tttgcccaaa     480 caggtcgctg aaatgcggct ggtgcgcttc atccgggcga agaacccccg tattggcaaa    540
tattgacggc cagttaagcc attcatgcca gtaggcgcgc ggacgaaagt aaacccactg    600
gtgataccat tcgcgagcct ccggatgacg accgtagtga tgaatctctc ctggcgggaa    660
cagcaaaata tcacccggtc ggcaaacaaa ttctcgtccc tgattttttca ccaccccctg    720 accgcgaatg gtgagattga gaatataacc tttcattccc agcggtcggt cgataaaaaa    780
atcgagataa ccgttggcct caatcggcgt taaacccgcc accagatggg cattaaacga    840
gtatcccggc agcaggggat cattttgcgc ttcagccata cttttcatac tcccgccatt    900
cagagaagaa accaattgtc catattgcat cagacattgc cgtcactgcg tctttttactg    960 gctcttctcg ctaaccaaac cggtaacccc gcttattaaa agcattctgt aacaaagcgg   1020
gaccaaagcc atgacaaaaa cgcgtaacaa aagtgtctat aatcacggca gaaaagtcca   1080
cattgattat ttgcacggcg tcacactttg ctatgccata gcattttttat ccataagatt   1140 agcggatcct acctgacgct ttttatcgca actctctact gtttctccat accgttttt    1200 ttggatggag tgaaacg                                                 1217
```

<210> SEQ ID NO 6

<211> LENGTH: 1937
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: lac operon regulatory elements and lacI protein

<400> SEQUENCE: 6
ttatttgatt tcaattttgt cccactccct gcctctgtca tcacgatact gtgatgccat      60
ggtgtccgac ttatgcccga gaagatgttg agcaaactta tcgcttatct gcttctcata     120
gagtcttgca gacaaactgc gcaactcgtg aaaggtaggc ggatccagat cccggacacc     180
atcgaatggc gcaaaacctt tcgcggtatg gcatgatagc gcccggaaga gagtcaattc     240
agggtggtga atgtgaaacc agtaacgtta tacgatgtcg cagagtatgc cggtgtctct     300
tatcagaccg tttcccgcgt ggtgaaccag gccagccacg tttctgcgaa aacgcgggaa     360
aaagtggaag cggcgatggc ggagctgaat tacattccca accgcgtggc acaacaactg     420
gcgggcaaac agtcgttgct gattggcgtt gccacctcca gtctggccct gcacgcgccg     480
tcgcaaattg tcgcggcgat taaatctcgc gccgatcaac tgggtgccag cgtggtggtg     540
tcgatggtag aacgaagcgg cgtcgaagcc tgtaaagcgg cggtgcacaa tcttctcgcg     600
caacgcgtca gtgggctgat cattaactat ccgctggatg accaggatgc cattgctgtg     660
gaagctgcct gcactaatgt tccggcgtta tttcttgatg tctctgacca gacacccatc     720
aacagtatta ttttctccca tgaagacggt acgcgactgg cgtggagca tctggtcgca     780 ttgggtcacc agcaaatcgc gctgttagcg ggcccattaa gttctgtctc ggcgcgtctg     840
cgtctggctg gctggcataa atatctcact cgcaatcaaa ttcagccgat agcggaacgg     900
gaaggcgact ggagtgccat gtccggtttt caacaaacca tgcaaatgct gaatgagggc     960
atcgttccca ctgcgatgct ggttgccaac gatcagatgg cgctgggcgc aatgcgcgcc    1020
attaccgagt ccgggctgcg cgttggtgcg gatatctcgg tagtgggata cgacgatacc    1080
gaagacagct catgttatat cccgccgtta accaccatca aacaggattt tcgcctgctg    1140
gggcaaacca gcgtggaccg cttgctgcaa ctctctcagg gccaggcggt gaagggcaat    1200
cagctgttgc ccgtctcact ggtgaaaaga aaaaccaccc tggcgcccaa tacgcaaacc    1260
gcctctcccc gcgcgttggc cgattcatta atgcagctgg cacgacaggt ttcccgactg    1320
gaaagcgggc agtgagcgca acgcaattaa tgtaagttag ctcactcatt aggcaccccca    1380 ggctttacac tttatgcttc cggctcgtat aatgtgtgga attgtgagcg ataacaatt    1440 tcacacagga aacagctatg accatgatta cggattcact ggccgtcgtt ttacaacgtc    1500
gtgactggga aaaccctggc gttacccaac ttaatcgcct tgcagcacat ccccctttcg    1560
ccagctggcg taatagcgaa gaggcccgca ccgatcgccc ttcccaacag ttgcgcagcc    1620
tgaatggcga atggcgcttt gcctggtttc cggcaccaga agcggtgccg gaaagctggc    1680
tggagtgcga tcttcctgag gccgatactg tcgtcgtccc ctcaaactgg cagatgcacg    1740
gttacgatgc gcccatctac accaacgtga cctatcccat tacggtcaat ccgccgtttg    1800
ttcccacgga gaatccgacg ggttgttact cgctcacatt taatgttgat gaaagctggc    1860
tacaggaagg ccagacgcga attattttg atggcgtcgg gatctgatcc ggatttacta    1920
actggaagag gcactaa                                                   1937

<210> SEQ ID NO 7

-continued

```
<211> LENGTH: 2652
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T7 RNA polymerase gene

<400> SEQUENCE: 7
atgaacacga ttaacatcgc taagaacgac ttctctgaca tcgaactggc tgctatcccg       60
ttcaacactc tggctgacca ttacggtgag cgtttagctc gcgaacagtt ggcccttgag      120
catgagtctt acgagatggg tgaagcacgc ttccgcaaga tgtttgagcg tcaacttaaa      180
gctggtgagg ttgcggataa cgctgccgcc aagcctctca tcactaccct actccctaag      240
atgattgcac gcatcaacga ctggtttgag gaagtgaaag ctaagcgcgg caagcgcccg      300
acagccttcc agttcctgca agaaatcaag ccggaagccg tagcgtacat caccattaag      360
accactctgg cttgcctaac cagtgctgac aatacaaccg ttcaggctgt agcaagcgca      420
atcggtcggg ccattgagga cgaggctcgc ttcggtcgta tccgtgacct tgaagctaag      480
cacttcaaga aaaacgttga ggaacaactc aacaagcgcg tagggcacgt ctacaagaaa      540
gcatttatgc aagttgtcga ggctgacatg ctctctaagg gtctactcgg tggcgaggcg      600
tggtcttcgt ggcataagga agactctatt catgtaggag tacgctgcat cgagatgctc      660
attgagtcaa ccggaatggt tagcttacac cgccaaaatg ctggcgtagt aggtcaagac      720
tctgagacta tcgaactcgc acctgaatac gctgaggcta tcgcaacccg tgcaggtgcg      780
ctggctggca tctctccgat gttccaacct tgcgtagttc ctcctaagcc gtggactggc      840
attactggtg gtggctattg ggctaacggt cgtcgtcctc tggcgctggt gcgtactcac      900
agtaagaaag cactgatgcg ctacgaagac gtttacatgc ctgaggtgta caaagcgatt      960
aacattgcgc aaaacaccgc atggaaaatc aacaagaaag tcctagcggt cgccaacgta     1020
atcaccaagt ggaagcattg tccggtcgag gacatccctg cgattgagcg tgaagaactc     1080
ccgatgaaac cggaagacat cgacatgaat cctgaggctc tcaccgcgtg gaaacgtgct     1140
gccgctgctg tgtaccgcaa ggacaaggct cgcaagtctc gccgtatcag ccttgagttc     1200
atgcttgagc aagccaataa gtttgctaac cataaggcca tctggttccc ttacaacatg     1260
gactggcgcg tcgtgtttta cgctgtgtca atgttcaacc cgcaaggtaa cgatatgacc     1320
aaaggactgc ttacgctggc gaaaggtaaa ccaatcggta aggaaggtta ctactggctg     1380
aaaatccacg gtgcaaactg tgcgggtgtc gataaggttc cgttccctga gcgcatcaag     1440
ttcattgagg aaaaccacga gaacatcatg gcttgcgcta agtctccact ggagaacact     1500
tggtgggctg agcaagattc tccgttctgc ttccttgcgt tctgctttga gtacgctggg     1560
gtacagcacc acggcctgag ctataactgc tcccttccgc tggcgtttga cgggtcttgc     1620
tctggcatcc agcacttctc cgcgatgctc cgagatgagg taggtggtcg cgcggttaac     1680
ttgcttccta gtgaaaccgt tcaggacatc tacgggattg ttgctaagaa agtcaacgag     1740
attctacaag cagacgcaat caatgggacc gataacgaag tagttaccgt gaccgatgag     1800
aacactggtg aaatctctga aaagtcaag ctgggcacta aggcactggc tggtcaatgg     1860
ctggcttacg tgttactccg cagtgtgact aagcgttcag tcatgacgct ggcttacggg     1920
tccaaagagt tcggcttccg tcaacaagtg ctggaagata ccattcagcc agctattgat     1980
tccggcaagg gtctgatgtt cactcagccg aatcaggctg ctggatacat ggctaagctg     2040
```

```
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aa                                                        2652
```

```
<210> SEQ ID NO 8
<211> LENGTH: 37
<212> TYPE: PRT
<213> ORGANISM: Vibrio natriegens

<400> SEQUENCE: 8

Met Arg Ile Leu Leu Thr Glu Val Ser Lys Met Arg Ser Thr Lys Met
1               5                   10                  15

Lys Ala Gly Val Pro Ile Leu Gly Ile Leu Met Gly Thr Ala Ala Ser
            20                  25                  30

Gln Leu Ala Phe Ala
        35

<210> SEQ ID NO 9
<211> LENGTH: 27
<212> TYPE: PRT
<213> ORGANISM: Vibrio natriegens

<400> SEQUENCE: 9

Met Arg Ser Thr Lys Met Lys Ala Gly Val Pro Ile Leu Gly Ile Leu
1               5                   10                  15

Met Gly Thr Ala Ala Ser Gln Leu Ala Phe Ala
            20                  25

<210> SEQ ID NO 10
<211> LENGTH: 25
<212> TYPE: PRT
<213> ORGANISM: Vibrio natriegens

<400> SEQUENCE: 10

Met Gln Met Lys Thr Met Lys Ser Lys Leu Ala Val Ala Leu Ile Ala
1               5                   10                  15

Ala Gly Leu Ser Phe Asn Ser Leu Ala
            20                  25

<210> SEQ ID NO 11
<211> LENGTH: 50
<212> TYPE: PRT
<213> ORGANISM: Vibrio natriegens

<400> SEQUENCE: 11

Met Arg Asn Asn Gln Leu Thr Leu Ala Leu Lys Lys Ile Lys Lys Gly
1               5                   10                  15

Ile Arg Lys Gly Tyr Pro Lys Leu Arg Lys Gly Ser Gly Leu Ile Met
```

-continued

```
              20                25                30

Lys Lys Thr Leu Leu Ala Leu Ala Val Ala Thr Val Ser Thr Ser Ala
      35                40                45

Leu Ala
      50

<210> SEQ ID NO 12
<211> LENGTH: 19
<212> TYPE: PRT
<213> ORGANISM: Vibrio natriegens

<400> SEQUENCE: 12

Met Lys Lys Thr Leu Leu Ala Leu Ala Val Ala Thr Val Ser Thr Ser
1               5                10                15

Ala Leu Ala

<210> SEQ ID NO 13
<211> LENGTH: 22
<212> TYPE: PRT
<213> ORGANISM: Vibrio natriegens

<400> SEQUENCE: 13

Met Lys Lys Leu Ser Ala Val Ala Leu Gly Thr Leu Val Ala Leu Gly
1               5                10                15

Ser Phe Gly Ala His Ala
            20

<210> SEQ ID NO 14
<211> LENGTH: 26
<212> TYPE: PRT
<213> ORGANISM: Vibrio natriegens

<400> SEQUENCE: 14

Met Glu Leu Arg Met Lys Lys Val Ser Val Ile Ala Ala Ala Val Ala
1               5                10                15

Ala Ser Leu Ala Ala Gly Ser Ala Phe Ala
            20                25

<210> SEQ ID NO 15
<211> LENGTH: 22
<212> TYPE: PRT
<213> ORGANISM: Vibrio natriegens

<400> SEQUENCE: 15

Met Lys Lys Val Ser Val Ile Ala Ala Ala Val Ala Ala Ser Leu Ala
1               5                10                15

Ala Gly Ser Ala Phe Ala
            20

<210> SEQ ID NO 16
<211> LENGTH: 21
<212> TYPE: PRT
<213> ORGANISM: Vibrio natriegens

<400> SEQUENCE: 16

Met Lys Lys Thr Leu Ile Ala Leu Ser Val Ser Ala Ala Ala Met Ala
1               5                10                15

Thr Gly Val Asn Ala
            20

<210> SEQ ID NO 17
```

```
<211> LENGTH: 32
<212> TYPE: PRT
<213> ORGANISM: Vibrio natriegens

<400> SEQUENCE: 17

Met Gln Ser Ile Gln Gly Asn Ile Met Asn Lys Val Ala Ile Ala Val
1               5                   10                  15

Ala Ala Val Val Ala Gly Gly Ser Ala Leu Leu Asn Thr Ala Gln Ala
            20                  25                  30

<210> SEQ ID NO 18
<211> LENGTH: 24
<212> TYPE: PRT
<213> ORGANISM: Vibrio natriegens

<400> SEQUENCE: 18

Met Ala Phe Asn Lys Leu Leu Lys Val Gly Ala Ile Ala Ala Ala Val
1               5                   10                  15

Met Gly Ala Gly Ala Val Asn Ala
            20

<210> SEQ ID NO 19
<211> LENGTH: 26
<212> TYPE: PRT
<213> ORGANISM: Vibrio natriegens

<400> SEQUENCE: 19

Met Lys Lys Pro Leu Leu Ala Leu Thr Val Leu Ser Leu Ser Leu Ser
1               5                   10                  15

Ser Ile Phe Thr Pro Ile Gln Ala Thr Ala
            20                  25

<210> SEQ ID NO 20
<211> LENGTH: 21
<212> TYPE: PRT
<213> ORGANISM: Vibrio natriegens

<400> SEQUENCE: 20

Met Lys Lys Val Leu Thr Leu Ser Ala Leu Ala Cys Ala Thr Leu Ala
1               5                   10                  15

Pro Thr Ala Met Ala
            20

<210> SEQ ID NO 21
<211> LENGTH: 21
<212> TYPE: PRT
<213> ORGANISM: Vibrio natriegens

<400> SEQUENCE: 21

Met Lys Lys Trp Leu Leu Ala Ala Thr Leu Ala Ala Thr Ala Val Ser
1               5                   10                  15

Gly Ala Val Gln Ala
            20

<210> SEQ ID NO 22
<211> LENGTH: 22
<212> TYPE: PRT
<213> ORGANISM: Vibrio natriegens

<400> SEQUENCE: 22

Met Met Lys Asn Trp Ile Lys Val Ala Val Ala Ala Ile Ala Leu Ser
1               5                   10                  15
```

```
Ala Ala Thr Val Gln Ala
            20

<210> SEQ ID NO 23
<211> LENGTH: 29
<212> TYPE: PRT
<213> ORGANISM: Vibrio natriegens

<400> SEQUENCE: 23

Met Asn Thr Gln Val Lys Lys Pro Ser Phe Met Pro Ser Ile Leu Ala
1               5                   10                  15

Ala Ala Val Val Thr Ala Phe Ser Gly Gln Ala Asn Ala
            20                  25

<210> SEQ ID NO 24
<211> LENGTH: 20
<212> TYPE: PRT
<213> ORGANISM: Vibrio natriegens

<400> SEQUENCE: 24

Met Lys Lys Leu Ala Ala Val Ile Ser Ala Ser Leu Leu Met Ala Ser
1               5                   10                  15

Ala Ala Gln Ala
            20

<210> SEQ ID NO 25
<211> LENGTH: 24
<212> TYPE: PRT
<213> ORGANISM: Vibrio natriegens

<400> SEQUENCE: 25

Met Asn Cys Ser His Lys Phe Lys Leu Thr Ala Ile Ala Met Met Val
1               5                   10                  15

Gly Ser Ser Met Ser Ala Asn Ala
            20

<210> SEQ ID NO 26
<211> LENGTH: 25
<212> TYPE: PRT
<213> ORGANISM: Vibrio natriegens

<400> SEQUENCE: 26

Met Asn Lys Leu Leu Thr Leu Thr Pro Leu Ala Val Ala Ile Gly Ser
1               5                   10                  15

Ser Leu Val Val Pro Ser Ala Val Ala
            20                  25

<210> SEQ ID NO 27
<211> LENGTH: 21
<212> TYPE: PRT
<213> ORGANISM: Vibrio natriegens

<400> SEQUENCE: 27

Met Lys Lys Thr Ile Cys Ser Leu Ala Val Val Ala Ala Leu Val Ser
1               5                   10                  15

Pro Ser Val Phe Ala
            20

<210> SEQ ID NO 28
<211> LENGTH: 33
<212> TYPE: PRT
<213> ORGANISM: Vibrio natriegens
```

-continued

```
<400> SEQUENCE: 28

Met Ala Ile Thr Arg Arg Ser Phe Leu Lys Gly Val Ala Thr Thr Ser
1               5                   10                  15

Ala Ala Ser Val Ile Gly Pro Ser Leu Leu Ala Ser Ala Ser Ala Lys
            20                  25                  30

Ala
```